United States Patent [19]
Kriesel

[11] Patent Number: 6,090,071
[45] Date of Patent: Jul. 18, 2000

[54] FLUID DISPENSER WITH FILL ADAPTER

[75] Inventor: Marshall S. Kriesel, Saint Paul, Minn.

[73] Assignee: Science Incorporated, Bloomington, Minn.

[21] Appl. No.: 09/329,840

[22] Filed: Jun. 10, 1999

Related U.S. Application Data

[63] Continuation-in-part of application No. 09/165,709, Oct. 2, 1998, Pat. No. 5,980,489, which is a continuation-in-part of application No. 08/729,326, Oct. 15, 1996, Pat. No. 5,873,857, which is a continuation-in-part of application No. 08/577,496, Dec. 22, 1995, Pat. No. 5,700,244, which is a continuation-in-part of application No. 08/192,031, Feb. 3, 1994, Pat. No. 5,484,415, which is a continuation-in-part of application No. 08/156,685, Nov. 22, 1993, Pat. No. 5,433,709, which is a continuation-in-part of application No. 08/053,723, Apr. 26, 1993, Pat. No. 5,354,278, which is a continuation-in-part of application No. 07/870,521, Apr. 17, 1992, Pat. No. 5,263,940.

[51] Int. Cl.[7] .................................................. A61M 37/00
[52] U.S. Cl. .......................................................... 604/131
[58] Field of Search .................................. 604/131, 132, 604/133, 151, 153, 190, 246–248, 232–236, 189, 80–83

[56] References Cited

U.S. PATENT DOCUMENTS

| | | |
|---|---|---|
| 3,378,008 | 4/1968 | Ogle . |
| 3,468,308 | 9/1969 | Bierman . |
| 3,469,578 | 9/1969 | Bierman . |
| 3,593,381 | 7/1971 | Ogle . |
| 3,828,779 | 8/1974 | Ogle . |
| 4,180,070 | 12/1979 | Genese . |
| 4,259,956 | 4/1981 | Ogle . |
| 4,296,747 | 10/1981 | Ogle . |
| 4,386,929 | 6/1983 | Perry et al. . |
| 4,419,096 | 12/1983 | Leeper et al. . |
| 4,607,671 | 8/1986 | Aalto et al. . |
| 4,886,495 | 12/1989 | Reynolds . |
| 4,915,693 | 4/1990 | Hessel . |
| 4,994,031 | 2/1991 | Theeuwes . |
| 5,067,948 | 11/1991 | Haber et al. . |
| 5,106,374 | 4/1992 | Apperson et al. . |
| 5,122,116 | 6/1992 | Kriesel et al. . |
| 5,171,214 | 12/1992 | Kolber et al. . |
| 5,188,603 | 2/1993 | Vaillancourt . |
| 5,199,604 | 4/1993 | Palmer et al. . |
| 5,533,993 | 7/1996 | Maier . |
| 5,830,187 | 11/1998 | Kriesel et al. . |

*Primary Examiner*—John D. Yasko
*Attorney, Agent, or Firm*—James E. Brunton

[57] ABSTRACT

An elastomeric bladder stored energy type infusion apparatus that can be filled with a medicinal fluid and, after being filled, can efficiently deliver the medicinal fluid to the patient at a selected, adjustable rate. The apparatus includes a built-in dose dialing mechanism which can be preset by the treating physician or health care worker so that a precise volume of the medicinal fluid can be introduced into the fluid reservoir of the device for delivery to the patient.

23 Claims, 35 Drawing Sheets

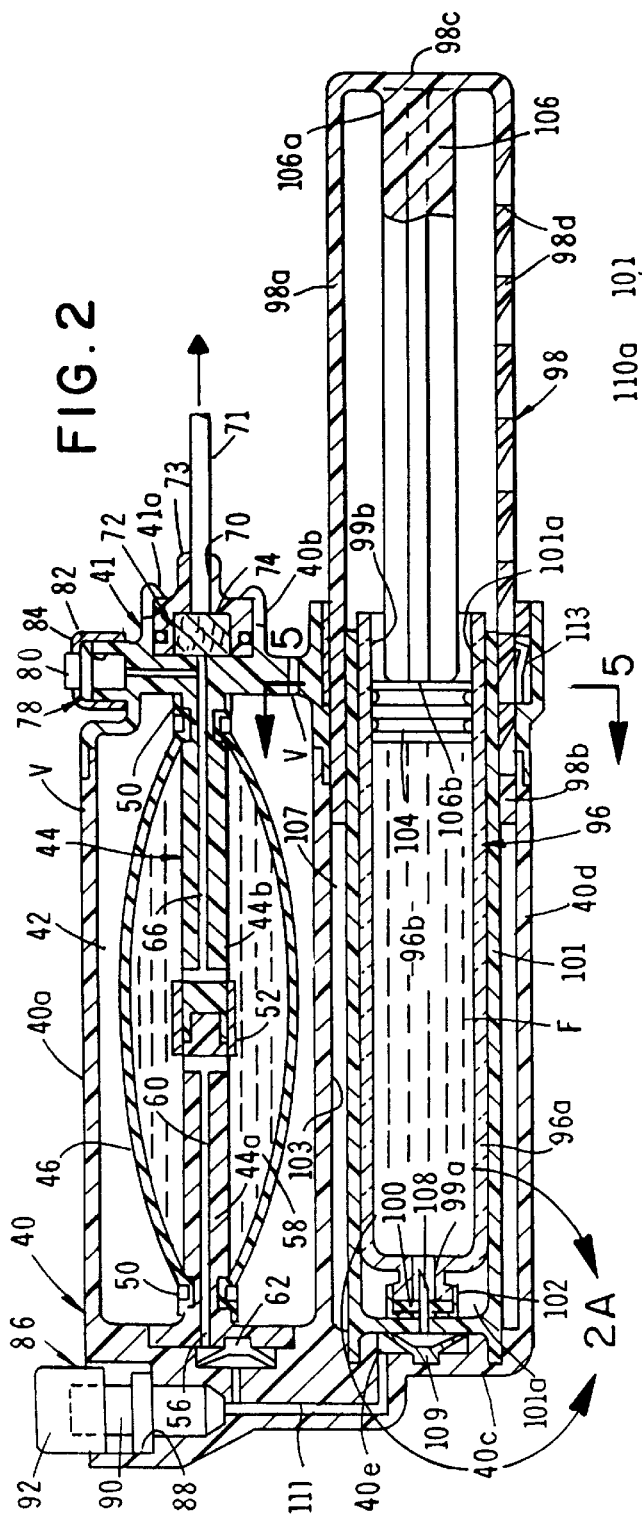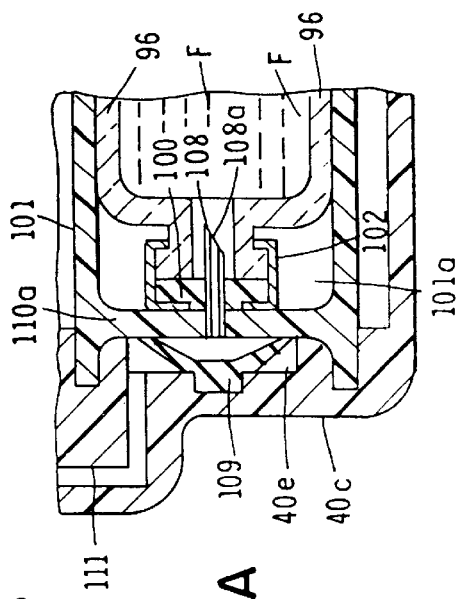

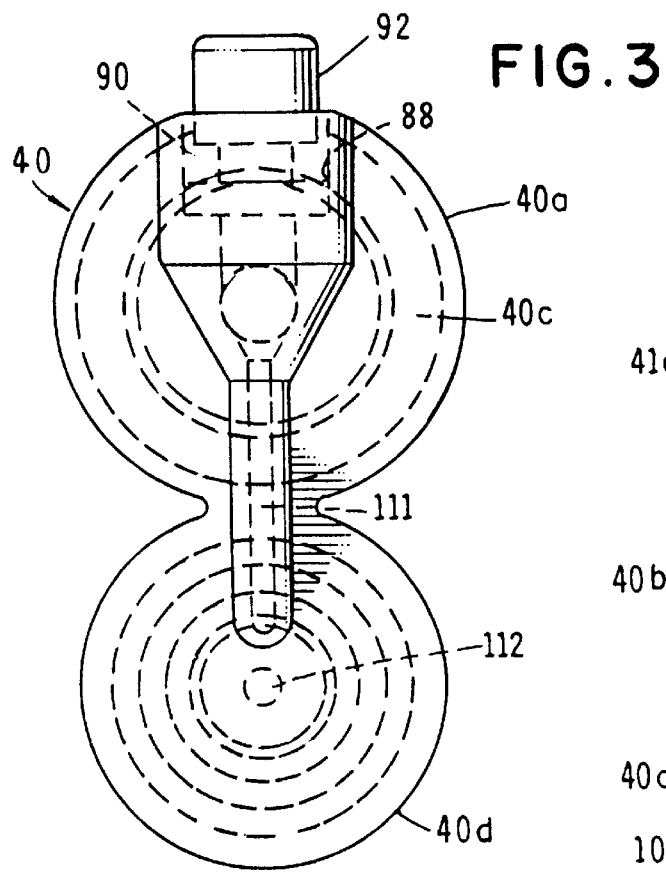
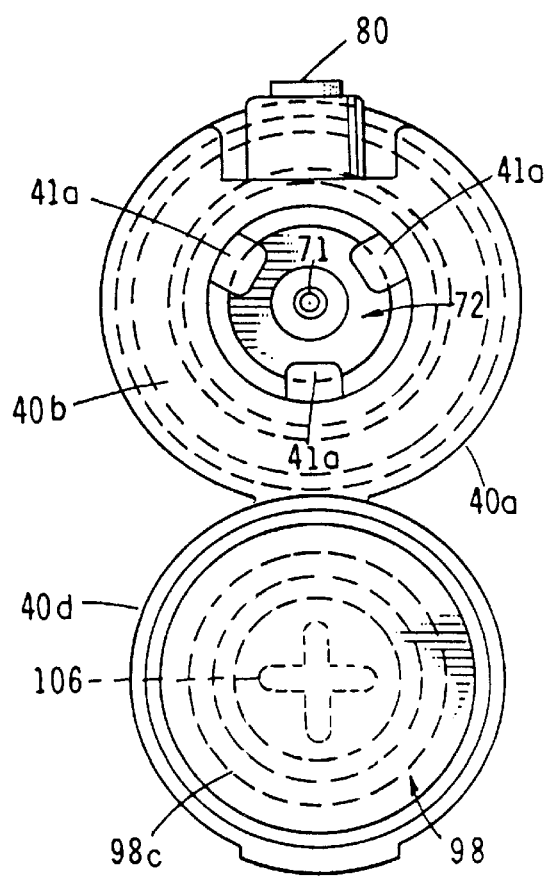
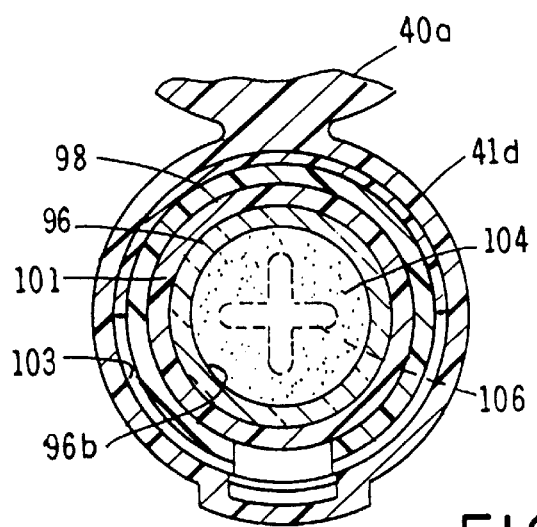
FIG. 3
FIG. 4
FIG. 5

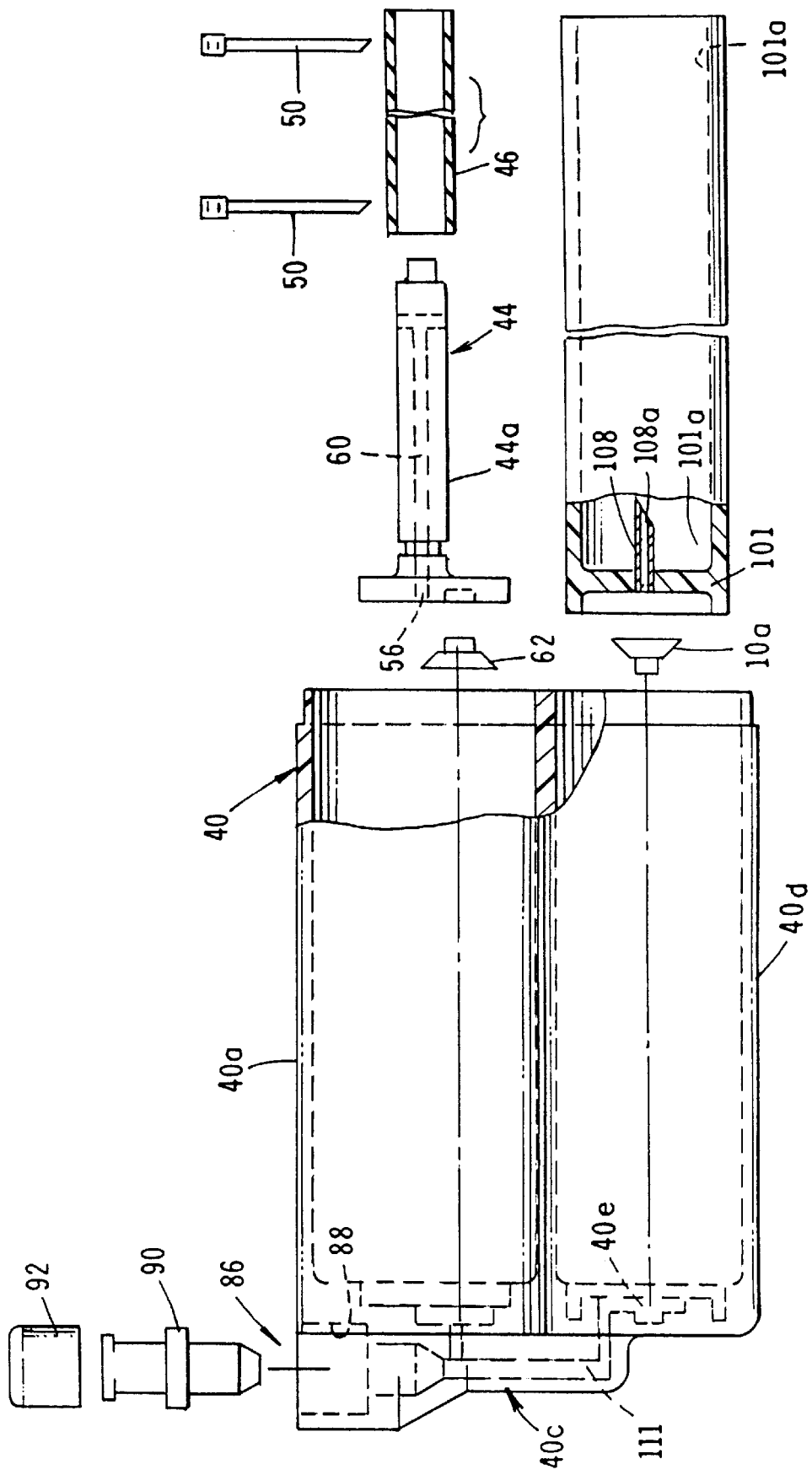

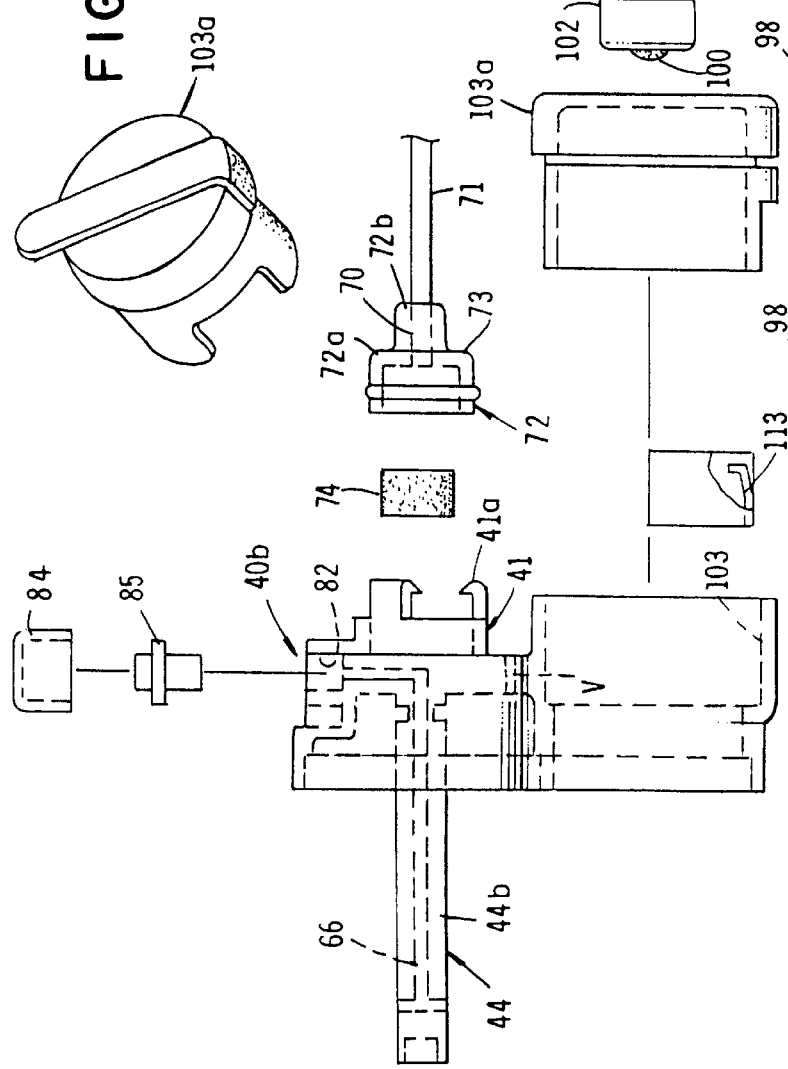

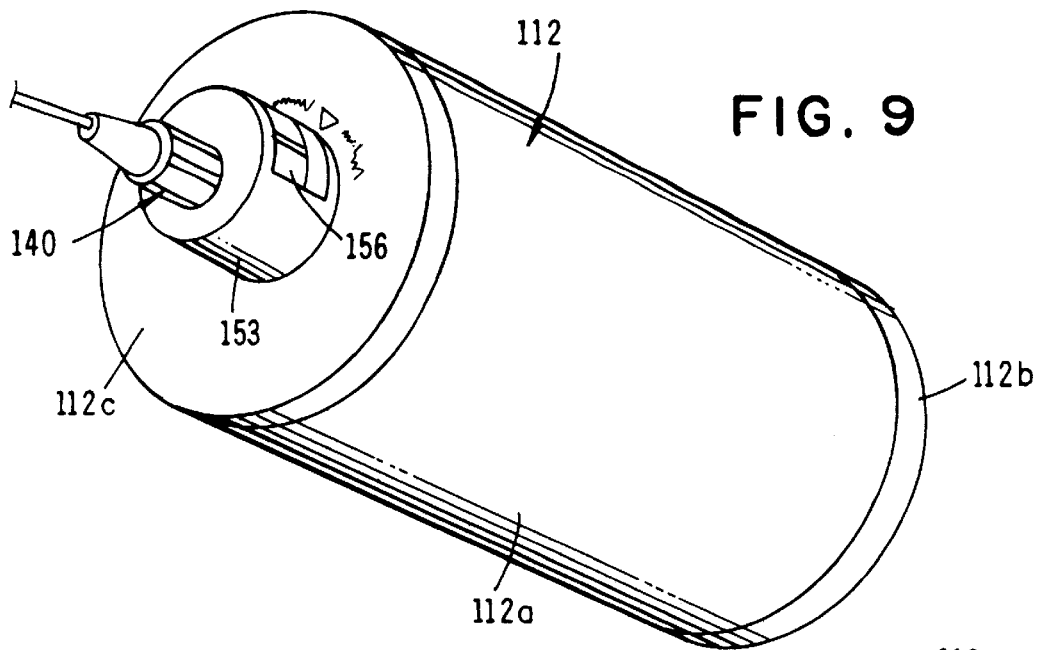
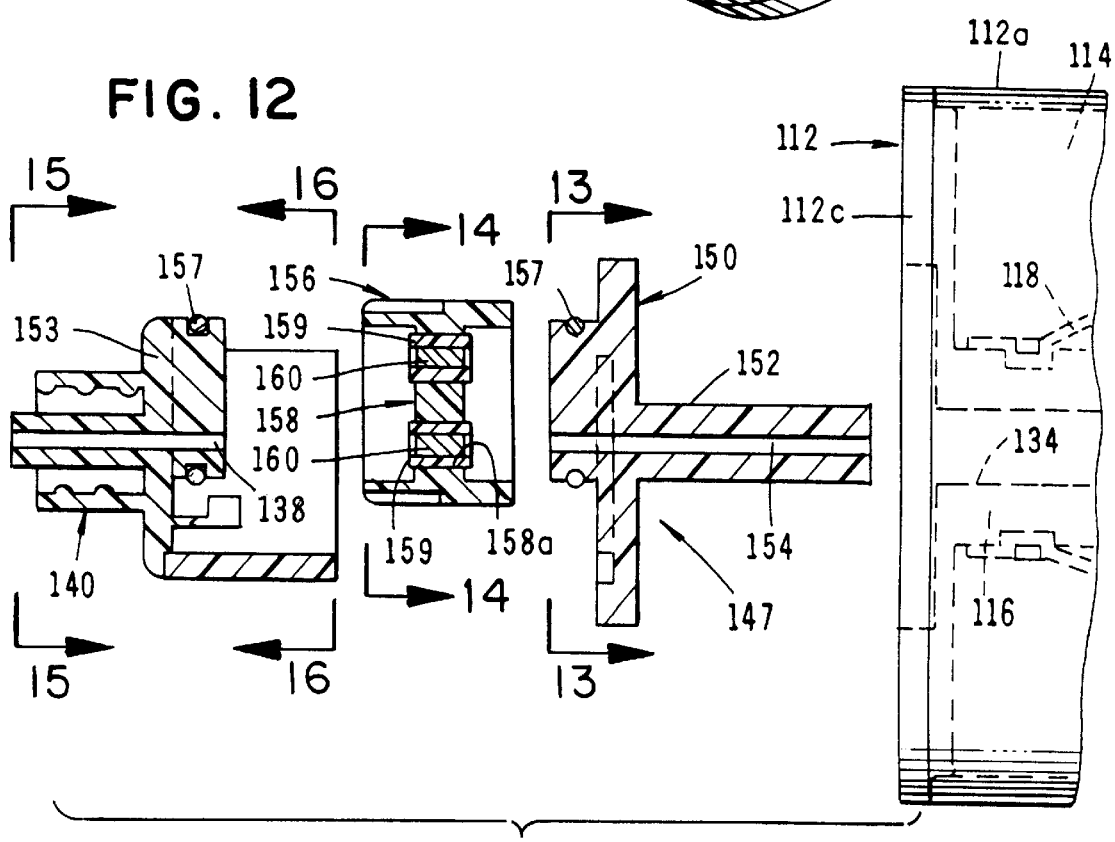

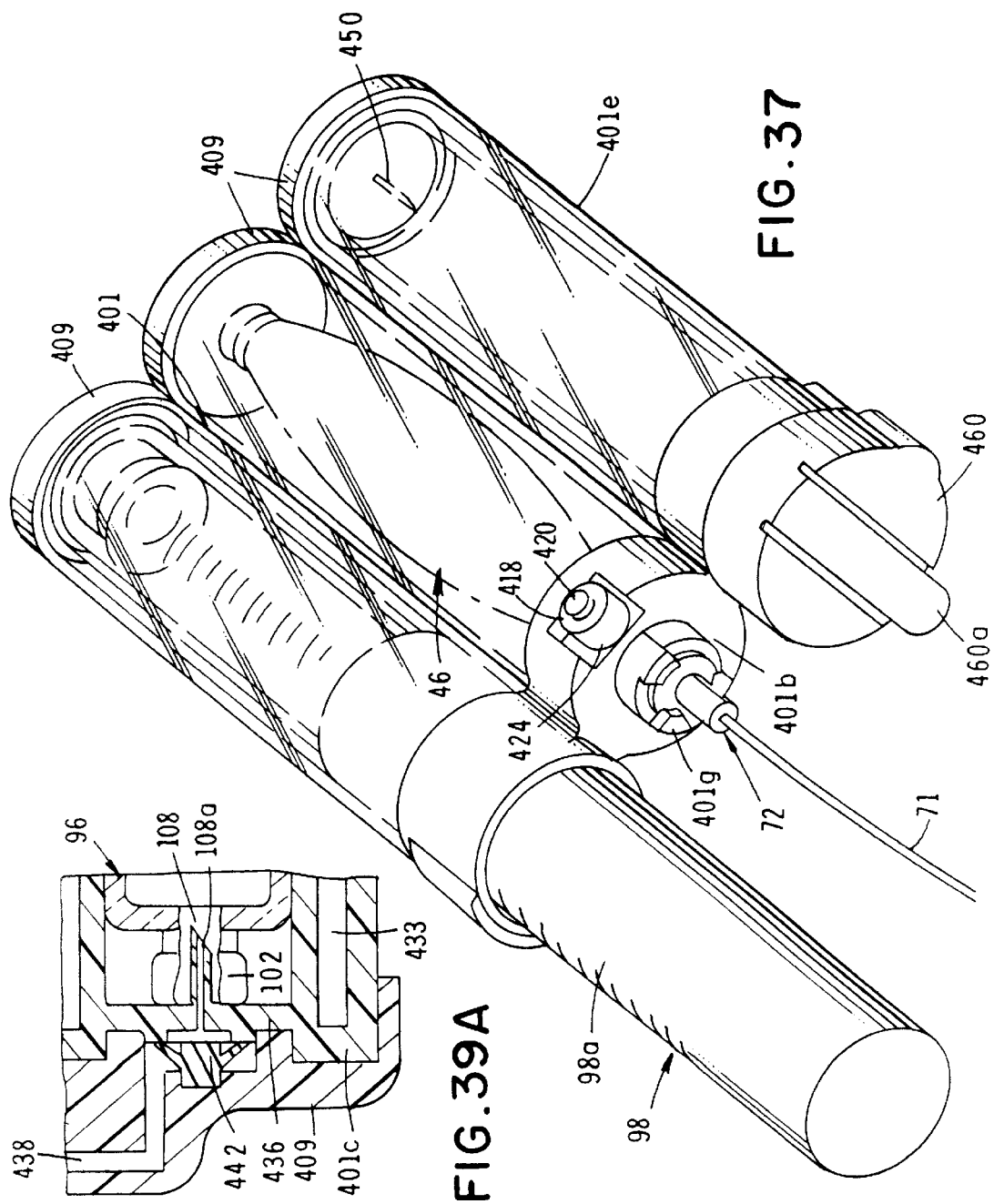

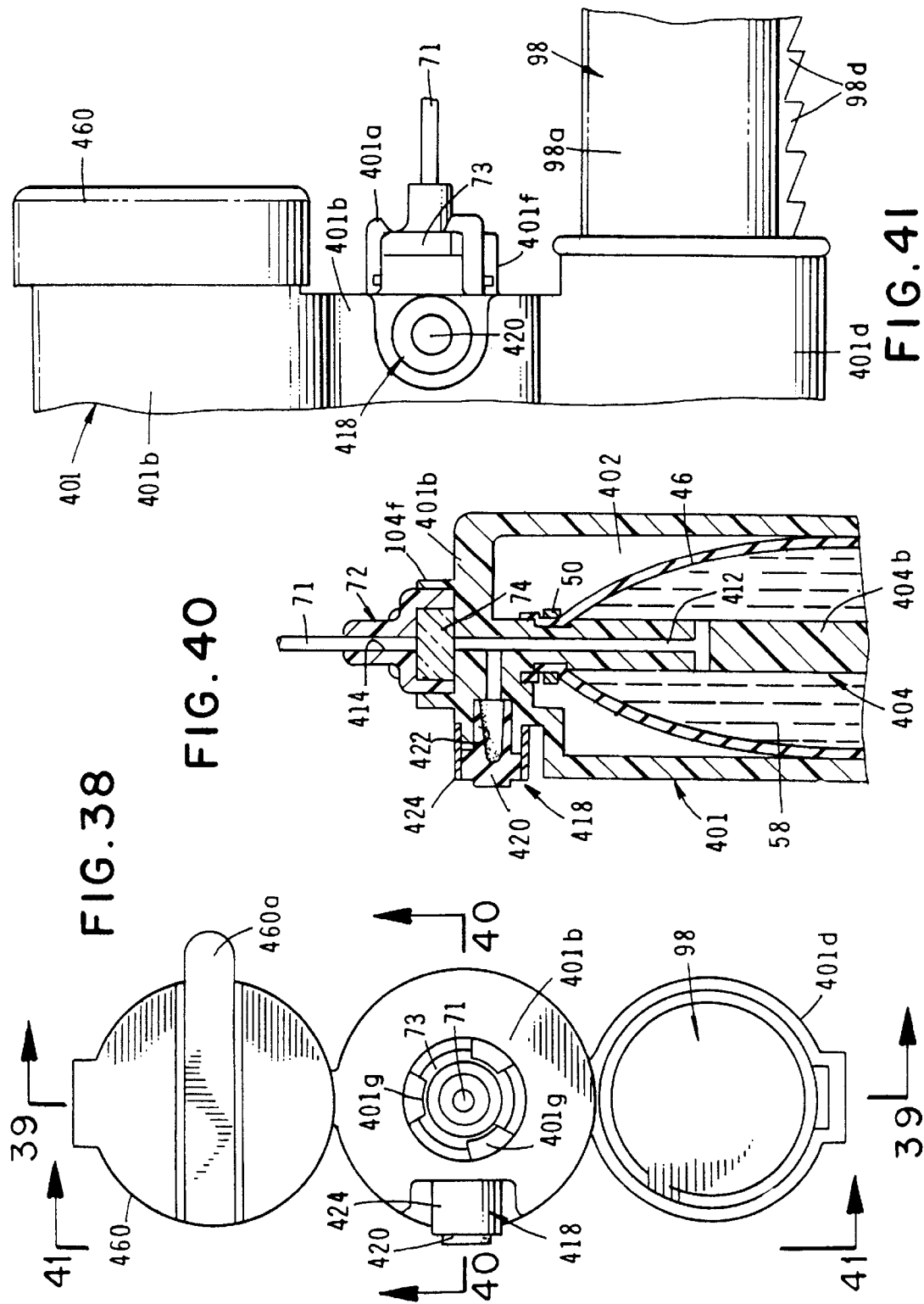

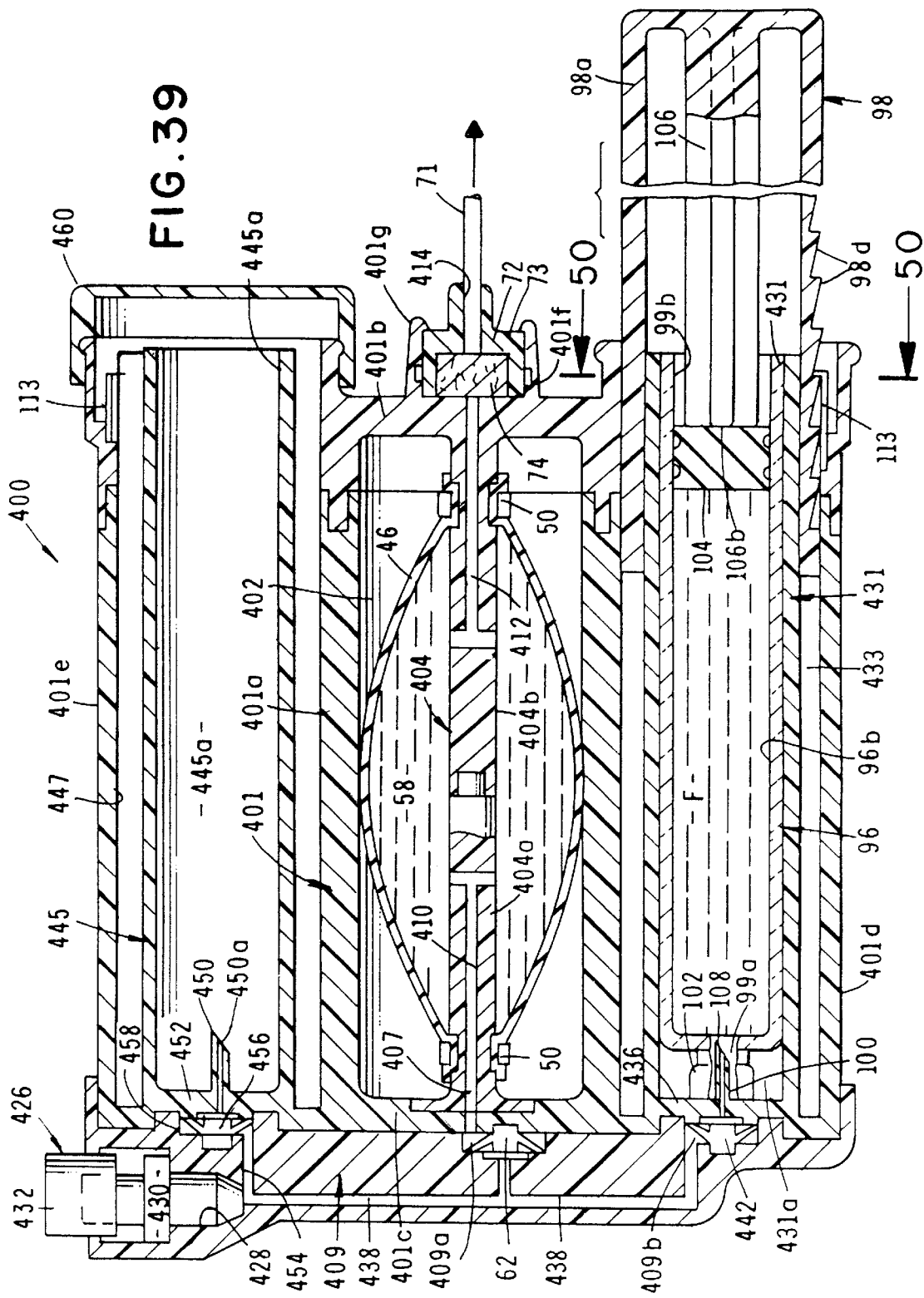

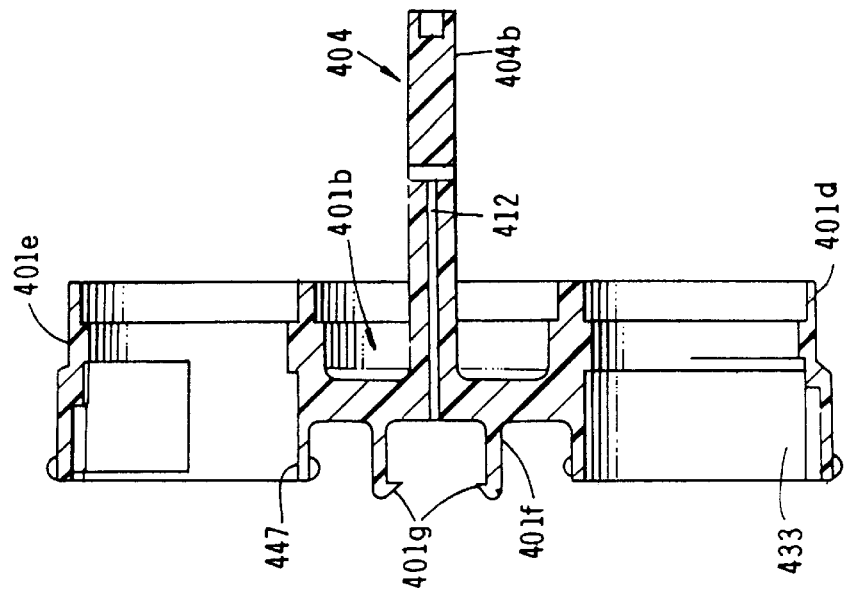
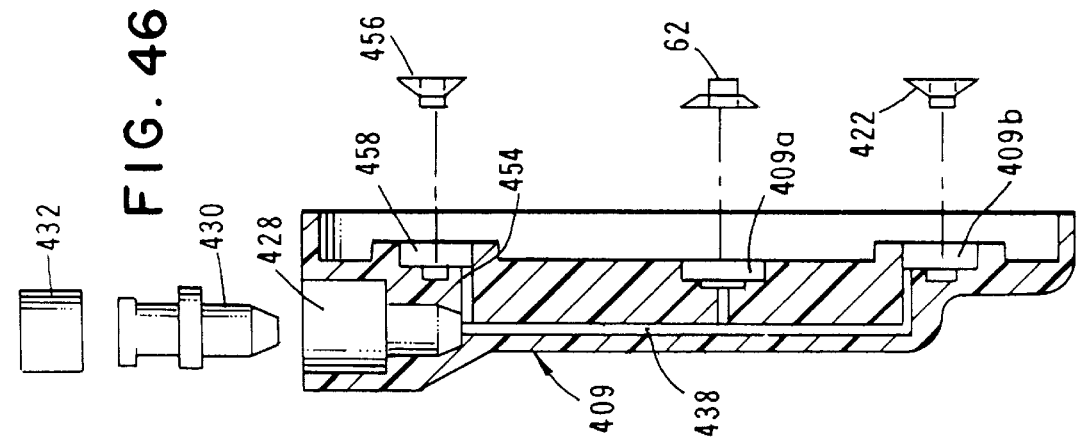

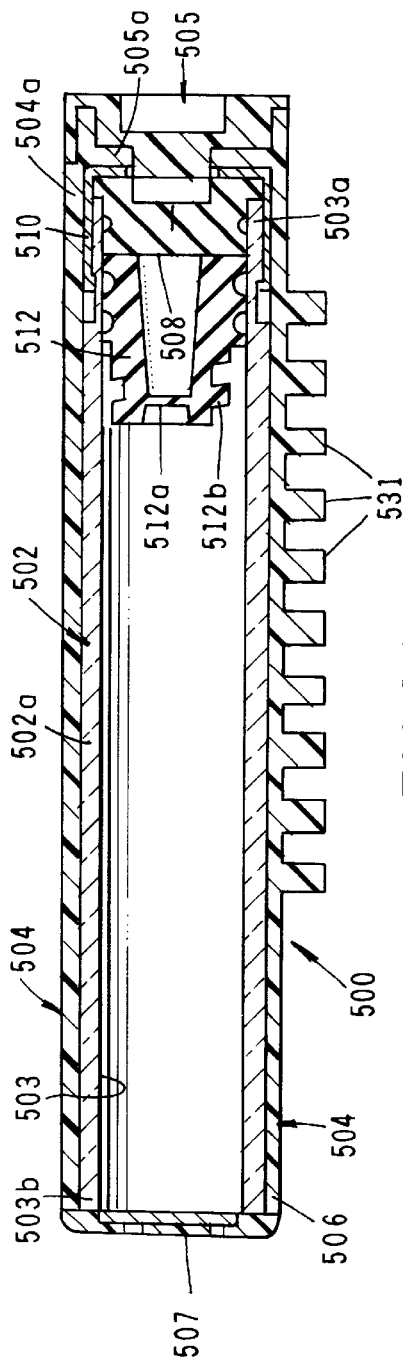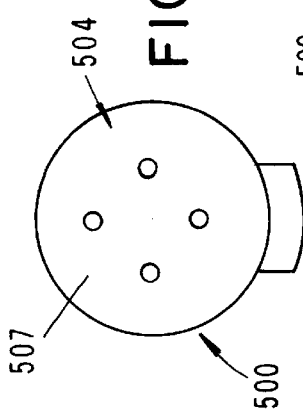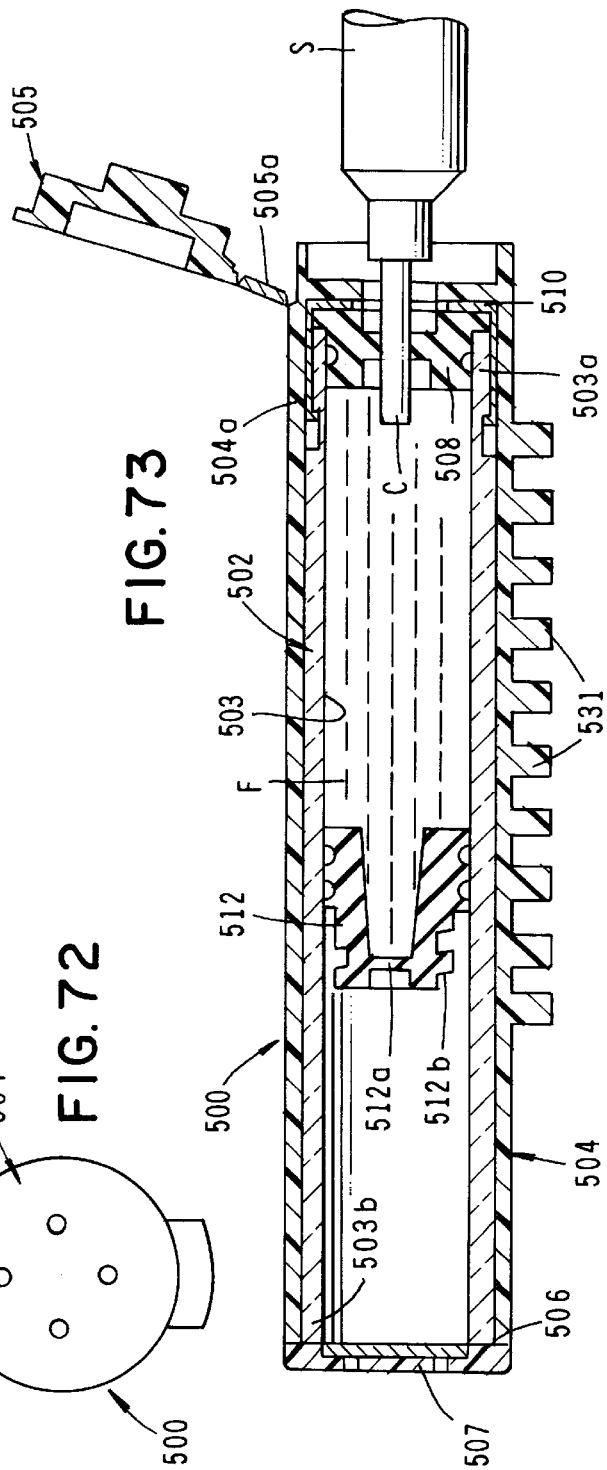

FLUID DISPENSER WITH FILL ADAPTER

This is a Continuation-In-Part Application of U.S. Ser. No. 09/165,709 filed Oct. 2, 1998; now U.S. Pat. No. 5,980,489 which is a Continuation-In-Part of U.S. Ser. No. 08/729,326 filed Oct. 15, 1996 and now issued into U.S. Pat. No. 5,873,857; which is a Continuation-In-Part of U.S. Ser. No. 08/577,496 filed Dec. 22, 1995 and now issued into U.S. Pat. No. 5,700,244; which is a Continuation-In-Part of U.S. Ser. No. 08/192,031 filed Feb. 3, 1994 and now issued into U.S. Pat. No. 5,484,415; which is a Continuation-In-Part of U.S. Ser. No. 08/156,685 filed Nov. 22, 1993 and now issued into U.S. Pat. No. 5,433,709; which is a Continuation-In-Part of U.S. Ser. No. 08/053,723 filed Apr. 26, 1993 and now issued into U.S. Pat. No. 5,354,278; which is a Continuation-In Part of U.S. Ser. No. 07/870,521 filed Apr. 17, 1992 and now issued into U.S. Pat. No. 5,263,940.

BACKGROUND OF THE INVENTION

1. Field of the Invention

The present invention relates generally to infusion devices. More particularly, the invention concerns an elastomeric bladder type infusion apparatus which is used for controllably delivering a beneficial agent to a patient. The device uniquely includes adjustable flow rate means for adjusting the rate of fluid flow from the device toward the patient.

2. Discussion of the Prior Art

Many types of infusion pumps embodying an elastomeric balloon or bladder for delivery of a quantity of pharmaceutically active material to a patient have been suggested in the past. For example, U.S. Pat. No. 4,915,693 issued to Hessel discloses an infusion pump comprising an elastomeric bladder having at least an open end, and an elongate stress member extending concentrically within the entire length of the hollow portion of the bladder and having a fluid tight seal therewith. Both a filling port and an exit port are provided in the stress member, each in fluid communication with the interior of the bladder by way of an influent and an effluent lumen, respectively. The stress member has a diameter that is greater than the relaxed internal diameter of the bladder, and has a length that exceeds the relaxed internal length of the hollow portion of the bladder, so that it prestresses the bladder in both the axial and radial directions when disposed therein, substantially filling the bladder in its unfilled state. The Hessel device also includes a one-way valve on the stress member which permits flow influent lumen only in the direction of the interior of the bladder.

Very early balloon type infusion devices are described in U.S. Pat. Nos. 3,468,308 and 3,469,578 issued to Bierman. These patents disclose a device for expelling a liquid from a bladder member at an extremely slow rate over an extended period of time.

One of the more advanced elastomeric bladder type devices ever developed is described in U.S. Pat. No. 5,354,278 issued to the present inventor. Because the present invention comprises an improvement to the devices disclosed in this latter patent, U.S. Pat. No. 5,354,278 is hereby incorporated by reference as though fully set forth herein. Another advanced elastomeric bladder type device is disclosed in U.S. Pat. No. 5,873,857 also issued to the present inventor. This patent is also incorporated by reference as though fully set forth herein.

Disclosed in U.S. Pat. No. 5,721,382, issued to the present inventors, is a device having a flow indicator means similar to that embodied in the present invention. For this reason, U.S. Pat. No. 5,721,382 is incorporated by reference as though fully set forth herein.

None of the prior art devices known to applicant have the unique capability of the present invention for precisely adjusting the rate of fluid flow from the device toward the patient using an elegantly simple, built-in, flow-rate adjustment mechanism.

SUMMARY OF THE INVENTION

It is an object of the present invention to provide an elastomeric bladder stored energy type infusion apparatus which can be filled with a medicinal fluid and after being filled, can efficiently deliver the medicinal fluid to the patient at a selected, adjustable rate.

More particularly, it is an object of the invention to provide an infusion device of the aforementioned character which includes a built-in adjustment mechanism which can be preset by the treating physician or health care worker so that the medicinal fluid stored within the device will be delivered to the patient at a precise rate.

Another object of the invention is to provide an elastomeric bladder type infusion device of the aforementioned character in which the adjustment mechanism is operable only through the use of a physician's key which following the setting of the desired flow rate can be removed and maintained within the control of the treating physician.

Another object of the invention is to provide a device of the character described in the preceding paragraphs which includes a novel indicator means for providing a visual indication of the fluid flow status through the device.

Another object of the invention is to provide an infusion device as described in the preceding paragraphs that includes a built-in dose dialing mechanism which can be preset by the treating physician or health care worker so that a precise volume of the medicinal fluid stored within the device will be delivered to the patient.

Still another object of the invention is to provide a device of the character described in the preceding paragraphs which is highly reliable, inexpensive to produce in quantity, easy to use and readily disposable after use.

BRIEF DESCRIPTION OF THE DRAWINGS

FIG. 2 is an enlarged, side-elevational, cross-sectional view of the device shown in FIG. 1.

FIG. 2A is an enlarged, cross-sectional view of the area 2A in FIG. 2.

FIG. 3 is a right end view of the device as shown in FIG. 2.

FIG. 4 is a left end view of the device shown in FIG. 2

FIG. 5 is a cross-sectional view taken along lines 5—5 of FIG. 2.

FIGS. 6A and 6B, when considered together, comprise a side-elevational, exploded view of the device shown in FIG. 2.

FIG. 7 is a generally perspective view of the closure cup of the apparatus of the invention.

FIG. 8 is a generally perspective view of the vial retaining clip of the apparatus of the invention.

FIG. 9 is a generally perspective exploded view of one form of the fluid delivery apparatus of the present invention.

FIG. 12 is an exploded, side-elevational, cross-sectional view of the forward portion of the device of FIG. 9 showing the construction of the flow rate control mechanism.

FIG. 37 is a generally perspective exploded view of still another embodiment of the fluid delivery apparatus of the present invention which includes a pair of fill vials.

FIG. 38 is a right end view of the device as shown in FIG. 37.

FIG. 39 is an enlarged, side-elevational, cross-sectional view of the device shown in FIG. 37.

FIG. 39A is an enlarged, cross-sectional view of the area designated as 39A in FIG. 39.

FIG. 40 is a cross-sectional view taken along lines 40—40 of FIG. 38.

FIG. 41 is an enlarged view taken along lines 41—41 of FIG. 38.

FIG. 46 is a cross-sectional view taken along lines 46—46 of FIG. 45.

FIG. 47 is a right-end view of the delivery end portion of the housing.

FIG. 48 is an enlarged, cross-sectional view taken along lines 48—48 of FIG. 47.

FIG. 71 is a side-elevational, cross-sectional view of one form of the fluid fill subassembly of the filling means of the invention.

FIG. 72 is a view taken along lines 72—72 of FIG. 71.

FIG. 73 is a side-elevational, cross-sectional view similar to FIG. 71 showing the field fill container being filled with fluid.

DESCRIPTION OF ONE FORM OF THE INVENTION

Figure 1:
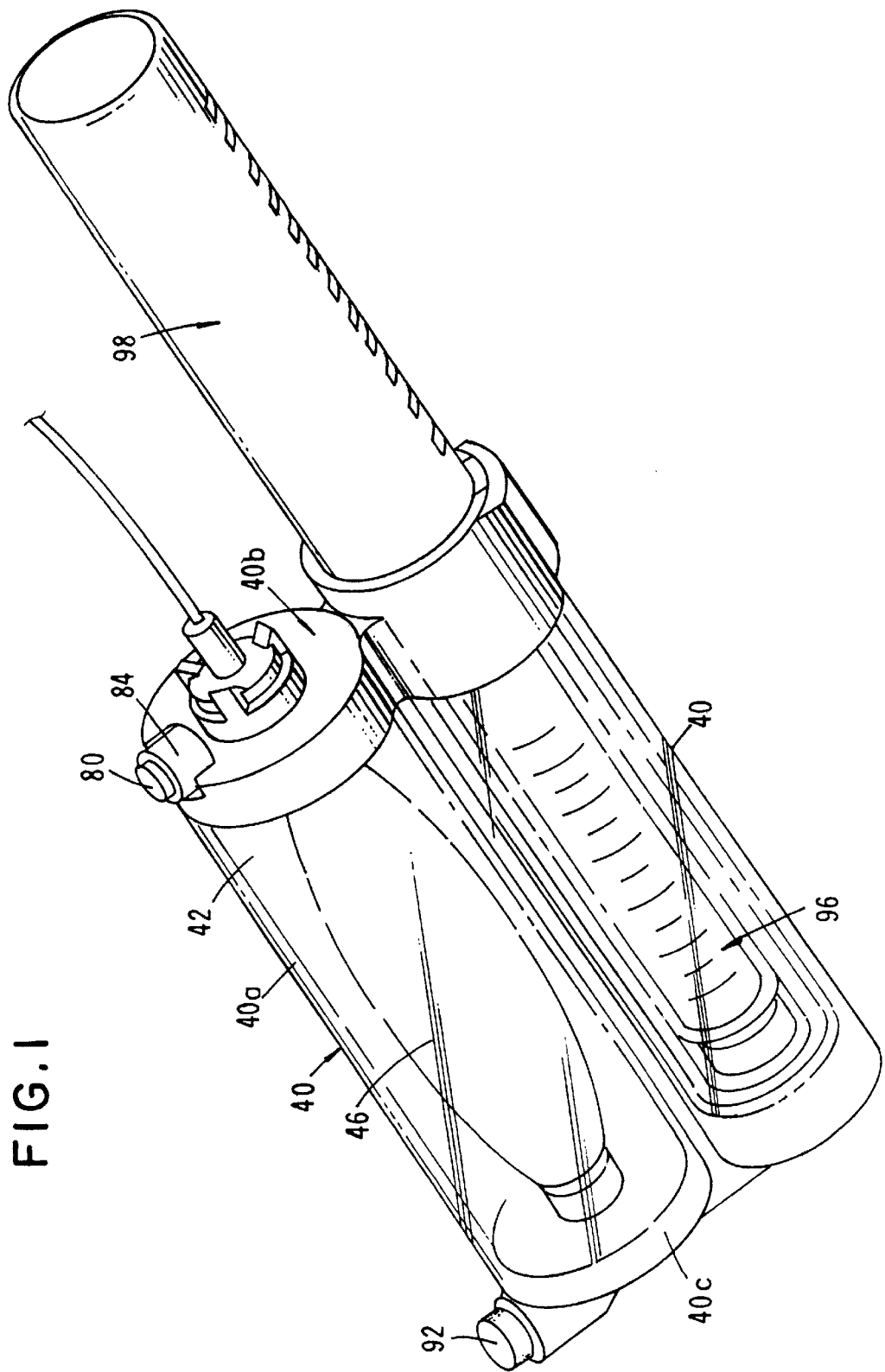
FIG. 1 is a generally perspective exploded view of one form of the fluid delivery apparatus of the present invention.

Referring to the drawings and particularly to FIGS. 1 and 2, the fluid dispenser apparatus of one form of the present invention can be seen to comprise an elongated housing 40 having a first internal chamber 42, a support 44 disposed within internal chamber 42 and extending longitudinally of the housing 40, and a generally cylindrically shaped, elongated elastomeric member 46.

Housing 40 comprises a cylindrically shaped central portion 40a and inlet and outlet end closure portions 40b and 40c respectively. Central section 40a and end portion 40b can be interconnected by any suitable means such as adhesive bonding or an appropriate sonic weldment. End portion 40c is preferably integrally formed with central portion 40a although it could be formed as a separate component. Elastomeric member 46 is securely affixed proximate its ends to support 44 by means of suitable ring clamps 50 such as self-locking plastic panduit strips.

As best seen by referring to FIG. 2, support 44 is constructed in two parts 44a and 44b which are suitably interconnected in the manner shown in FIG. 2. Part 44a has a fluid inlet 56 which is in communication with a reservoir 58 formed by elastomeric member 46 and support 44 via a fluid passageway 60. Valve means, shown here as a check valve 62 which is disposed within a chamber formed in end portion 40c, permits fluid flow in a direction toward reservoir 58 but blocks fluid flow in the opposite direction.

Second part 44b of support 44 has an outlet passageway 66 which communicates with the delivery means of the invention for delivering fluid to the patient. The delivery means includes a fluid delivery passageway 70 formed in a quick disconnect assembly which includes a housing 72. In a manner presently to be described, the quick disconnect assembly can be readily releasably interconnected with end portion 40b of housing 40. Fluid delivery passageway 66 communicates with reservoir 58 and also with passageway 70 via a flow rate control means, here provided as a porous rate control frit 74 which is mounted within quick disconnect housing 72 and which controls the rate of fluid flow toward the delivery means.

An important feature of the apparatus of the present invention is the provision of sampling means for sampling and retrival of fluid contained within reservoir 58. This sampling means here includes a sampling port assembly 78 provided in end portion 40b of support 40. Sampling port assembly 78 includes a septum 80, which is received within a chamber 82 formed in housing end portion 40b, and a clamping ring 84 for clamping the septum in place within chamber 82. Through use of the sampling means such as a conventional syringe, the contents of reservoir 58 can be sampled at any time and, after the delivery step, any medicament remaining in the reservoir can be retrieved for subsequent use.

Formed in end portion 40c of housing 40 is a first fill means for filling reservoir 58 with a diluent such as a saline solution or with any other desired fluid. This first fill means here comprises a first fill port assembly 86 which includes a chamber 88 formed in end portion 40c of housing 40. Sealably disposed within chamber 88 is a conventional male luer connector 90 which can be suitably connected with a conventional female luer connector and fill line (not shown). A conventional luer cap 92 sealably closes connector 90 when it is not in use. If desired, connector 90 can include a conventional check valve to permit fluid flow toward reservoir 58 but to block flow in the opposite direction. With a suitable female luer connector, connected to connector 90 and with the fill line connected to a source of diluent, reservoir 58 can be partially filled in a manner well understood by those skilled in the art.

Turning particularly to FIGS. 1, 2, and 6, the important second fill means of the invention for adding fluid to reservoir 58 is there illustrated. This second fill means here comprises a container subassembly 96, and an adapter subassembly 98, the character of which will presently be described. Container subassembly 96 includes a body portion 96a having a fluid chamber 96b (FIG. 2) for containing a medicament or other fluid "F" which is desired to be added to the diluent or other fluid contained within reservoir 58. Fluid chamber 96b provided with first and second open ends 99a and 99b. First open end 99a is sealably closed by closure means here provided in the form of a pierceable septum assembly 100 (FIG. 2), which is held securely in position by a clamping ring 102. A plunger 104 (FIG. 2) is telescopically movable within chamber 96b of container subassembly 96 from a first location proximate first open end 99b to a second position proximate second open end 99a. The vial portion of the container subassembly 96 can be constructed of various materials such as glass and plastic.

The previously mentioned adapter subassembly 98 comprises a hollow housing 98a having a first open end 98b (FIG. 6) and a second closed end 98c (FIG. 2). Container subassembly 96 is telescopically receivable within open end 101a of a vial receiving tube 101 which, in turn, is disposed within an elongated, generally cylindrically shaped chamber 103 formed in the lower portion 40d of housing 40. With this construction, hollow housing 98a can be moved from the extended position shown in FIG. 2 into a vial encapsulation position wherein the vial resides interiorly of the adapter subassembly. Forming an important part of adapter subassembly 98 is pusher means shown here as an elongated pusher rod 106 which functions to move plunger 104 longitudinally of fluid chamber 96b. In the form of the invention shown in the drawings, pusher rod 106 has a first end 106a interconnected with the closure wall 98c of housing 98 and an opposite end 106b which engages plunger 104 and causes telescopic movement of the plunger within chamber 96b of container subassembly 96 as housing is moved within an annular space 107 formed between vial receiving tube 101 and the outer wall of chamber 103 of device portion 40d.

As best seen in FIG. 2A, a hollow piercing cannula 108 is connected to support wall 110a formed on a vial receiving tube 110. Cannula 108 extends into receiving chamber 101a formed in vial receiving tube 101 in the manner shown in FIGS. 2A and 6A. A passageway 111 formed in end portion 40c communicates with the fluid passageway 108a of hollow cannula 108 via a check valve 112, which is mounted within a chamber 40e formed in housing 40. Check valve 112 permits fluid flow from vial reservoir 96b, into passageway 111 and then into inlet passageway 60 and then finally into reservoir 58. However, check valve 112 effectively blocks fluid flow into the opposite direction.

In using the apparatus of the invention, reservoir 58 is initially filled by the first fill means or assembly 86, with a diluent or other fluid. This done, container subassembly 98 is mated with the adapter subassembly 96 by first telescopically inserting the container subassembly into vial receiving tube 101. Next, a tear-away closure cap 103a, which seals chamber 103 of lower housing 40d, is removed (FIGS. 6B and 7). This done, housing 68 of adapter the assemblage can be pushed forwardly within annular space 107. As the adapter subassembly moves forwardly, pusher rod 106 will engage plunger 104 causing the container assembly to also move forwardly. As the container assembly approaches a seated position, piercing cannula 108 will pierce septum assembly 100 of the container assembly. Once the fluid flow path between the hollow cannula and the fluid reservoir 58 is thus created via passageways 111 and 60, a continued inward movement of the adapter subassembly 88 will cause pusher rod 106 thereof to move plunger 104 forwardly of chamber 96b. As plunger 104 is moved forwardly, the medicament or other fluid contained within chamber 96b of vial 96 will flow through passageway 108a of the hollow cannula, past check valve 112, into passageway 111 and then into fluid reservoir 58 where it will intermix with the diluent or other fluid contained within the reservoir.

During the initial filling of the reservoir using the first fill means, membrane 46 will have been distended outwardly in the manner shown in FIG. 2 wherein the central portion thereof is spaced from support 40. Rings 50 which are in clamping engagement with support 44 function to seal the membrane against the end portions of the support and prevent leakage of fluid between the membrane and the support. As the distendable membrane expands outwardly, the displaced air within housing 60 will be vented to atmosphere via vent means "V" provided in housing 40.

After the medicament or other fluid contained within vial 96 has been added to fluid reservoir 58 using th e second fill means, the apparatus will remain in this filled condition until the outlet flow path of the device is opened. Following opening of the outlet flow path, the stored energy means or membrane 46 will tend to return to a less distended condition causing fluid to flow outwardly of the apparatus via passageway 66, through rate control frit 74 and finally outwardly of the device via delivery passageway 70. To interconnect passageway 70 with the patient, a conventional infusion set including a delivery line 71 is connected to connector 72 in the manner shown in FIG. 2. In this regard, it is to be noted that connector 72 includes a body portion 72a having a shoulder 73 and a hollow stem portion 72b which sealably receives delivery tube 71 (see FIG. 6B).

End portion 40b of the device housing includes a hollow, generally cylindrically shaped housing 41 which is provided with a yieldably deformable, hook-like locking tabs 41a (see also FIG. 4). Tabs 41a, which are constructed from a yieldably deformable plastic, lockably receive shoulder 73 of body portion 72b in the manner shown in FIG. 2 so as to releasably secure connector 72 within housing 41 of end portion 40b.

Materials suitable for use in constructing housing 40 and support 44 include metals, rubber or plastics that are compatible with the liquids they contact and are preferably non-allergenic type material. Examples of such materials are: stainless steel, aluminum, latex rubber, butyl rubber, nitrile rubber, polyisipreme, styrenebutadiene copolymer, silicones, ployolefins such as polypropylene and polyethylene, polyesters, polyurethane, polyamides and polycarbonates. Manufactures of suitable materials for use in constructing the fluid dispensing assembly of the invention includes: Dow Corning of Midland, Mich.; General Electric of Scenectady, N.Y.; and Shell Chemical Company of Houston, Tex.; DuPont Chemical of Wilmington, Del.; and Eastman Chemical of Kingsport, Tenn.

In order to securely lock the adapter subassembly 98 within support 44 after the reservoir has been filled, novel locking means are provided. The locking means here comprises a series of locking teeth 98d. As indicated in FIG. 2, these locking teeth are constructed so that as the adapter subassembly 98 is moved inwardly they will slide under a flexible locking tab 113a formed on a clip 113 (FIGS. 2 and 8) which is disposed proximate the entrance of receiving chamber 103. However, once the adapter subassembly has reached the fully forward position shown in FIG. 2, locking tab 40e will engage one of the teeth 96d and effectively prevent removal of the adapter subassembly from passageway 107. With this novel construction, once the reservoir 58 has been filled with the fluid "F" contained in the container subassembly, the adapter assembly cannot be removed from the fluid dispensing device and, thereby preventing system adulteration.

Turning next to FIGS. 9 through 26, an alternate form of the fluid dispenser apparatus of the present invention is there shown. This latest embodiment comprises an elongated housing 112 having an internal chamber 114, a support 116 disposed within internal chamber 114 and extending longitudinally of the housing 112 and a generally cylindrically shaped, elongated elastomeric member 118.

Housing 112 comprises a cylindrically shaped central portion 112a and inlet and outlet end plates 112b and 112c respectively. Central section 112a and end plates 112b and 112c may be interconnected by any suitable means such as adhesive bonding or an appropriate sonic weldment. Elastomeric member 118 is securely affixed proximate its ends to support 116 by means of suitable ring clamps 120 such as self-locking plastic panduit strips.

Figure 10:
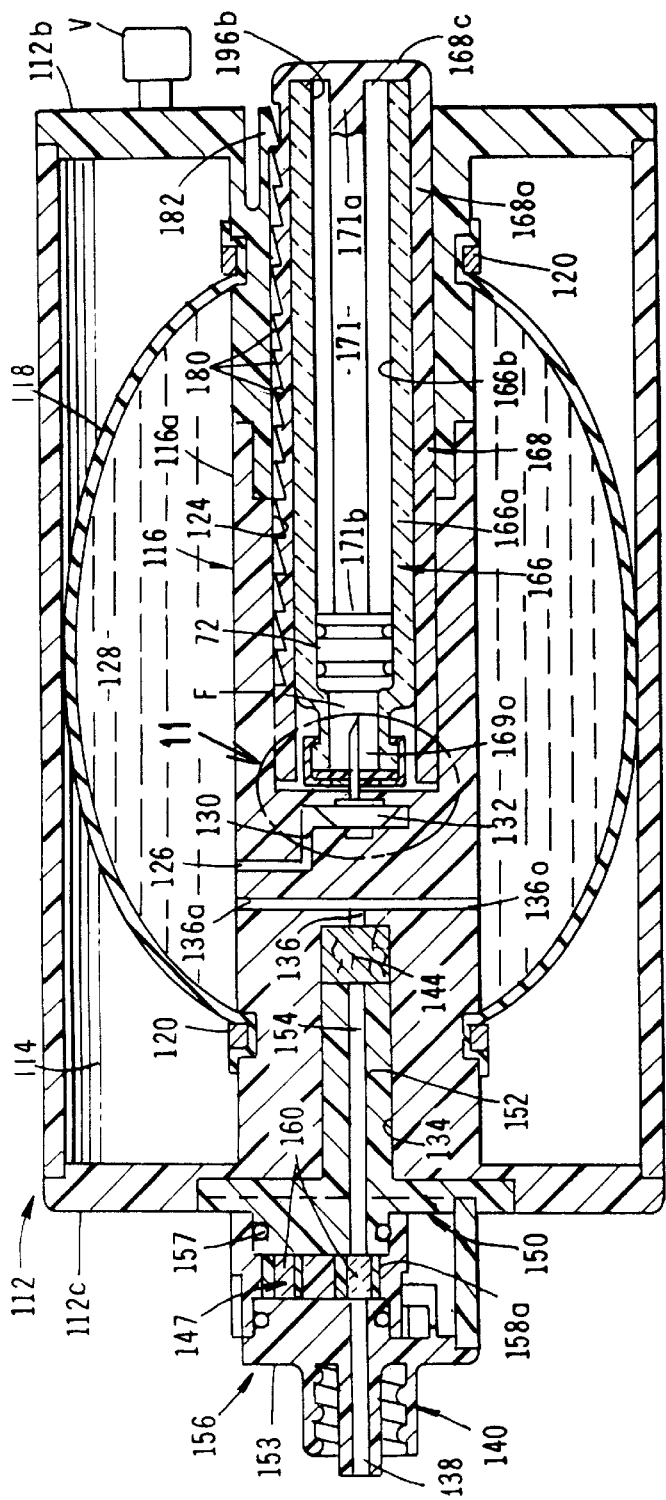
FIG. 10 is an enlarged, side-elevational, cross-sectional view of the device shown in FIG. 9.

As best seen by referring to FIG. 10, support 116 is provided with a first elongated receiving chamber 124. A fluid passageway 126 which, in a manner presently to be described, is in communication both with chamber and with a reservoir 128. Reservoir 128 is uniquely formed by elastomeric member 118 and the central portion 116a of support 116 and communicates with passageway 126 via a fluid passageway 130 formed in support 116. Valve means, shown here as a check valve 132, which is carried within a chamber formed in support 116, permits fluid flow toward reservoir 128 but blocks fluid flow in the opposite direction.

Support 116 is also provided with a second downstream chamber 134 which has an inlet passageway 136 that communicates with reservoir 128 via passageways 136a formed in support 116. Chamber 134 is in communication with the fluid dispensing means of the invention which includes a fluid delivery passageway 138 formed in a luer connector 140 that is provided at the outlet end of support 116. As indicated in FIG. 10, fluid delivery passageway 138 of the fluid dispensing means communicates with reservoir 128 via a filter means and the previously identified passageways 136 and 136a. The filter means here comprises a porous filter element 144 of conventional construction and functions to filter out any particulates contained within the fluid to be delivered to the patient.

Figure 11:
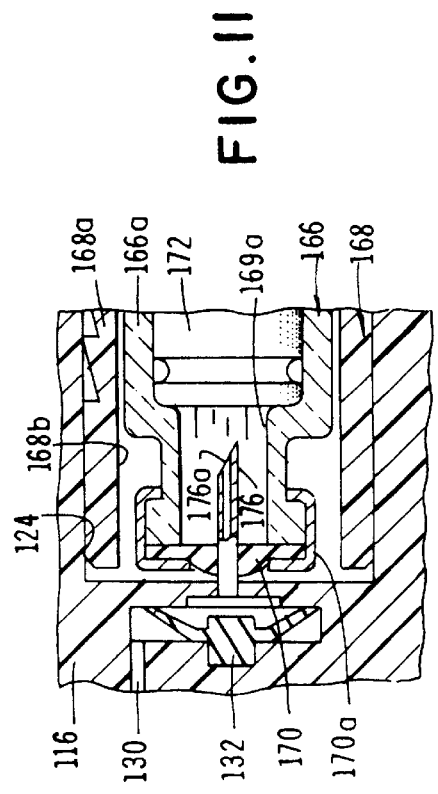
FIG. 11 is an enlarged, fragmentary, cross-sectional view of the area designated as 11 in FIG. 10.
Figure 13:
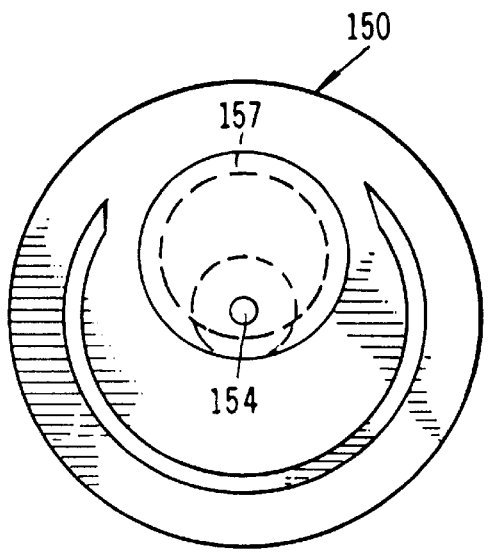
FIG. 13 is a view taken along lines 13—13 of FIG. 12.
Figure 14:
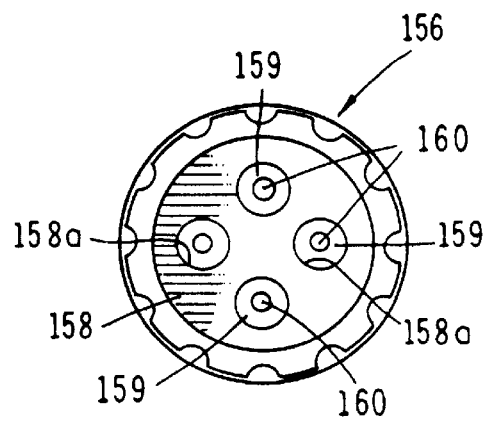
FIG. 14 is a view taken along lines 14—14 of FIG. 12.

An extremely important feature of the apparatus of the present invention is the flow rate control means for adjustably controlling the rate of fluid flow from the reservoir of the apparatus to the delivery passageway 138. This novel means here comprises an adjustable rate control mechanism 147 which is carried by housing 112. As best seen in FIG. 11, mechanism 147 includes a body portion 150 having an elongated stem 152 which is receivable within second chamber 134 of support 116 and a forward portion 153 which includes luer like connector 140. Body portion 150 also includes a fluid passageway 154 which is in communication with both inlet passageway 136 and fluid delivery passageway 138. Rotatably carried intermediate forward portion 153 and body portion 150 is a control knob 156. O-rings 157 carried by portions 147 and 150 sealably engage control knob 156 and prevent leakage among the various cooperating components.

Mounted within control knob 156 and rotatable therewith is a control member 158. As shown in FIG. 12, control member 158 carries a plurality of circumferentially spaced apart flow restrictors each of which can be selectively moved into index with flow passageway 154 of body 150 by rotating knob 156 relative to body portion 150. In the embodiment of the invention shown in FIGS. 9 through 14, the flow restrictors are provided in the form of rate control frits 160 (see FIGS. 10 and 12), which are secured in place within apertures 158a formed in member 158 by a moldable elastomer 169 (see FIG. 12). With the construction shown, by rotating knob 156 relative to body portion 150, each of the rate control frits 160 can be moved sequentially into alignment with passageway 154. Because each of the frits 160 is of a different, preselected porosity, it is apparent that the rate of fluid flowing outwardly of the device through delivery passageway 138 can be precisely controlled by positioning a particular frit in the flow path.

Figure 15:
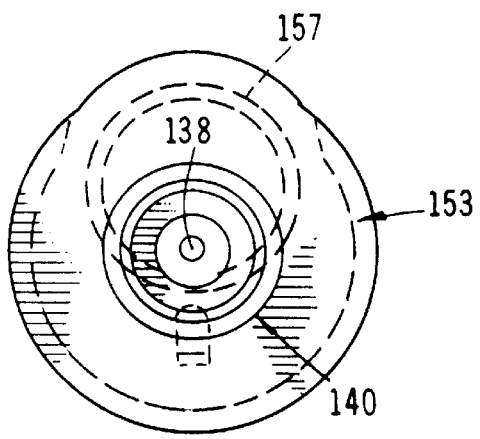
FIG. 15 is a view taken along lines 15—15 of FIG. 12.
Figure 16:
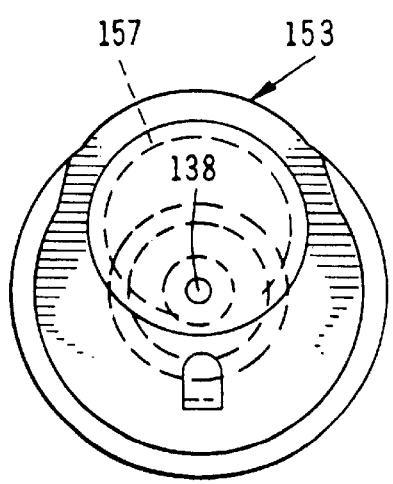
FIG. 16 is a view taken along lines 16—16 of FIG. 12.
Figure 17:
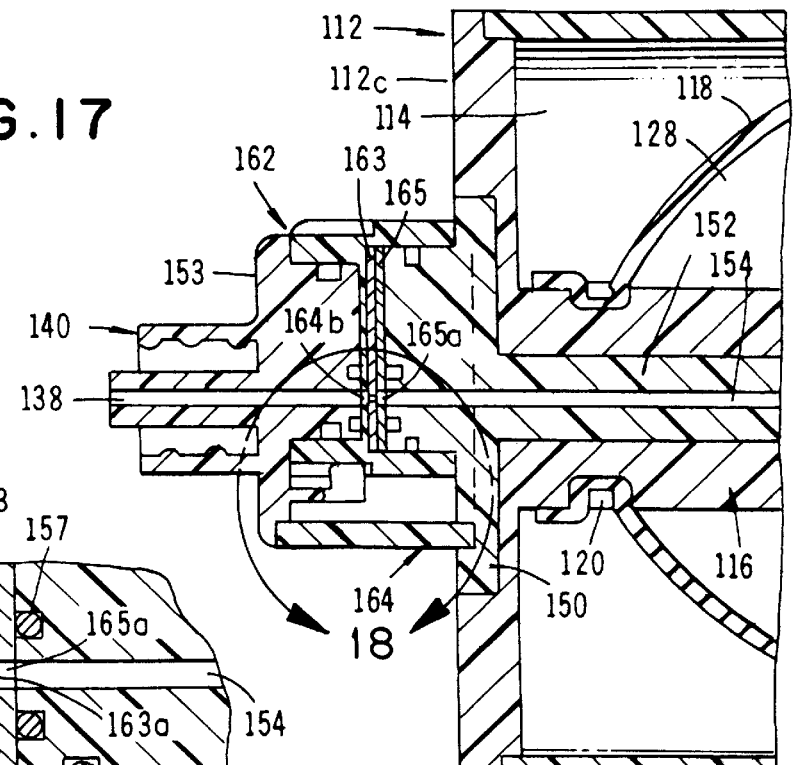
FIG. 17 is an enlarged, fragmentary, cross-sectional view of the forward portion of an alternate form of the apparatus of the invention showing an adjustable flow rate control mechanism of a slightly different construction embodying a plurality of novel, laser drilled microbore rate control wafers.
Figure 18:
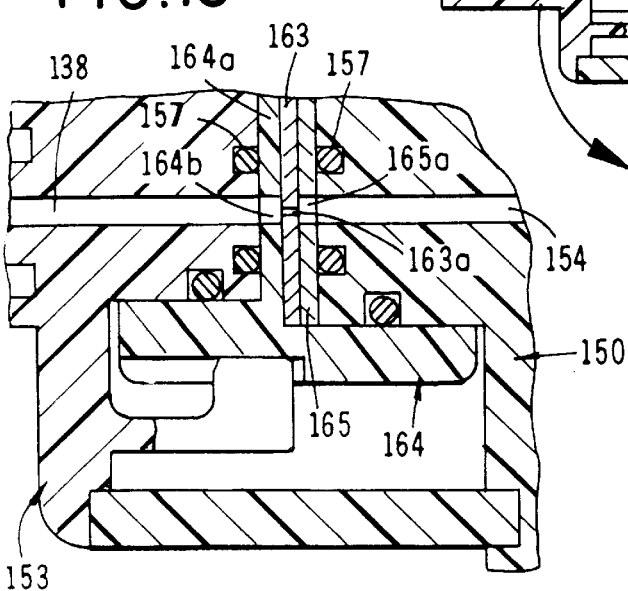
FIG. 18 is an enlarged fragmentary, cross-sectional view of the area designated as 18 in FIG. 17.
Figure 19:
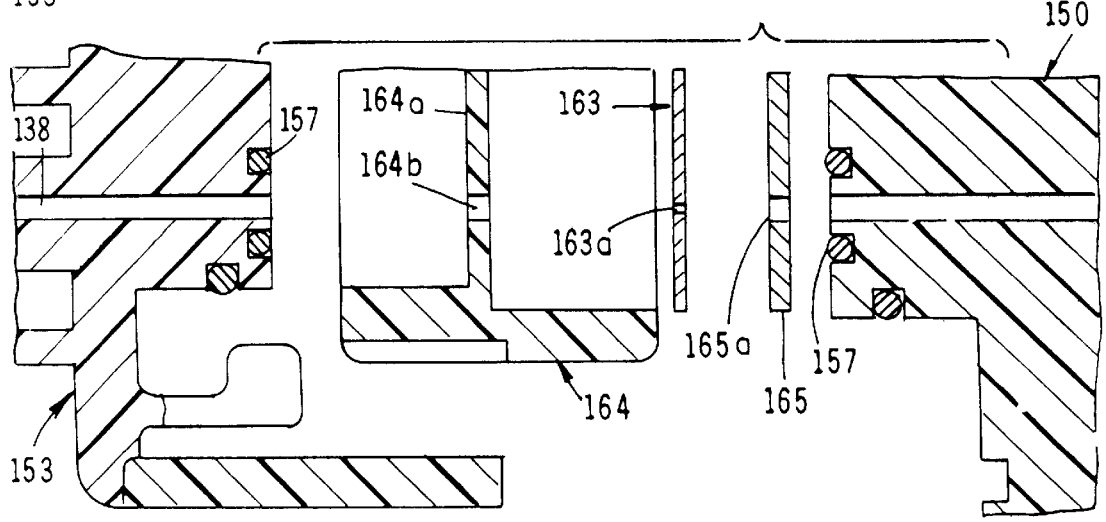
FIG. 19 is an enlarged, cross-sectional, exploded view of the flow control mechanism of the apparatus shown in FIG. 18.

Turning to FIGS. 15 through 17, an alternate form of rate control mechanism 162 is there shown. This rate control mechanism is similar in many respects to mechanism 147 and like numerals are used to identify like components. The major difference between mechanisms 147 and 162 resides in the differently configured control member 163 which here comprises a thin wafer having circumferentially spaced, laser-drilled microbores 163a (FIG. 17). Member 163 is carried by a slightly different control knob 164 which includes a central wall 164a which supports one face of member 163. The other face of member 163 is supported by a spacer wall 165 which abuts body portion 150 which is of the general configuration previously described. Members 163 and 165 are provided with indexable apertures 163a and 165a respectively, which align with fluid passageway 154 of member 150. By rotating control knob 164, a selected core of the laser drilled microbores 163a can be moved into alignment with apertures 163a and 165a. by selecting an aperture of a particular size, the rate of fluid flow toward outlet passageway 138 can be precisely controlled.

Turning once again to FIG. 10, the important fill means of the present form of the apparatus comprises a container subassembly 166, and an adapter subassembly 168, the character of which will presently be described. Container subassembly 166 includes a body portion 166a having a fluid chamber 166b for containing an injectable fluid "F". Fluid chamber 166b is sealably closed by closure means here provided in the form of a pierceable septum assembly 170 (FIG. 10A). Septum assembly 170 is held securely in position by clamping ring 170a. A plunger 172 is telescopically movable within chamber 166b of container subassembly 166 from a first location proximate first open end 169b to a second position proximate second open end 169a. The vial portion of the container subassembly 166 can be constructed of various materials such as glass and plastic.

Adapter subassembly 168 comprises a hollow housing 168a having a first open end 168b (FIG. 11) and a second closed end 168c (FIG. 10). Container subassembly 166 is telescopically receivable within open end 168b in the manner shown in FIGS. 10 and 11 so that the housing can be moved from an extended position into the vial encapsulation position shown in FIG. 10. Forming an important part of adapter subassembly 168 is pusher means shown here as an elongated pusher rod 171 which functions to move plunger 172 within fluid chamber 166b from a first extended position to the intermediate position shown in FIG. 10. In the form of the invention shown in the drawings, pusher rod 171 has a first end 171a interconnected with the closure wall of housing 168a and an opposite end 171b which engages plunger 172 and causes telescopic movement of the plunger within chamber 166b of container subassembly 166 as housing 168a is moved from the extended position into the vial encapsulating position shown in FIG. 10.

As best seen in FIG. 11, hollow piercing cannula 176 is connected to support 116 proximate receiving chamber 124 so that it extends into receiving chamber 124 a limited distance. Passageway 130 communicates with the fluid passageway 176a of hollow cannula 176 via check valve 132 to enable fluid to flow from vial 166a through the filter means and then outwardly of the device through outlet passageway 138. The filter means, which here comprises filter 144, can be constructed from a wide variety of materials, but a material comprising polysulfone sold by Gelman Sciences under the name and style of SUPOR has proven satisfactory for the purpose.

In using the apparatus of the invention, mating of the container subassembly 166 with the adapter subassembly 168 is accomplished by a telescopically inserting the container subassembly into open end 168b of housing 168. This done, the assemblage thus formed is pushed forwardly of chamber 124. As the adapter subassembly approaches a seated position, cannula 176 will pierce septum assembly 170. Once the fluid flow path between the hollow cannula and the fluid reservoir 128 is thus created via passageway 126 and 130, a continued inward movement of the adapter subassembly 188 will cause plusher rod 171 to move plunger 172 forwardly of chamber 166b. As plunger 172 is moved forwardly of chamber 166b, fluid contained within the chamber will flow through passageway 176b of the hollow cannula, past check valve 132, into passageway 130, into passageway 126, and then into fluid reservoir 128. As the fluid under pressure flows into reservoir 128, membrane 118 will be distended outwardly in the manner shown in FIG. 10 wherein the central portion thereof is spaced from support 116. Rings 120 which are in clamping engagement with support 116 function to seal the membrane against the end portions of the support and prevent leakage of fluid between the membrane and the support. As the distendable membrane expands outwardly, the displaced air within housing 160 will be vented to atmosphere via vent means "V" provided in end plate 112b.

Once distendable membrane 118 is distended to form fluid reservoir 128, the apparatus will remain in this filled condition until outlet passageway 138 of the luer-like connector assembly 140 is opened. With outlet passageway 138 opened, the stored energy means or membrane 118 will tend to return to a less distended condition causing fluid to flow outwardly of the apparatus via passageway 130, through filter 144, then through passageway 154 and finally outwardly of the device via delivery passageway 138.

Materials suitable for use in constructing housing 112 and support 116 include metals, rubber or plastics that are compatible with the liquids they contact and are preferably non-allergenic type material. Examples of such materials are: stainless steel. Aluminum, latex rubber, butyl rubber, nitrile rubber, polyisipreme, styrenebutadine copolymer, silicones, polyolefins such as polypropylene and polyethylene, polyesters, polyurethane polyamides and polycarbonates. Manufactures of suitable materials for use in constructing the fluid dispensing assembly of the invention includes: Dow Corning of Midland, Mich.; General Electric of Scenectady, N.Y.; and Shell Chemical Company of Houston, Tex.; DuPont Chemical of Wilmington, Del.; and Eastman Chemical of Kingsport, Tenn.

In order to securely lock the adapter subassembly 168 within support 116 after the reservoir has been filled, novel locking means are provided. Tile locking means here comprises a series of locking teeth 180. As indicated in FIG. 10, there locking teeth are constructed so that as the adapter subassembly 168 is moved inwardly they will slide under a flexible locking tab 182, which is provided proximate the entrance of receiving chamber 124. However, once the adapter subassembly has reached the fully forward position shown in FIG. 10, locking tab 182 will engage one of the teeth 180 and effectively prevent removal of the adapter subassembly from passageway 124. With this novel construction, once the reservoir 128 has been filled with the fluid "F" contained in the container subassembly, the adapter assembly cannot be removed from the fluid dispensing device thereby preventing system adulteration.

Figure 20:
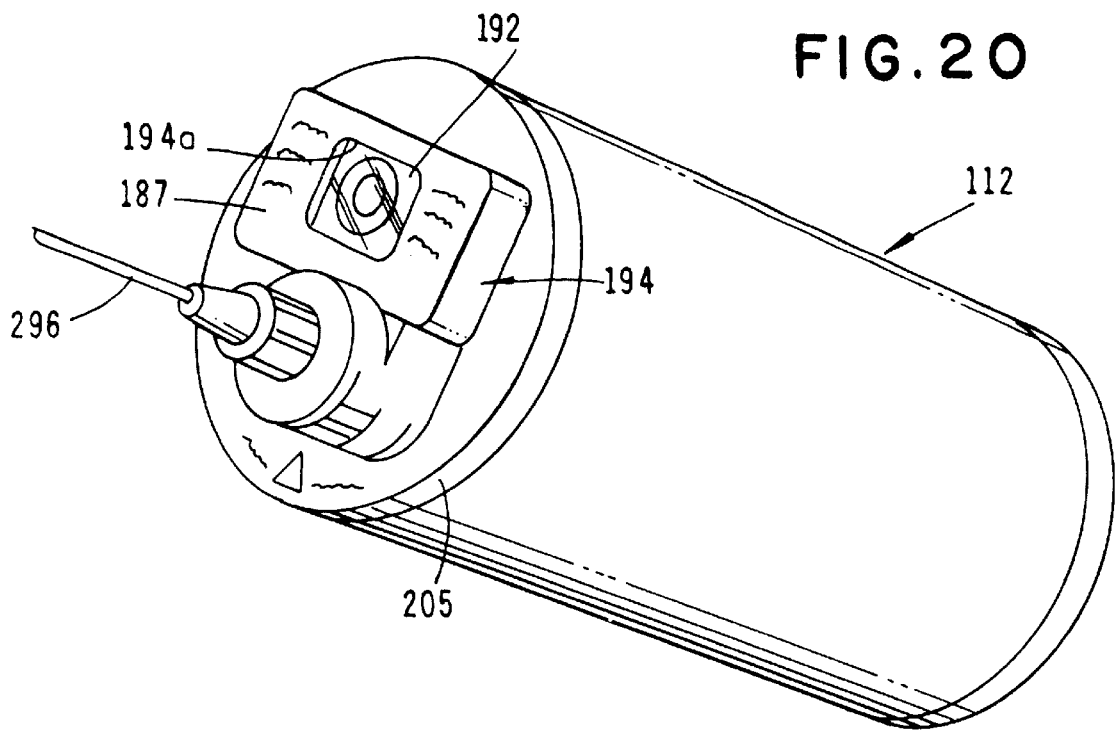
FIG. 20 is a generally perspective view of an alternate form of the apparatus of the invention which includes indicator means for visually indicating fluid flow through the device.
Figure 23:
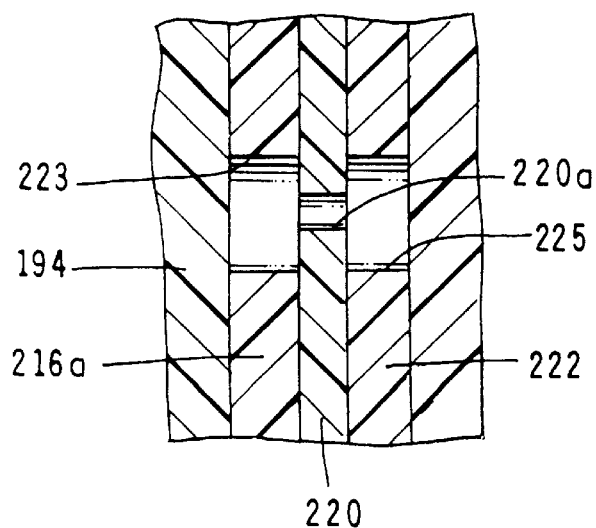
FIG. 23 is an enlarged, cross-sectional view of the area designated as 23 in FIG. 22.
Figure 21:
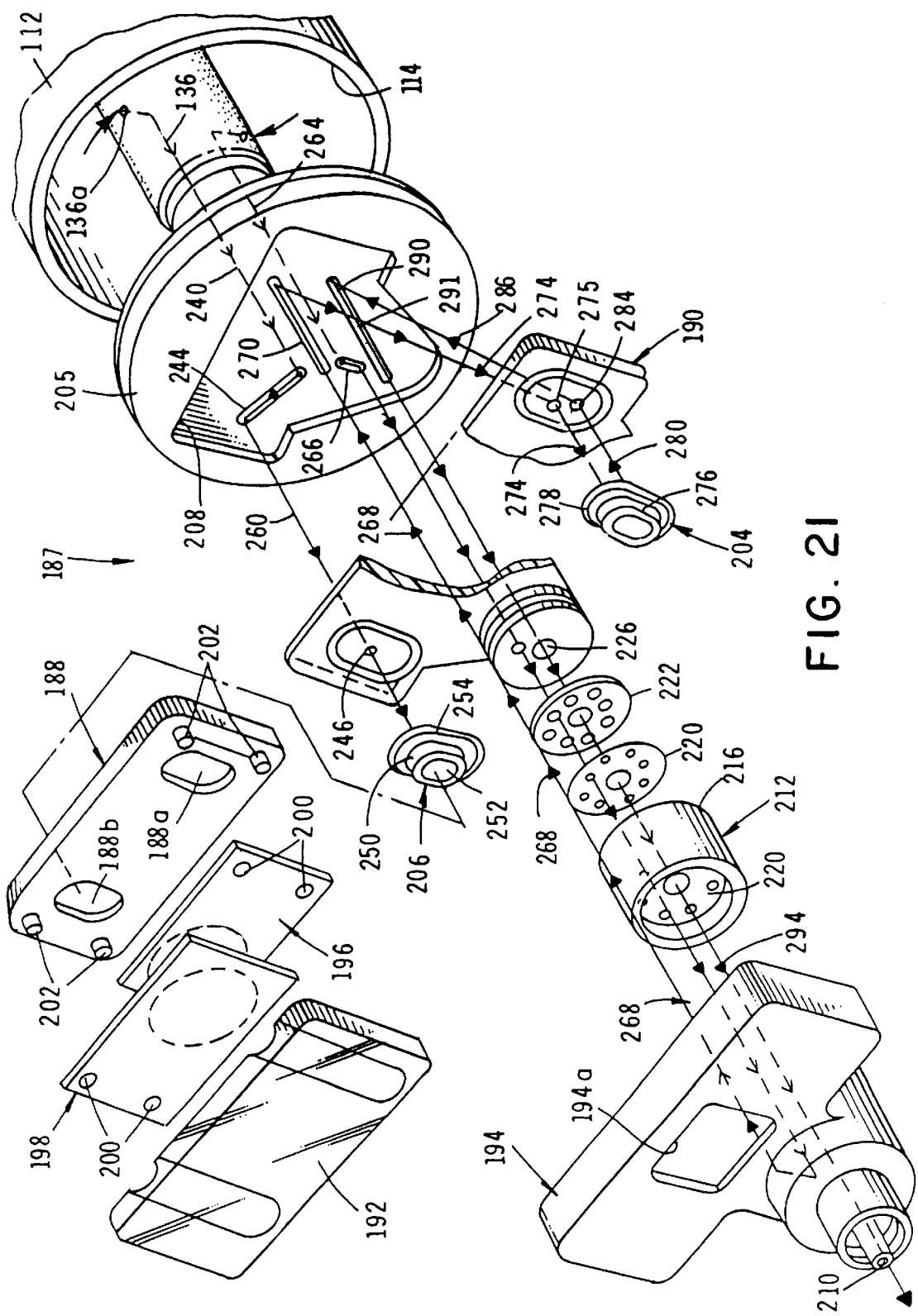
FIG. 21 is a generally perspective, exploded view of tile apparatus shown in FIG. 20.
Figure 22:
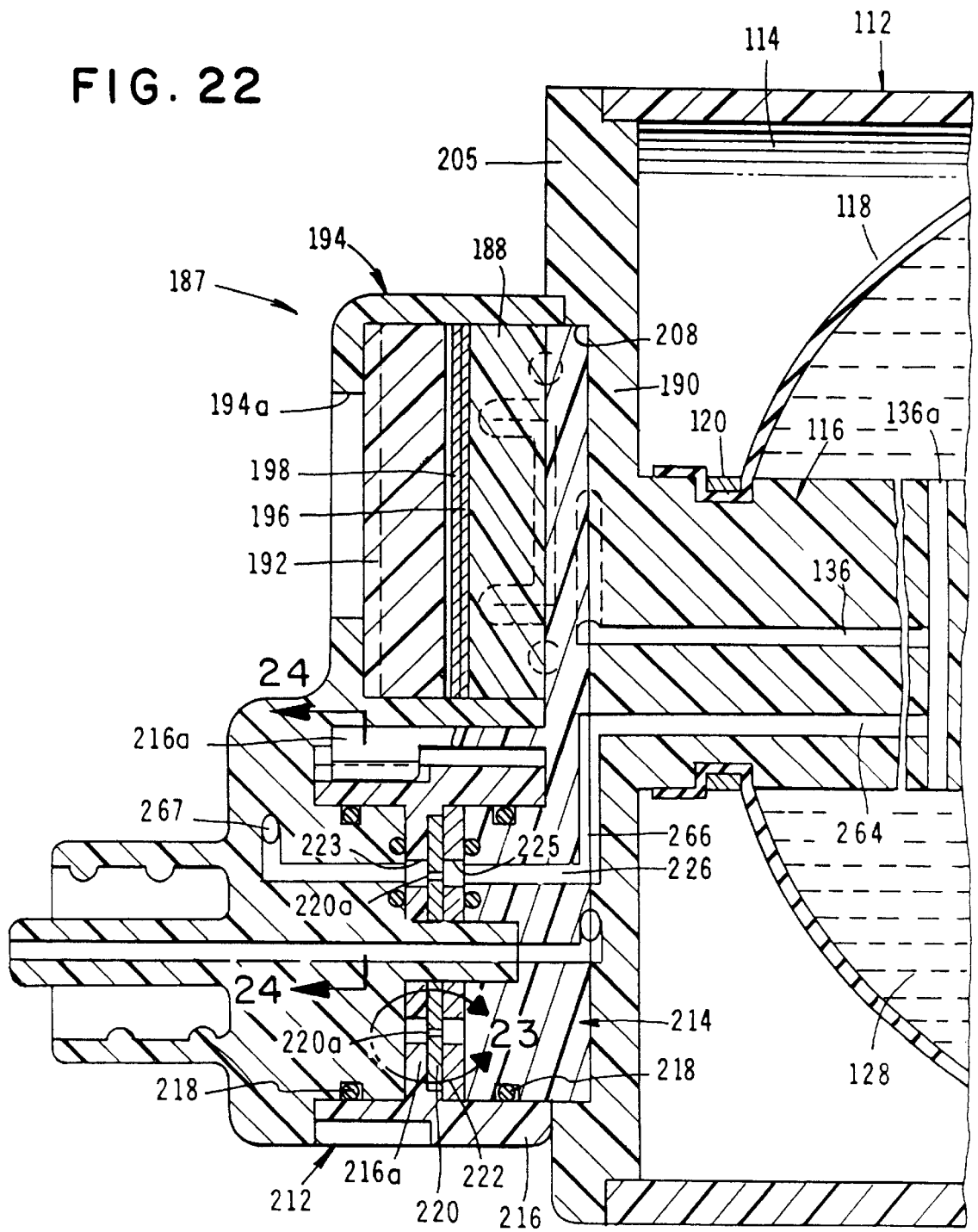
FIG. 22 is a greatly enlarged perspective, exploded view of tile apparatus shown in FIG. 20.
Figure 24:
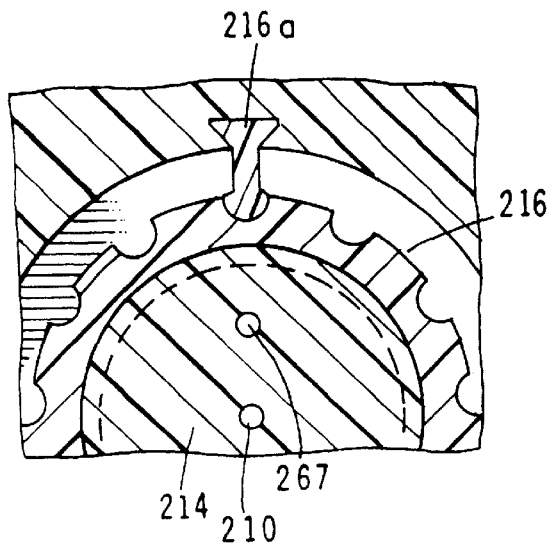
FIG. 24 is a cross-sectional view taken along lines 24—24 of FIG. 22.
Figure 25:
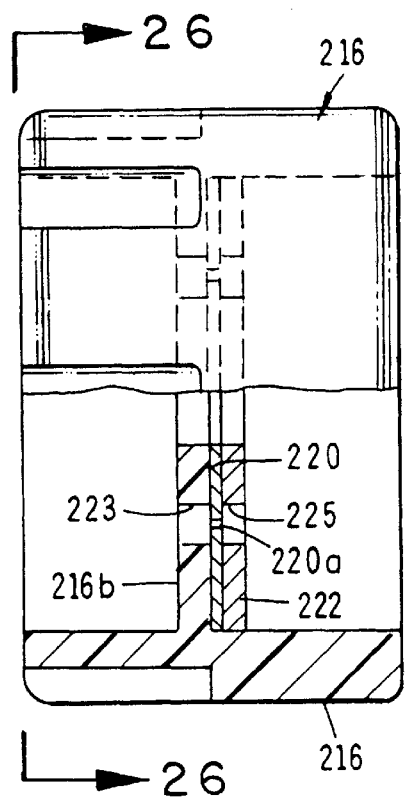
FIG. 25 is an enlarged view, partly in cross-sectional of the rate control means of the apparatus shown in FIG. 22.
Figure 26:
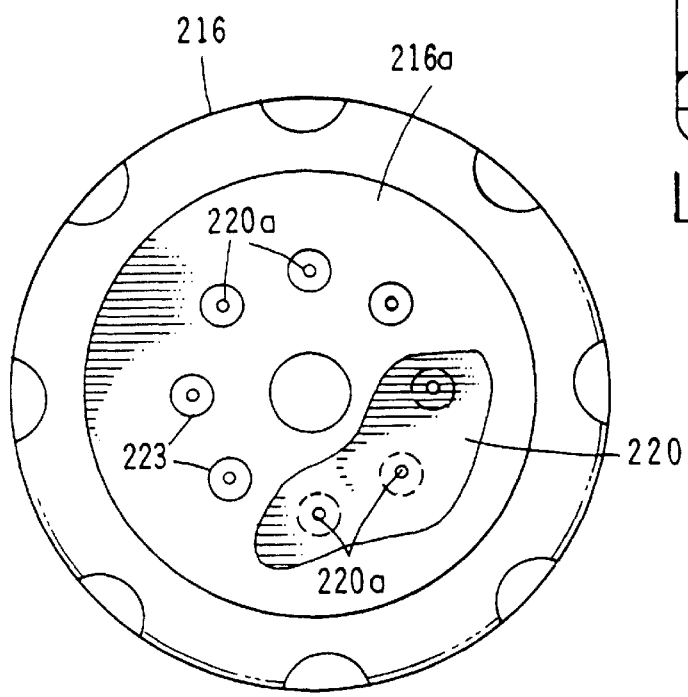
FIG. 26 is a view taken along lines 26—26 of FIG. 25.

Turning next to FIGS. 20 through 26, another form of the apparatus of the invention is there shown. This apparatus is similar in construction and operation to that shown in FIGS. 9 through 17 and includes the previously described adjustable rate control mechanism. However, this latest form of the invention also uniquely includes novel flow indicator means. This important flow indicator means, which is generally designated by the numeral 187, functions to distinguish among three conditions of operation, namely normal fluid flow, blockage or occlusion, and reservoir empty. Turning particularly to FIG. 21, the flow indicator means here comprises an indicator base or platform 188, as well as a boot clamping plate 190. Additionally, the indicator means comprises a support or lens plate 192, and a hollow housing 194 within which the platform and the support plate are enclosed (see also FIG. 20). As indicated in FIGS. 20 and 21, plate 192 is viewable through an aperture 194a provided in housing 194.

Disposed between lens plate 192 and platform 188 are first and second indicia-carrying means shown here as a pair of closely adjacent, thin films. These films identified here as 196 and 198, are in intimate contact and are preferably constructed from a substantially transparent, flexible polymer material such as mylar. It is to be understood that the indicia-carrying means need not be thin films, but rather can be any type of surface presenting member upon which indicia can be provided. The downstream surface of the inferior or first film 196 is printed with three integrated symbols (see FIGS. 4,6, and 8 or incorporated by reference U.S. Pat. No. 5,721,382, which may comprise, by way of example, a blue circle, a green arrow, and a red cross, each consisting of diagonal strips of color printed in an alternating pattern (blue, green, red, blue, green, red, and so on). The second film 198 serves as a "mask" over film 196 and is printed with a pattern of diagonal alternating clear and opaque strips that occur in approximately a 1:2 ratio. The printed ratio of the "mask" allows only one colored symbol to appear at a time when viewed through viewing lens plate 192. The inferior and superior films are provided at their opposite ends with apertures 200 which receive retention pins 202 provided on platform 188 (FIG. 19) which permit attachment of the film to platform 188 in a manner such that the non-patterned portions of each film covers boot openings 188a and 188b provided proximate each end of platform 188 with the patterned portions of both the superior and inferior films being maintained in index. With this construction, each thin film is able to move in response to pressure exerted thereon by the actuating means of the invention, the character of which will presently be described, in opposing directions parallel to the film plane with its range of motion limited to one axis in the film plane. As the films move, the visible symbol pattern will, of course, change due to the transverse displacement of the patterns imprinted thereon.

Figure 35:
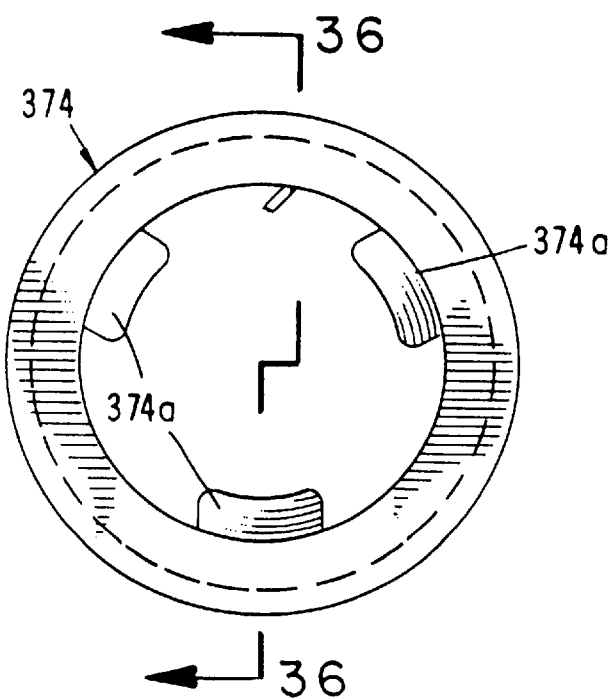
FIG. 35 is a front view of the advancement control knob of the device shown in FIG. 32A.
Figure 36:
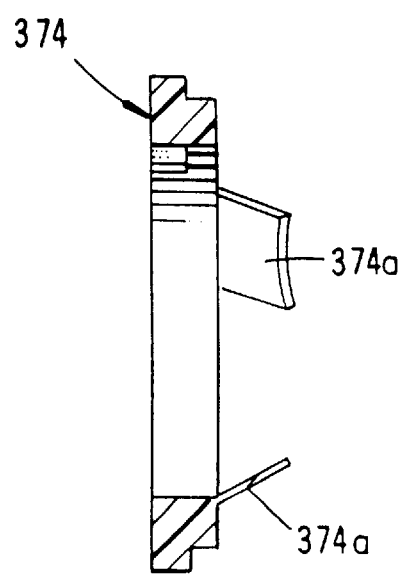
FIG. 36 is a cross-sectional view taken along lines 36—36 of FIG. 35.
Figure 42:
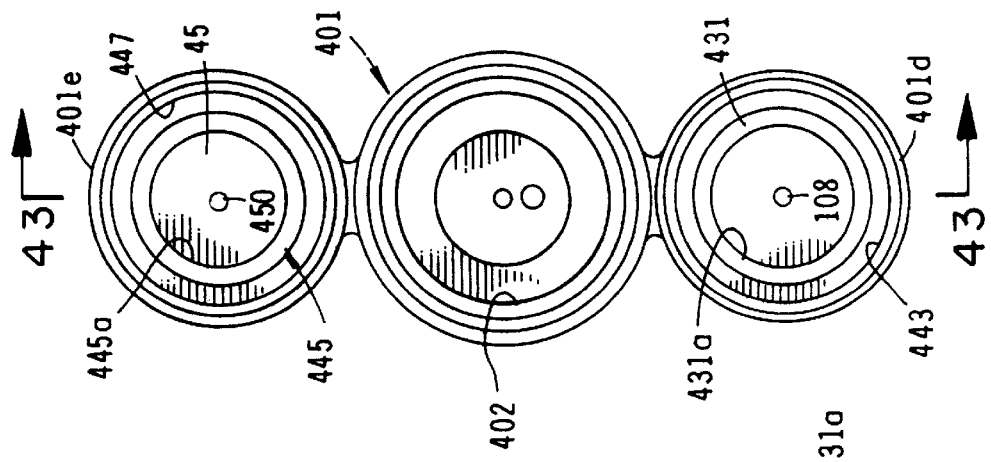
FIG. 42 is an end view of the housing of the apparatus.
Figure 43:
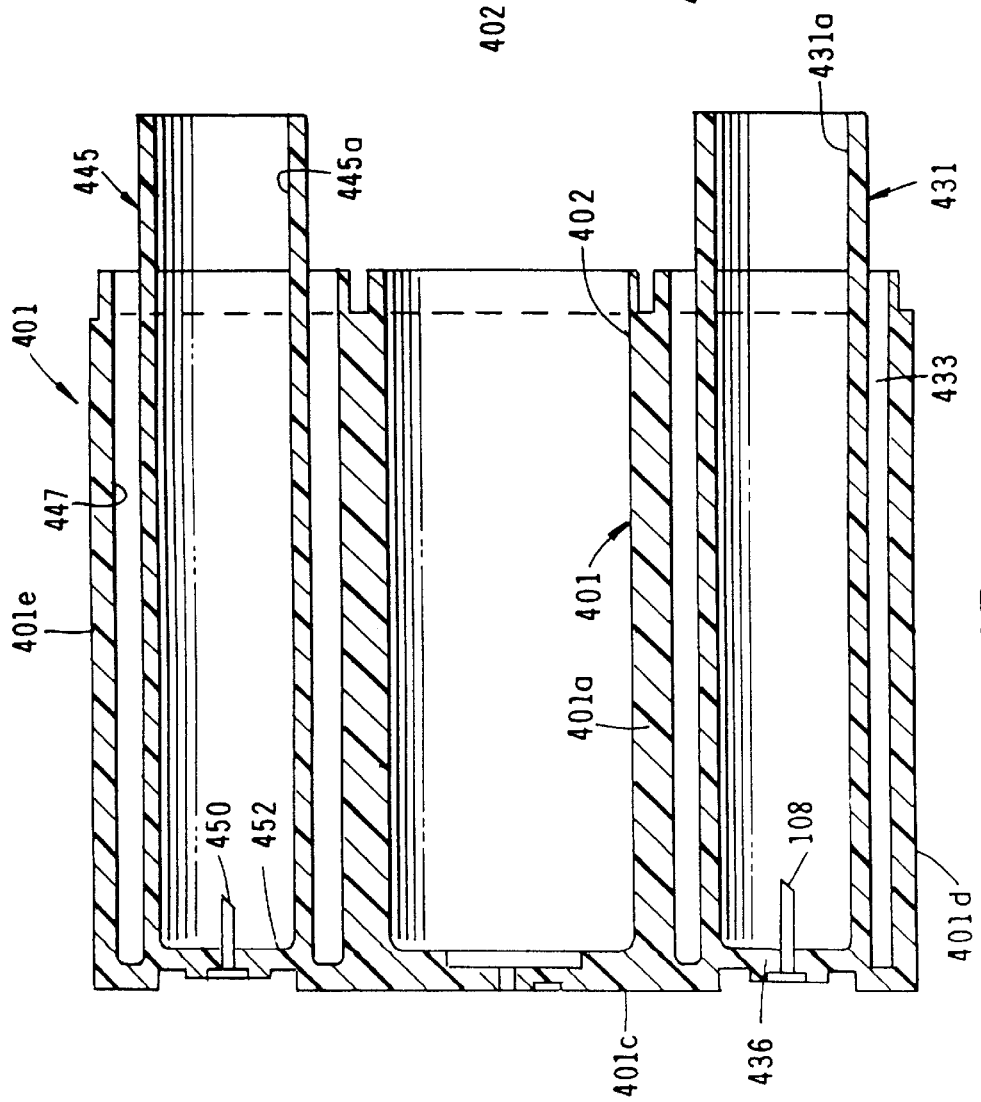
FIG. 43 is cross-sectional view taken along lines 43—43 of FIG. 42.
Figure 45:
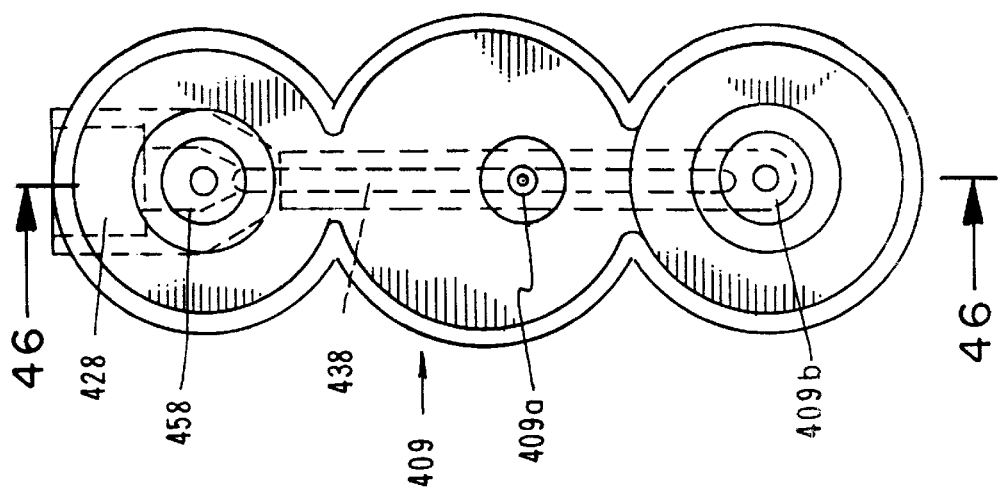
FIG. 45 is a right-side view of the closure cap of the apparatus which is connected to the housing in the manner shown in FIG. 39.
Figure 44:
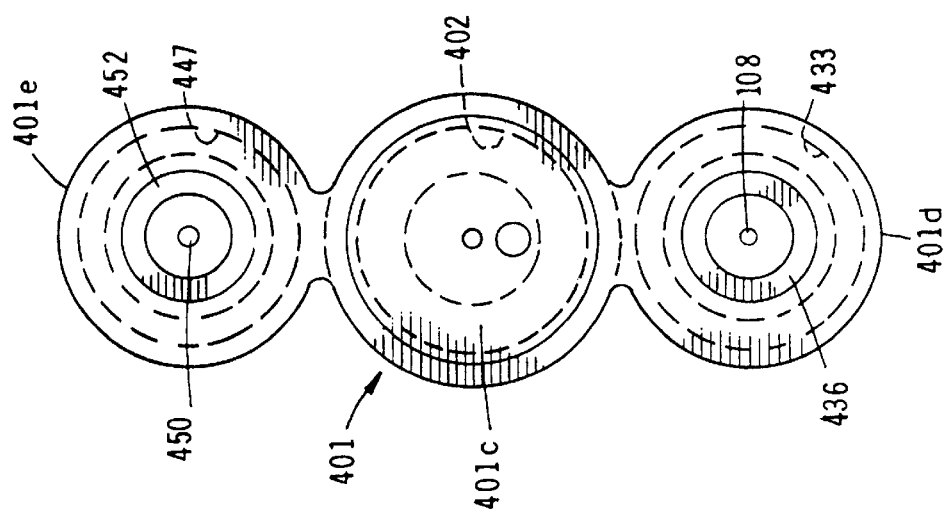
FIG. 44 is a left-end view of the housing of the apparatus shown in FIG. 43.
Figure 49:
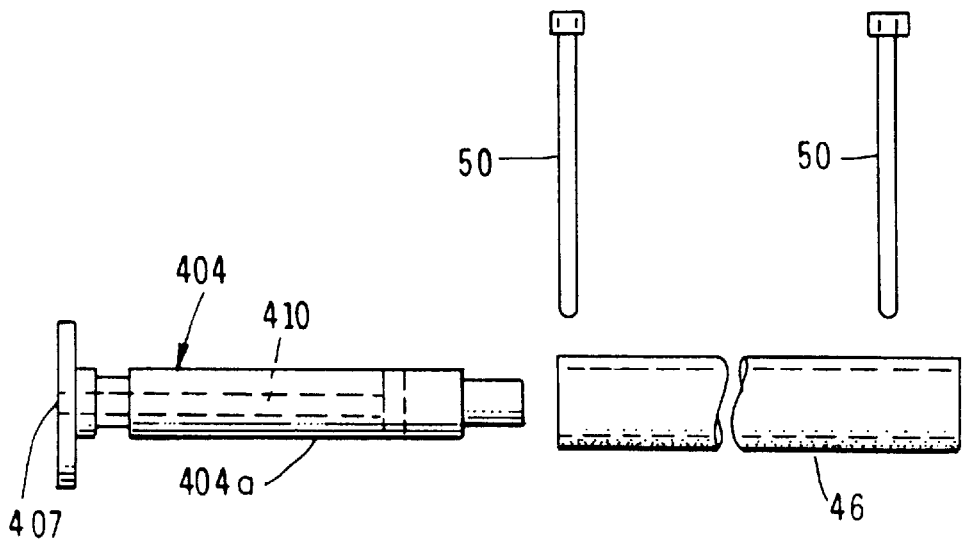
FIG. 49 is a fragmentary, exploded, side-elevational view of a portion of the central support of the device to which the elastomeric stored energy source of the device is affixed.
Figure 50:
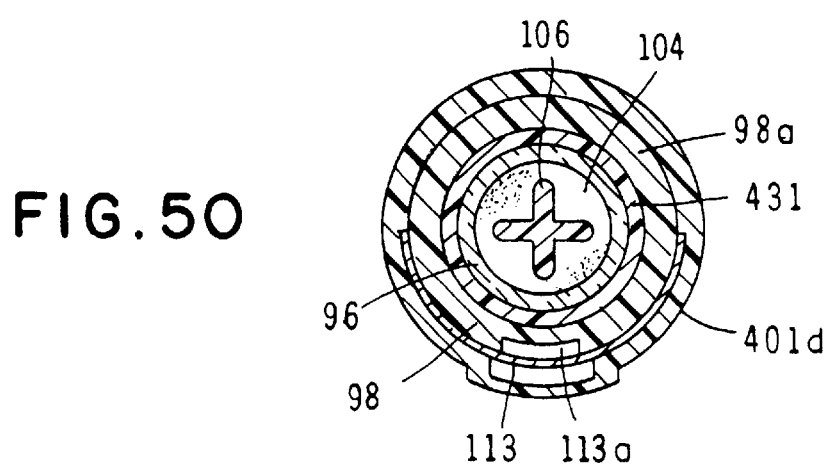
FIG. 50 is a cross-sectional view taken along lines 50—50 of FIG. 39.
Figure 51:
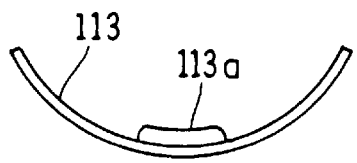
FIG. 51 is an end view of the retaining clip of the apparatus for locking the adapter assembly in place within the device housing.
Figure 52:
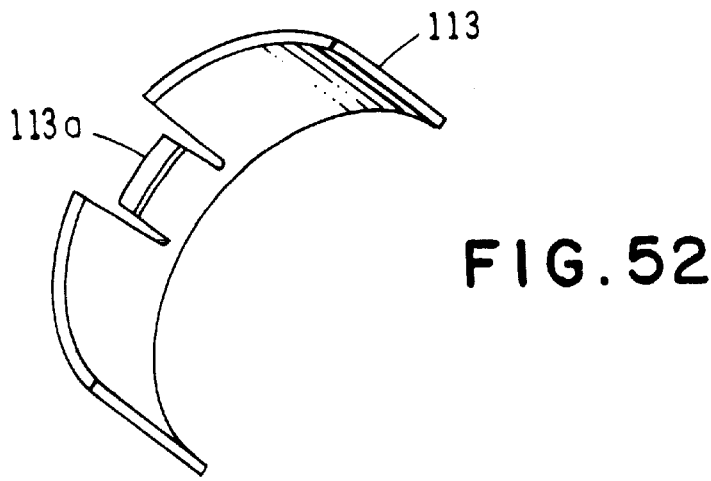
FIG. 52 is a generally perspective view of the retaining clip.
Figure 53:
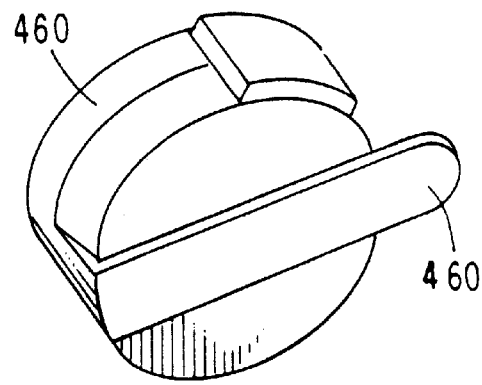
FIG. 53 is a generally perspective view of one of the sealing caps of the device for sealing the vial receiving chambers of the housing.
Figure 54:
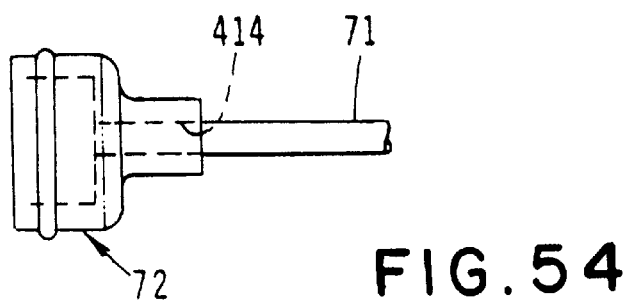
FIG. 54 is a side-elevational view of one form of the fluid delivery quick coupling component of the apparatus.

As will be discussed in greater detail hereinafter and as is apparent from a study of FIG. 21, the central portions of both the first and second elastomeric actuator elements or boots 204 and 206, which here comprise the actuator means of the invention, will be deflected outwardly in a direction toward plate 192 when the device is filled and primed, but not in a state of delivery or when there is a build up of fluid pressure during delivery that is caused by blockage of the delivery line downstream from boot 204. While boot 204 can be deflected by normal line pressure, boot 206 is deflected only by pressure buildup resulting from the downstream blockage. When both elastomeric boots 204 and 206 are deflected outwardly, both the superior and inferior films are displaced transversely to a second position revealing a second symbol, as for example, an X as viewed through the viewing aperture of the support plate (see also FIGS. 35 and 36 of U.S. Pat. No. 5,721,382 which is incorporated herein by reference).

Figure 32A:
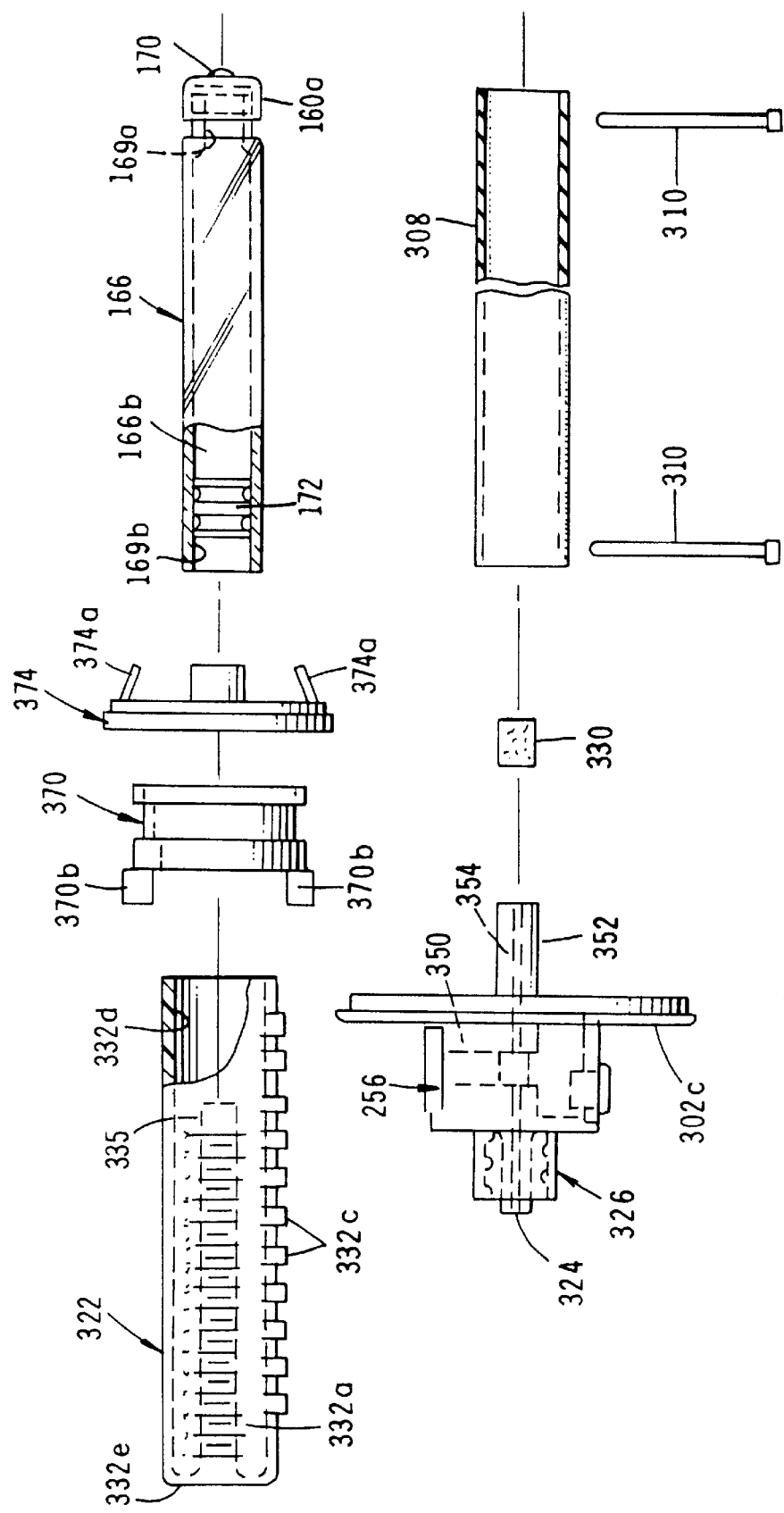
FIGS. 32A and 32B, when considered together, comprise an exploded view of the form of the fluid delivery apparatus shown in FIG. 28.

A third alignment of symbol patterns as shown in FIG. 32 of U.S. Pat. No. 5,721,382 is visible when the device is in an unfilled state or when the delivery line is open, the reservoir is empty and fluid delivery of the patient has been completed. In this case, there is no fluid pressure in the line on either the upstream or the downstream side of the flow control means and thus both the first and second boots are in a non-deflected position. In this condition, the interior and superior films are not transversely displaced and thus exhibit a third combination of patterns resulting in a third symbol as, for example, a circle being visible through the viewing aperture of the support plate. Boots 204 and 206 can be precisely tailored to deflect under various pressures thereby permitting great apparatus versatility.

As previously mentioned, the fluid dispenser apparatus of this latest form of the invention is quite similar to that shown in FIGS. 9 through 16 and includes an elongated housing 112 having an internal chamber 114 and extending longitudinally of the housing 112, and a generally cylindrically shaped, elongated elastomeric member 118 (FIG. 20).

As before, housing 112 comprises a cylindrically shaped central portion and inlet and outlet closure end plates. End plate 112b is of identical construction and operation to that previously described, but the forward end plate 205 is of a slightly different construction and carries the flow indicator means 187 (FIG. 21). In the manner previously described, elastomeric member 118 is securely affixed proximate its ends to support 116 by means of Suitable ring clamps 120 such as self-locking plastic panduit strips.

As best seen by referring to FIGS. 20 and 21, end plate 205 is provided with a chamber 208 which sealably receives plate 190 so that, in a manner presently to be described various fluid passageways formed in end plate 205 are placed in communication with reservoir 128.

As in the earlier describe embodiment of the invention, a novel flow rate control means is here provided for adjustably controlling the rate of fluid flow from the reservoir of the apparatus to the delivery passageway 210 of the apparatus. This means here comprises an adjustable rate control mechanism 212 which is carried by a forwardly extending, hub-like protuberance 214 formed on plate 190. Rotatably mounted on protuberance 214 is the control knob 216 of the rate control means. O-rings 218 carried by protuberance 214 sealably engage control knob 216 and prevent leakage therebetween. A flexible tab 216a which is connected to the housing functions to correctly index the knob (FIG. 21).

Control knob 216 is somewhat similar to control knob 164 and includes a central wall 216a which supports one face of member 220 which is provided with a plurality of circumferentially spaced, laser drilled microbores 220a. Tile other face of member 220 is supported by a spacer wall 222 which abuts cover 205 (FIG. 20). Members 216a and 222 are provided with indexable apertures 223 and 225 respectively, which are aligned with a fluid passageway 226 formed in member 190. By rotating control knob 216, a selected one of the laser drilled microbores 216a can be moved into alignment with apertures 223 and 225. In a manner next to be described, by selecting an aperture of a particular size, the rate of fluid flow toward outlet passageway 210 can be precisely controlled.

During the fluid dispensing step, when fluid is forced through reservoir outlet 136a by the stored energy means, the fluid will flow into passageway 136, through filter 144 and then into passageway 154. Next, the fluid will flow in end portion 205, then through an aperture 246 formed in plate 190 and finally into a chamber 250 formed in a distendable, elastomeric first boot 206 of the flow indicator means of the invention. Boot 206 includes a yieldably distendable fluid flow blocking body portion 252 which is circumscribed by a marginal portion 254. Marginal portion 254 is clamped between plate 190 and platform 188 so that the boot extends through opening 188a formed in platform 188. It is to be understood that, when the fluid flowing from reservoir 128 in the direction of arrow 260 impinges upon boot 206, the central portion of the boot will be deflected outwardly into pressural engagement with indicator film 198.

Fluid flowing from reservoir 128 will also flow in the direction of arrow 264 (FIG. 21) into a Stub passageway 266 formed in member 205 and then into passageway 226 (FIG. 22) when it will pass through the flow restrictor aperture 220a 266 and then will be diverted in the direction of arrows 268 of FIG. 20 rearwardly toward end portion 205 and into a passageway 270 formed thereon.

Next, the fluid will flow through passageway 270 and then forwardly in the direction of the arrows 274, through an aperture 275 formed in plate 190 and into chamber 276 formed in elastomeric, distendable boot 204 which also forms a part of the indicator means of the invention. The periphery 278 of indicator boot 204, which is of identical construction to boot 206, is clamped within opening 188a formed in platform 188. After impinging on boot 204, the fluid will next flow back toward plate 190 in the direction of arrow 280, through orifice 284 formed therein and then in the direction of arrows 286, into a passageway 290 formed in end portion 205. Upon entering passageway 290, the fluid will flow downwardly of passageway 210 (FIG. 22) and finally in the direction of arrow 294 into the delivery line 296 which is connected to the outlet port of the device (FIG. 20).

It is to be observed that fluid flowing from reservoir 128 into passageway 266, into passageway 290 and then on toward boot 204 is under a lower pressure than fluid flowing toward boot 206. This is because the pressure of the fluid flowing toward boot 204 has been reduced as a result of the fluid flowing through the adjustable rate control means of the invention. As will be discussed more fully in the paragraphs which follow, this result enables a determination of the various fluid flow operating conditions of the device namely normal fluid flow, fluid flow blockage or occlusion, and reservoir empty.

In addition to boots 204 and 206, the flow indicator means also comprises the earlier identified lens 192, and the forward housing 194 within which the platform 188 and the support plate 192 are enclosed (FIG. 20). As seen in FIG. 20, the viewing lens 194 is viewable through an opening 194a provided in forward housing 194. Disposed between platform 188 and lens 192 are the earlier mentioned first and second indicia-carrying means, or closely adjacent overlaying then films 196 and 198. These films are quite similar in construction and operation to films 26 and 28 of the device described in incorporated by reference U.S. Pat. No. 5,721,382 and, for a more complete understand of these films, reference should be made to this patent. Films 196 and 198 are in intimate contact and are preferably constructed from a substantially transparent, flexible polymer material such a mylar. The downstream surface of the inferior or first film 196 is printed with three integrated symbols (see FIG. 3 of U.S. Pat. No. 5,721,382 which may comprise, by way of example, a blue circle, a green arrow, and a red X, each consisting of diagonal strips of color printed in an alternating pattern (blue, green, red, blue, green, red, and so on (see FIGS. 4, 6 and 8 of U.S. Pat. No. 5,721,382). The second film 198 serves as a "mask" over film 196 and is printed with a pattern of diagonal alternating clear and opaque strips that occur in approximately a 1:2 ratio. The printed ratio of the "mask" allows only one colored symbol to appear at a time when viewed through viewing lens 192. As previously mentioned, the inferior and superior films are provided at their opposite ends with apertures 200 which receive retention pins 202 provided on platform 188 which permit attachment of the films to platform 188 in a manner such that the non-patterned portions of each film covers boot openings 188a and 188b provided proximate each end of platform 188 with the patterned portions 188a and 188b provided proximate each end of platform 188 with the patterned portions of both the superior and inferior films being maintained in index. With this construction, each thin film is able to move in response to pressure exerted thereon by the elastomeric boots 204 and 206 in opposing directions parallel to the film plane with its range of motion limited to one axis in the film plane. As more fully described in U.S. Pat. No. 5,721,382, as the films move, the visible symbol pattern will, of course, change due to the transverse displacement of the patterns imprinted thereon. As is apparent from a study of FIG. 21, that the central portions of both the first and second elastomeric actuator elements or boots 204 and 206 will be deflected outwardly toward films 196 and 198 when the device is filled and primed, but not in a state of delivery or when there is a build up of fluid pressure during delivery that is caused by blockage of the delivery line downstream from boot 204. While boot 206 can be deflected by normal line pressure, boot 204 is deflected only by pressure buildup resulting from the downstream blockage. When both elastomeric boots 204 and 206 are deflected outwardly, both the superior and inferior films are displaced transversely to a second position revealing a second symbol, as for example, an X as viewed through the viewing aperture 194a. When fluid is flowing through the device, an indicia, for example, is visable through tile viewing window.

A third alignment of symbol patterns is visible when the device is in an unfilled state or when the delivery line is open, the reservoir if empty and fluid delivery to the patient has been completed. In this case, there is no fluid pressure in tile line on either the upstream or the downstream side of the flow control means and thus both the first and second boots are in a non-deflected position. In this condition, the inferior and superior films are not transversely displaced and thus exhibit a third combination of patterns resulting in a third symbol as for example, a circle being visible through tile viewing aperture of the support plate. Boots 204 and 206 can be precisely tailored to deflect under various pressures thereby permitting great apparatus versatility. Reference should also be made to U.S. Pat. No. 5,721,382, which patent is incorporated by reference herein, for further discussion of the construction and operation of the indicator means of the invention.

The fill means of this latest form of the invention is identical in construction and operation to that of the earlier described embodiment and includes a container subassembly and an adapter subassembly of the same character as previously described.

Figure 27:
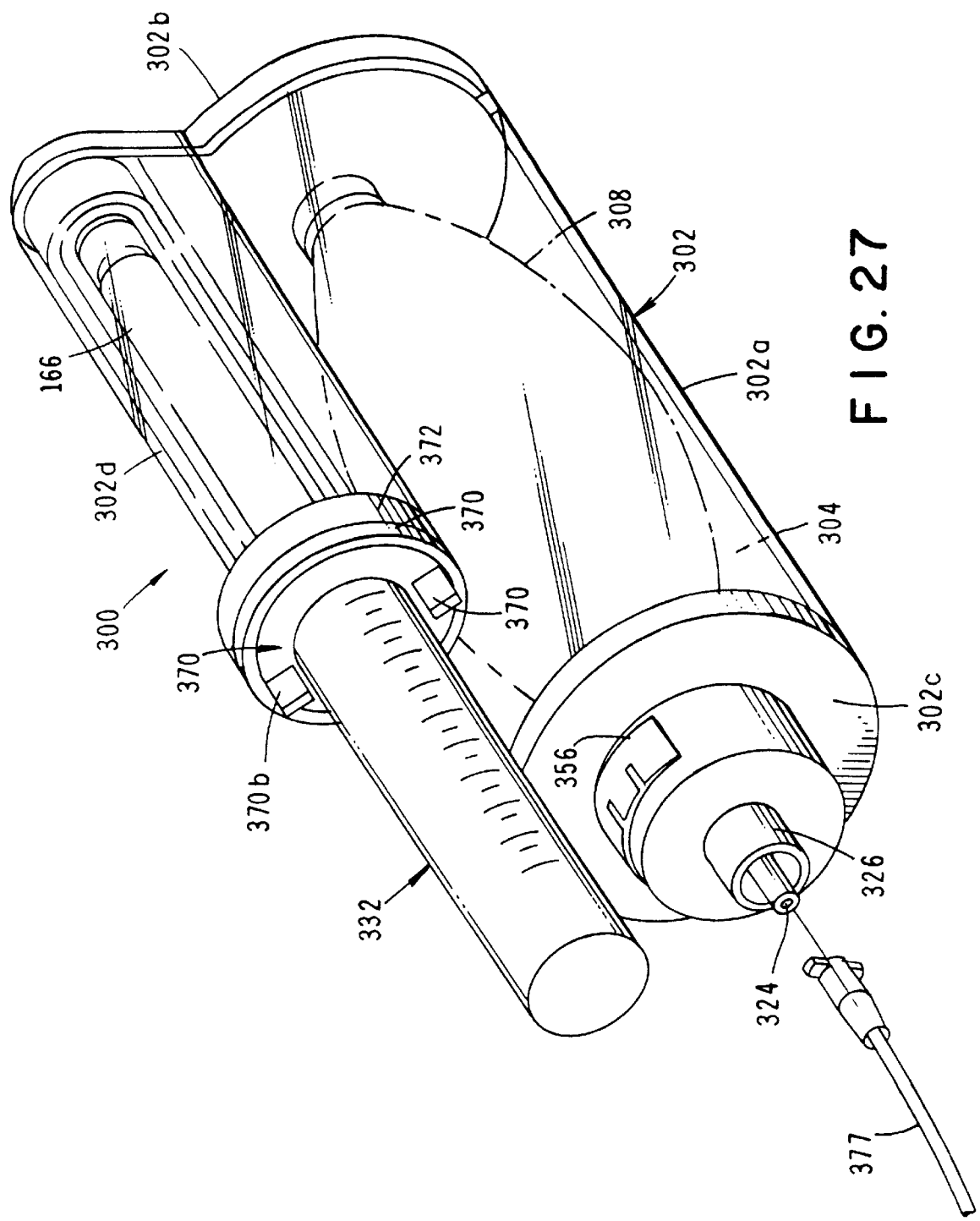
FIG. 27 is a generally perspective exploded view of another form of the fluid delivery apparatus of the present invention.
Figure 28:
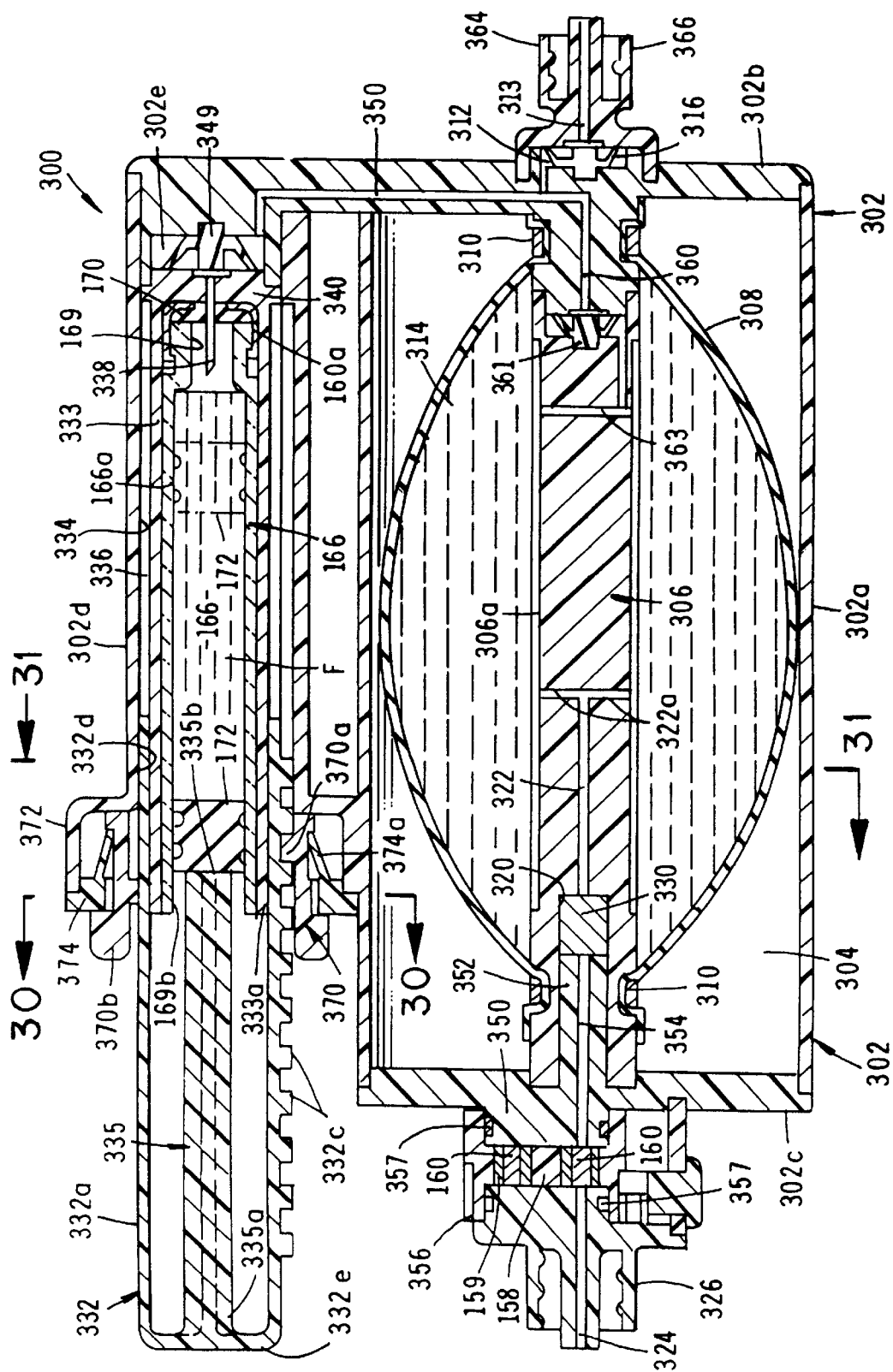
FIG. 28 is an enlarged, side-elevational, cross-sectional view of the device shown in FIG. 27.
Figure 29:
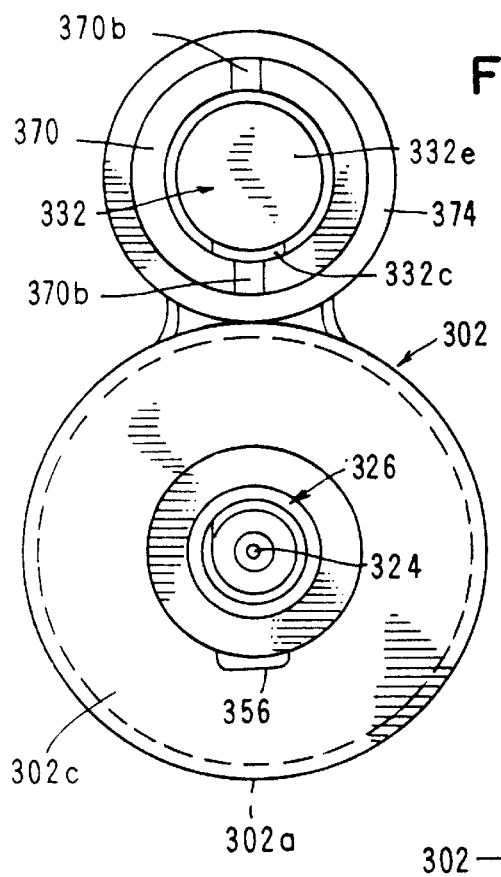
FIG. 29 is a left end view of the device shown in FIG. 2.
Figure 31:
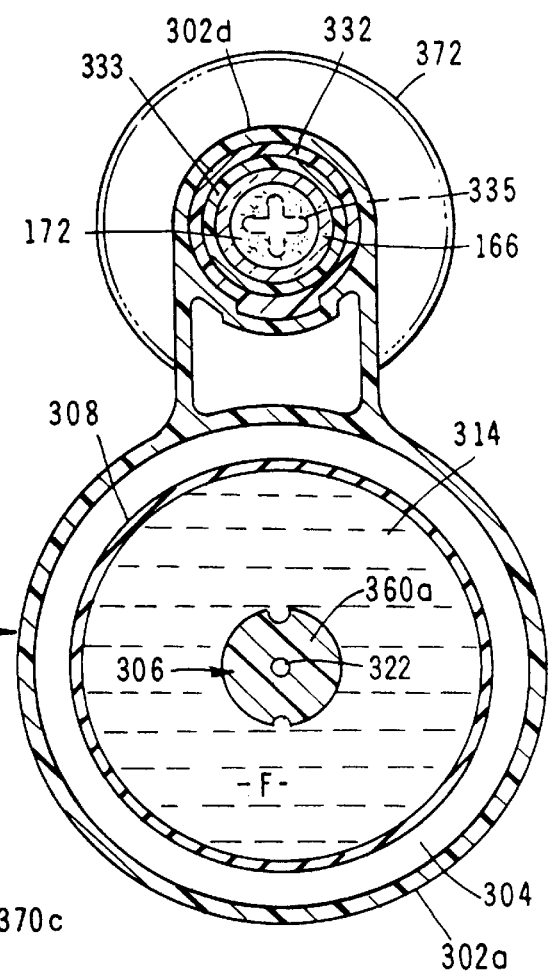
FIG. 31 is a cross-sectional view taken along lines 31—31 of FIG. 28.

Turning next to FIGS. 27 through 36, still another form of the fluid dispenser apparatus of the invention is there illustrated and generally designated by the numeral 300. This latest form of the invention is similar in many respects to that shown in FIGS. 1 through 26 and like numerals are used to identify like components. As in the embodiment shown in FIGS. 1 through 8, the present embodiment comprises an elongated housing 302 having a first internal chamber 304, a support 306 disposed within internal chamber 304 and extending longitudinally of the housing 302, and a stored energy means provided in the form of a generally cylindrically shaped, elongated elastomeric member 308 (FIG. 28).

Housing 302 comprises a cylindrically shaped central portion 302a and inlet and outlet closure portions 302b and 302c respectively. Central section 302a can be connected to end plates portions 302b and 302c by any suitable means such as adhesive bonding or an appropriate sonic weldment. Elastomeric member 308 is securely affixed proximate its ends to support 306 by means of suitable ring clamps 310 such as self-locking plastic panduit strips.

As best seen by referring to FIG. 28, support 306 is provided with a first chamber 312 having a fluid inlet 313 which, in a manner presently to be described, is in communication with the first fill means of the invention for filling a reservoir 314 with a diluent or like fluid. Reservoir 34 is formed by elastomeric member 308 and the central portion 306a of support. Valve means, shown here as a check valve 316 is disposed within chamber 312 and functions to permit fluid flow toward reservoir 314, but blocks fluid flow in the opposite direction.

Support 306 is also provided with a second chamber 320 having an inlet passageway 322 which includes transversely extending segments 322a. A fluid dispensing means, including a fluid delivery passageway 324 formed in luer connector 326 is provided proximate the outlet end of the device. As shown in FIG. 28, delivery passageway 324 is in communication with inlet passageway 322 via the novel adjustable flow rate control means of the invention. Disposed within chamber 320 is a filter means, which here comprises a porous filter element 330 of conventional construction. Filter element 330 functions to filter particulate matter that may be contained within the fluid flowing from reservoir 314.

The previously mentioned flow rate control means of this latest form of the invention is substantially identical to that shown in FIGS. 9 through 14 and earlier described herein and like numbers are used in the drawings to identify like components. As before, this important means functions to precisely control the rate of fluid flow from the reservoir of the apparatus to the delivery passageway 324 and includes the previously described adjustable rate control mechanism which is carried proximate the outlet of the device. More particularly, as best seen in FIG. 28, the mechanism here comprises a part of end portion 302c which includes a hub-like portion 350 having an elongated stem 352 which is receivable within second chamber 320 of support 306. Provided at the forward portion of the assemblage is the previously identified luer-like conductor 326. Hub-like portion 350 and stem portion 352 are provided a with passageway 354 which is in communication with both inlet passageway 322 and with fluid delivery passageway 324. Rotatably carried by hub-like portion 350 is a control knob 356. O-rings 357 carried by portions 350 sealably engage control knob 356 and prevent leakage among the various cooperating components.

Mounted within control knob 356 and rotatable therewith is control member 158. As in the earlier described embodiments of the invention, control member 158 carries a plurality of circumferentially spaced apart flow restrictors 160 each of which can be selectively moved into index with flow passageway 354 of body 350 by rotating knob 356 relative to body portion 350. As in the embodiment shown in FIG. 12, the flow restrictors are provided in the form of rate control frits 160 which are secured in place within apertures 158a formed in member 158 by a moldable elastomer 159. With the construction shown, by rotating knob 356 relative to body portion 350, each of the rate control frits 160 can be selectively moved into alignment with passageway 254. Because each of the frits 260 is of a different, preselected porosity it is apparent that the rate of fluid flowing outwardly of the device through delivery passageway 224 can be precisely controlled by selecting a frit of the desired porosity.

Turning once again to FIG. 28, the second fill means of the invention is somewhat similar to that shown in FIGS. 1 and 2 and, once again, like numbers are used to identify like components. This second fill means here comprises a container subassembly 166, and an adapter subassembly 332. Container subassembly 166 is identical to that previously described in connection with FIGS. 10 and 11 and includes a body portion 166a having a fluid chamber 166b for containing an injectable fluid "F". Fluid chamber 166b is provided with first and second open ends 169a and 169b. First open end 169a is sealably closed by closure means here provided in the form of a pierceable septum 170 (see also FIG. 11). Septum 170 is held securely in position by clamping ring 160a. A plunger 172 is telescopically movable within chamber 166b of container subassembly 166 from a first location proximate first open end 169b to a second position proximate second open end 169a. As before, the vial portion of the container subassembly 166 can be constructed of various materials such as glass and plastic.

Adapter subassembly 332, which is of a slightly different construction from that of adapter subassembly 168, here comprises a hollow housing 332a having a first open end 332d and a second closed end 332e. In using the apparatus of this latest form of the invention, container subassembly 166 can be telescopically inserted into the open end 333a of a vial receiving tube 333 which is, in turn, received within an elongated, generally cylindrically spaced chamber 334 formed in the upper portion 302d of housing 302. With this construction, hollow housing 332a can be moved from the extended position shown in FIG. 28 into a vial encapsulation position wherein the vial resides interiorly of the adapter subassembly. Forming an important part of adapter subassembly 332 is pusher means shown here as an elongated pusher rod 335 which functions to move plunger 172 longitudinally of fluid chamber 166b from a first extended position to the position shown by the solid lines to a second position shown by the phantom lines of FIG. 28. Pusher rod 335 has a first end 335a interconnected with the closure wall 332e of housing 332 and an opposite end 335b which engages plunger 172 and causes telescopic movement of the plunger within chamber 166b of container subassembly 166 as housing 332a is moved within an annular space 236 formed between vial receiving tube 333 and chamber 334 of device housing portion 302d.

Figure 32B:
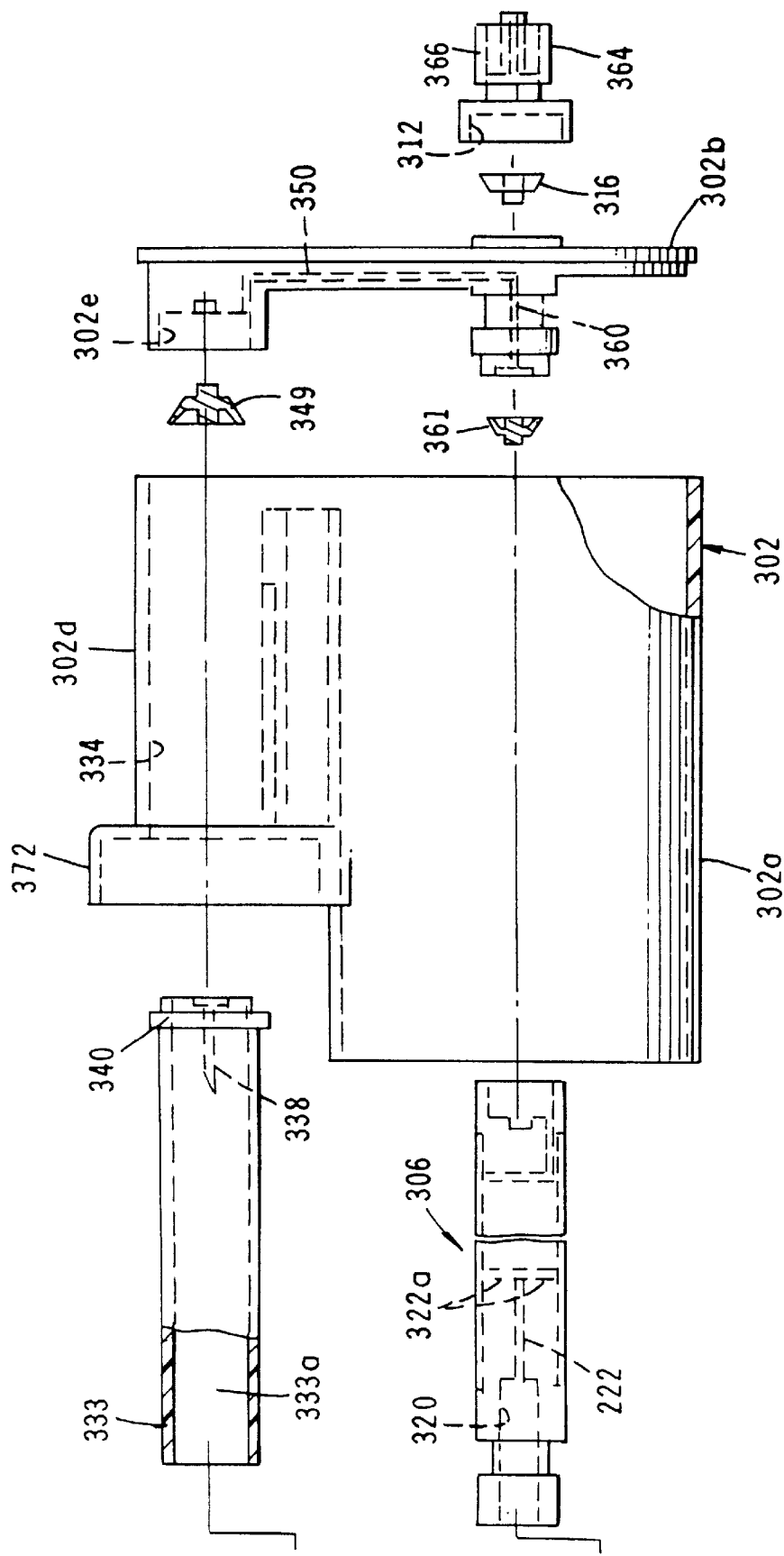
Figure 33:
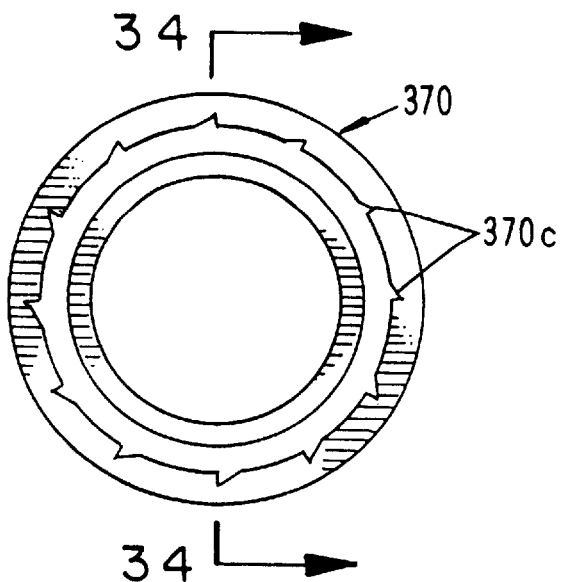
FIG. 33 is a front view of the advancement control knob of the device shown in FIG. 32A

As best seen in FIG. 32B, a hollow piercing cannula 338 is connected to a support wall 340 formed on vial receiving tube 333. Cannula 338 extends into receiving chamber 333a formed in vial receiving tube 333 so that it can pierceably engage septum 170 of the fill vial assembly. A fluid passageway 302d formed in end portion 302b of device housing 302 communicates with internal the fluid passageway of hollow cannula 338 via a check valve 349 which is mounted within a chamber 302e formed in end portion 302b to enable fluid flow from vial 166, past the check valve, and into an inlet passageway 360 formed in end portion 302b. The fluid can then flow into reservoir 314 via a check valve 361 and inlet passageway 363 (FIG. 28). Check valve 361 permits fluid flow toward reservoir 214 but blocks fluid flow in the opposite direction.

In using this latest form of the invention, which is shown in FIGS. 28 through 36, the first fill means, which includes a luer-like connected or 364, can be used, by way of example, to initially fill reservoir 314 with a saline solution. Luer-like connector 364 comprises a part of the fill port assembly 366 of the invention which cooperates with end portion 202b of housing 202 to form the earlier identified chamber 213. Fill port assembly 366 can be suitably interconnected with a conventional male luer connector and fill line (not shown) which can be connected to a suitable source of diluent or like fluid. A conventional luer cap (not shown) can be used to sealably close connector 360 when it is not in use.

In using the apparatus of the invention, mating of the container subassembly 166 with the adapter subassembly 332 is accomplished by telescopically inserting the container subassembly into vial receiving tube 333. This done, housing 332a of the assemblage is controllably moved forwardly within annular space 336. As the adapter subassembly moves forwardly, pusher rod 335 will engage plunger 172 causing the container assembly to also move forwardly. As the container assembly approaches a seated position, piercing cannula 338 will pierce septum assembly 170 of the container assembly. Once the fluid flow path between the hollow cannula 338 and the fluid reservoir 314 is thus created via passageway 302d, 360 and 363, a continued inward movement of the adapter subassembly 332 can be here accomplished by a novel advancement means, the construction and operation of which will presently be described. As the adapter subassembly moves inwardly pusher rod 335 will move plunger 172 forwardly of chamber 166b. As plunger 172 is moved forwardly, fluid contained within vial chamber 166b, will flow through hollow cannula 338, past check valve 349, into passageway 302 into inlet passageways 360 and 363 and finally into fluid reservoir 314 where it will controllably intermix with a saline solution or the like which has previously been introduced into reservoir 314 using the first fill means of the invention.

Figure 30:
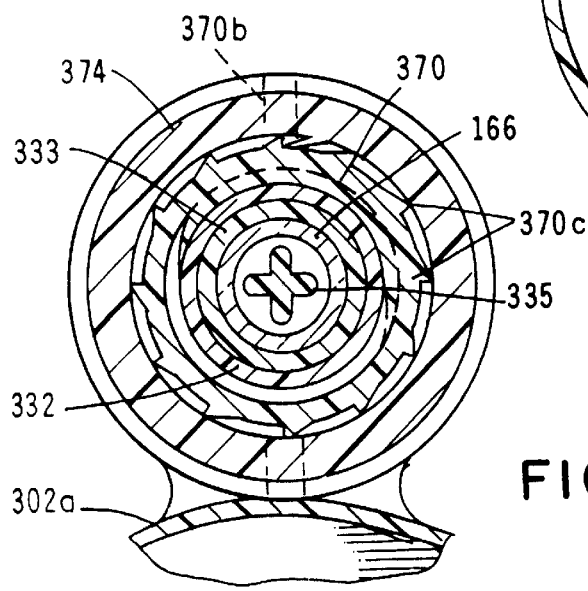
FIG. 30 is a cross-sectional view taken along lines 30—30 of FIG. 28.
Figure 34:
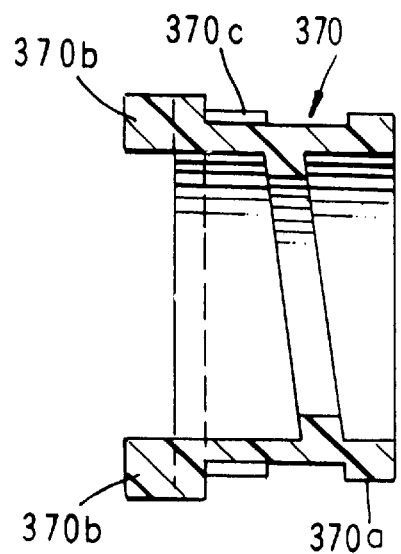
FIG. 34 is a cross-sectional view taken along lines 34—34 of FIG. 33.

Considering the previously identified advancement means of the invention, this means here comprises a control knob 370, which is rotatably mounted within an enlarged diameter, mouth-like portion 372 formed on upper device housing portion 202d (FIGS. 28 and 32B). Control knob 370 is held in place within portion 372 by means of knob engaging tabs 374 provided on a retaining ring 374. The details of construction of knob 370 and retaining ring 374 are illustrated in FIGS. 33, 34, 35 and 36. As indicated in FIG. 34, control knob 370 is provided with an external thread 370a which mates with threads 332c formed on adapter housing 332a of adapter assembly 332. With this construction, as knob 370 is rotated by rotational forces exerted on finger tabs 370ba, adapter housing 332a will be caused to controllably move inwardly of annular space 330 causing pusher rod 335 to move plunger 172 inwardly of vial 166 in the manner previously described. In this way precise incremental amounts of the medicament contained within vial 166 can be controllably introduced into reservoir 314 and intermixed with the saline solution earlier introduced via the first fill means or fill port assembly 366. As shown in FIGS. 27 and 30, knob 370 is provided with antirotation teeth 370b which engage ring 374 to prevent reverse rotation of the knob. Additionally, locking teeth are provided on adapter body 332a, which locking teeth function in the manner earlier described to prevent removal of the adapter assembly after it has been advanced into housing portion 302d.

Once the desired amount of medicament contained within vial 166 has been mixed with the saline solution or other diluent contained within reservoir 314, the apparatus will remain in this filled condition until outlet passageway of the device is opened. Once the outlet passageway has been opened, the stored energy means or membrane 308 will tend to return to a less distended condition causing fluid to flow outwardly of the apparatus via passageway 322, through filter 330 and then through the selected rate control frit of the rate control means and finally outwardly of the device via delivery passageway 324. For this purpose, a delivery line 377 can be connected to connector 326 in the manner depicted in FIG. 27.

Referring to FIGS. 37 through 54, still another form of the apparatus of the invention is there shown and generally designated by the numeral 400. This apparatus is somewhat similar to that shown in FIGS. 1 through 8, but here includes two fill vials rather than one. Because of the similarity between this latest embodiment and that shown in FIGS. 1 through 8, like numerals are used in FIGS. 37 through 54 to identify like components. As best seen in FIGS. 37, 38, and 39, this latest form of the invention comprises an elongated housing 401 having an internal chamber 402, a support 404 disposed within internal chamber 402 and extending longitudinally of the housing 401 and a generally cylindrically shaped, elongated elastomeric member 46.

Housing 401 comprises a cylindrically shaped central portion 401a and inlet and outlet end closure portions 401b and 401c respectively. Central section 401a and end portion 401b can be interconnected by any suitable means such as adhesive bonding or an appropriate sonic weldment. End portion 401c is preferably integrally formed with central portion 401a although it could be formed as a separate component. The reservoir forming elastomeric member, which is identical to the previously described elastomeric member 46, is securely affixed proximate its ends to support 404 by means of suitable ring clamps 50 such as the previously identified, self-locking plastic punduit strips.

As before, support 404 is constructed in two parts 404a and 404b which are suitably interconnected in the manner shown in FIGS. 2 and 3a. Part 404a has a fluid inlet 407 which is in communication with a reservoir 58 formed by elastomeric member 46 and support 404 via a fluid passageway 410. Valve means, shown here as a check valve 62 which is disposed within a chamber 409a formed in an end cap 409, permits fluid flow in a direction toward reservoir 58 but blocks fluid flow in the opposite direction.

Second part 404b of support 404 has an outlet passageway 412 which communicates with the delivery means of the invention for delivering fluid to the patient. The delivery means includes a fluid delivery passageway 414 formed in a quick disconnect assembly which includes a housing 72 of the character previously described. The quick disconnect assembly, which is identical to that shown in FIG. 2, can be readily releasably interconnected with end portion 401b of housing 401. Fluid delivery passageway 412 communicates with reservoir 58 and also with passageway 414 via a flow rate control means, here provided as a porous rate control frit 74 which is identical in construction and operation to that previously described and which is mounted within quick disconnect housing 72.

An important feature of the apparatus of the present invention is the provision of a side-mounted sampling means for sampling and retrieval of fluid contained within reservoir 58. As best seen in FIGS. 37 and 40, the sampling means hear comprises a sampling port assembly 418 which is carried by end portion 401b of support 401. Sampling port assembly 418 includes a septum 420, which is received within a chamber 422 formed in housing end portion 401b, and a clamping ring 424 for clamping the septum in place within chamber 422. As before, the use of a sampling means such as a conventional syringe, the contents of reservoir 58 can be sampled at any time and, after the delivery step, any medicament remaining in the reservoir can be retrieved for subsequent use.

Formed in end cap 409 is a first fill means for filling reservoir 58 with a diluent such as a saline solution or with any other desired fluid. This first fill means here comprises a first fill port assembly 426 which includes a chamber 428 for in cap 409. Sealably disposed within chamber 428 is a conventional male luer connector 430 which can be suitably connected with a conventional female luer connector and fill line (not shown). A conventional luer cap 432 sealably closes connector 430 which is it not in use. As was earlier the case, connector 430 can include a conventional check valve to permit fluid flow toward reservoir 58 but to block flow in the opposite direction. With a suitable female luer connector connected to connector 430 and with the fill line connected to a source of diluent reservoir 58 can be partially filled with the diluent in a manner well understood by those skilled in the art.

Turning particularly to FIGS. 37, 38, and 39, the second fill means of the invention for adding fluid to reservoir 58 is there illustrated. This second fill means is of similar construction to that shown in FIGS. 1, 2, and 6 and comprises a container subassembly 96, and an adapter subassembly 98, which are of identical construction and operation to those previously described herein As in the earlier embodiment, container subassembly 96 is telescopically receivable within open end 431a of a vial receiving tube 431 which, in turn is received within an elongated, generally cylindrically spaced chamber 433 formed in portion 401d of housing 401. With this construction, hollow housing 98a can be moved from the extended position shown in FIG. 39 into a vial encapsulation position wherein the vial resides interiorly or the adapter subassembly. Adapter subassembly 98 includes pusher means comprising an elongated pusher rod 106 which functions to move plunger 104 longitudinally of fluid chamber 96b. As shown in FIG. 39, pusher rod 106 has an opposite end 106b which engages plunger 104 and causes telescopic movement of the plunger within chamber 96b of container subassembly 96 as housing is moved within chamber 433 which is formed between vial receiving tube 431 and the outer wall of housing portion 401d.

A hollow piercing cannula 108 is connected to support wall 436 formed on a vial receiving tube 431 and extends into receiving chamber 431a formed in vial receiving tube 331. A passageway 438 formed in closure cap 409 communicates with the fluid passageway of hollow cannula 108 via a check valve 442 which is mounted within a chamber 409b formed in cap 409. Check valve 442 permits fluid flow from vial reservoir 96b, into passageway 438 and then into inlet passageway 407 via check valve 62 and then finally into reservoir 58. However, check valve 442 effectively blocks fluid flow into the opposite direction.

Uniquely, this latest embodiment of the invention includes third fill means for adding fluid to reservoir 58. This third fill means is of similar construction to the second fill means and is adapted to receive a container subassembly 96, and an adapter subassembly 98 of the character previously described.

In using this third fill means, container subassembly 96 is uniquely telescopically receivable within the open end 445a of a vial receiving tube 445 which, in turn, is disposed within an elongated, generally cylindrically shaped chamber 447 formed in portion 401e of housing 401 (FIGS. 37 and 39). As before, a hollow housing 98a can be moved from an extended position into a vial encapsulation position wherein the vial resides interiorly of the adapter subassembly.

As best seen in FIG. 39, a second hollow piercing cannula 450 is connected to a support wall 452 formed on a vial receiving tube 445. Cannula 450 extends into receiving chamber 445a formed in vial receiving tube 445 in the manner shown in FIG. 39. A passageway 454 formed in closure cap 409 communicates with the fluid passageway 450a of hollow cannula 450 via a check valve 456, which is mounted within a chamber 458 formed in cap 409. Check valve 456 permits fluid flow into passageway 438, into inlet passageway 407 via check valve 62 and finally into reservoir 58. However check valve 456 effectively blocks the fluid flow into the opposite direction. When the third fill means is not in use, chamber 447 is sealably closed by a removable sealing cap 460 which is of the construction shown in FIG. 53. Cap 460 includes a pull tab 460a for use in conveniently separating the cap from housing portion 401e.

In using the apparatus of this latest form of the invention, reservoir 58 can be initially filled by the fill means or assembly 86, with a diluent or other fluid. This done, a first container subassembly 98 can be mated with a first adapter subassembly 96 in the manner previously described. Next, the tear-away closure cap 60, which seals chamber 433 of lower housing 401d, is removed (FIG. 39). This done, housing 68 of adapter the assemblage can be pushed forwardly within chamber 433. As the adapter subassembly moves forwardly, pusher rod 106 will engage plunger 104 causing the container assembly to also move forwardly. As the container assembly approaches a seated position, piercing cannula 108 will pierce septum assembly 100 of the first container assembly. Once the fluid flow path between the hollow cannula and the fluid reservoir 58 is thus created via passageways 438 and 407, a continued inward movement of the first adapter subassembly 88 will cause pusher rod 106 thereof to move plunger 104 forwardly of chamber 96b. As plunger 104 is moved forwardly, the medicament or other fluid contained within chamber 96b of first vial 96 will flow through passageway of the hollow cannula, past check valve 442, into passageway 438, past check valve 62 and finally into fluid reservoir 58 where it will intermix with the diluent or other fluid introduced into the reservoir using the first fill means.

If desired, a second subassembly can be mated with a second adapter subassembly 96 in the manner previously described. This done the tear away closure cap 460, which seals chamber 447 of upper housing 401e is removed (FIG. 39) so that the second adapter assemblage can be pushed forwardly within chamber 447. As the adapter subassembly moves forwardly, pusher rod 106 of the second adapter assemblage will engage plunger 104 causing the container assembly to also move forwardly. As the second container assembly approaches a seated position, piercing cannula 450 will pierce septum assembly 100 of the second assembly. Once the fluid flow path between hollow cannula 450 and the fluid reservoir 58 is thus created via passageways 454, 438, and 407, a continued inward movement of the second adapter subassembly 88 will cause pusher rod 106 thereof to move plunger 104 forwardly of chamber 96b. As plunger 104 is moved forwardly, the medicament or other fluid contained within chamber 96b of the second vial 96 will flow through passageway 450a of the hollow cannula 450, past check valve 456, into passageway 438, past check valve 62 and finally into reservoir 58 where it will intermix with the diluent or other fluid introduced into the reservoir using the first and second fill means of the invention.

It is to be understood that with the novel construction of the apparatus of this latest form of the invention, reservoir 58 can be fully or partially filled using any one of the first, second and third fill means. Alternatively various mixtures of fluid within reservoir 58 can be achieved by using a selected combination of the first, second and third fill means.

During filling of the reservoir using a selected fill means, or a combination fill means, membrane 46 will be distended outwardly in the manner shown in FIG. 39 wherein the central portion thereof is spaced from support 404. Rings 50 which are in clamping engagement with support 404 function to seal the membrane against the end portions of the support and prevent leakage of fluid between the membrane and the support.

After the reservoir has been appropriately filled with a desired medicament or other fluid using the first, second, or third fill means of the apparatus, the reservoir will remain in this filled condition until the outlet flow path of the device is opened. Following opening of the outlet flow path, the stored energy means or membrane 46 will tend to return to a less distended condition causing fluid to flow outwardly of the apparatus via passageway 412, through rate control frit 74 and finally outwardly of the device via delivery passageway 414. To interconnect passageway 414 with the patient, a conventional infusion set including a delivery line 71 is connected to connector 72 in the manner previously described in connection with the embodiments shown in FIGS. 1 through 9. In this regard, end portion 401b of the device housing includes a hollow, generally cylindrically shaped housing 401f which is provided with a yieldably deformable, hook-like locking tabs 401g (see also FIG. 48). Tabs 401g which are constructed from a yieldably deformable plastic, lockably receive shoulder 73 of body portion 72 in the manner shown in FIG. 39 so as to releasably secure connector 72 within housing 401f of end portion 401b.

In order to securely lock the adapter subassemblies 98 within portions 401d and 401e, after the reservoir has been filled, novel locking means are provided. These locking means are identical to those described in connection with the embodiment shown in FIGS. 1 through 8 and operate in the same way. More particularly, the locking means comprise a series of locking teeth 98d which are constricted so that, as the adapter subassembly 98 is moved inwardly, they will slide under flexible tabs 113a formed on a pair of clips 113 (FIGS. 51 and 52) which is disposed proximate the entrance of receiving chambers 433 and 447. As before, once the adapter subassemblies have reached the fully forward position within the device housing, locking tabs 465 will engage one of the teeth 96d and effectively prevent removal of the adapter subassemblies from passageways 433 and 447. With this construction, once the reservoir 58 has been filled with the fluid "F" contained in the two container subassemblies, the adapter assemblies cannot be removed from the fluid dispensing device and, thereby prevent system adulteration.

Turning next to FIGS. 55 through 73, still another form of the fluid dispenser apparatus of the invention is there illustrated and generally designated by the numeral 470. This latest form of the invention is similar in some respects to that shown in FIGS. 27 through 36 and like numerals are used to identify like components. As in the embodiment shown in FIGS. 27 through 36, the present embodiment comprises an elongated housing 472 having a first internal chamber 474, a support 476 disposed within internal chamber 474 and extending longitudinally of the housing 472, and a stored energy means provided in the form of a generally cylindrically shaped, elongated elastomeric member 308 (FIG. 56).

Housing 472 comprises a cylindrically shaped central portion 472a and inlet and outlet closure portions 472b and 472c respectively. Central section 472a can be connected to end plate portions 472b and 472c by any suitable means such as adhesive bonding or an appropriate sonic weldment. Elastomeric member 308 is securely affixed proximate its ends to support 476 by means of suitable ring clamps 310 such as self-locking plastic panduit strips.

Figure 56:
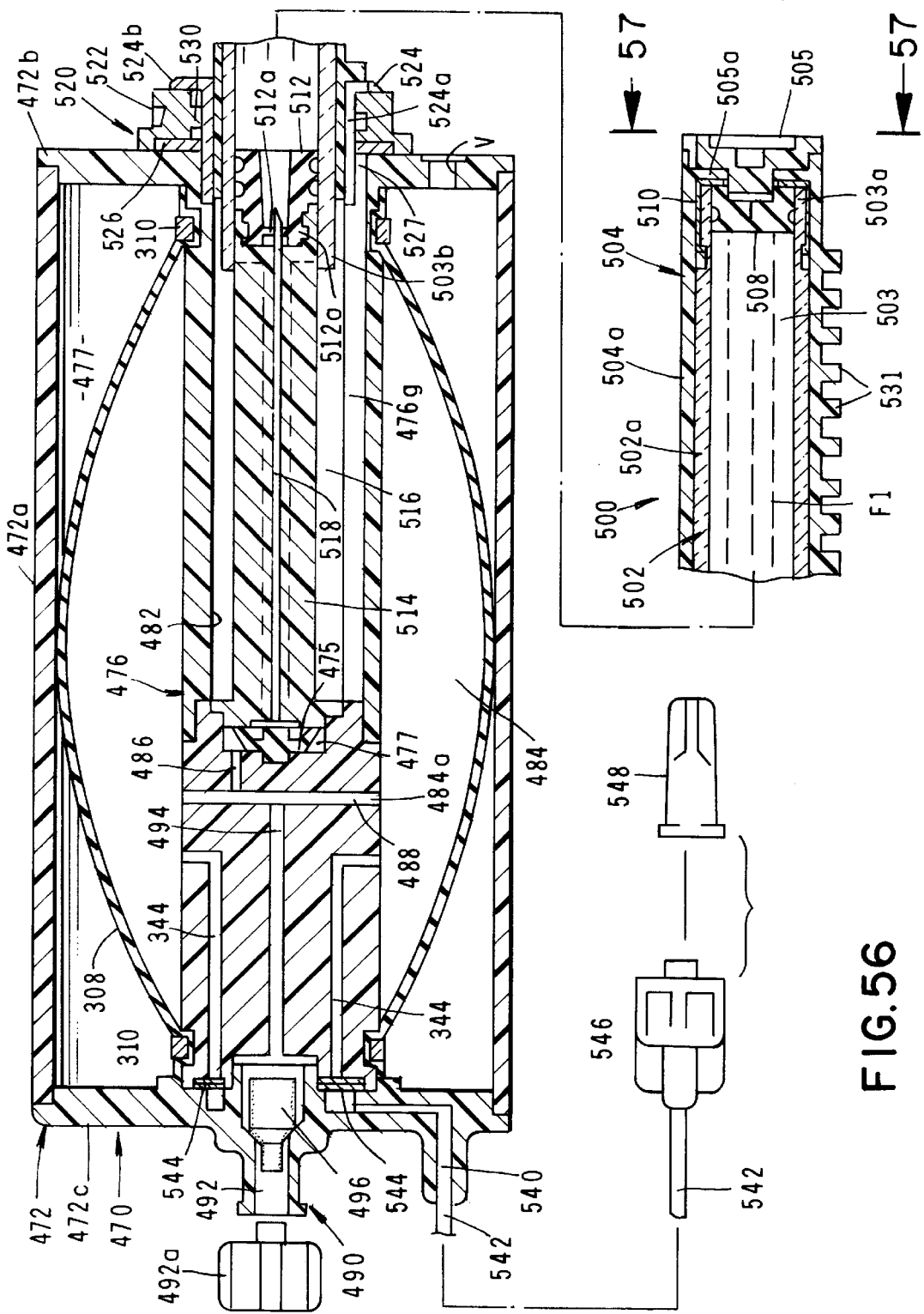
FIG. 56 is an enlarged, side-elevational, cross-sectional view of the device shown in FIG. 55.

As best seen by referring to FIG. 56, support 476 is provided with a receiving chamber 482 which, in a manner presently to be described, telescopically receives the first fill means of the invention for filling a reservoir 484 with a selected fluid. Reservoir 484 is formed by elastomeric member 308 and the central portion of support 476. Valve means, shown here as a check valve 475 is disposed within a chamber 477 and functions to permit, fluid flow toward reservoir 484, but blocks fluid flow in the opposite direction.

Support 476 is provided with an inlet passageway 486 which communicates with a transversely extending passageway 488. A second fill means which includes a luer connector 490 having a fluid passageway 492 is provided as a part of closure portion 472c. When the device is not in use, passageway 492 is suitably closed by a closure cap 492a (FIGS. 56). As shown in FIG. 56, passageway 492 is in communication with passageway 488 via a passageway 494 and a first flow control means here provided as a check valve 496. As will presently be described, the second fill means can also be used to fill or partially fill reservoir 484 with a selected fluid.

Provided at the opposite end of the assemblage from luer-like connector 492 is the important dose dial means for this latest form of the invention for introducing a precise dose volume of medicament to be introduced into reservoir 484 from the second fill means of the invention, the character of which will next be described. Considering once again the first fill means of the invention and turning to FIGS. 56, 71 and 73, this important fill means, which is generally designated as 500, here comprises a container subassembly 502, and an adapter subassembly 504. Container subassembly 502 includes a container or vial portion 502a having a fluid chamber 503 for containing an injectable fluid "F". Fluid chamber 503 is provided with first and second open ends 503a and 503b. First opened 503a is sealably closed by closure means here provided in the form of a pierceable septum 508. Septum 508, which may be a slit septum, is held securely in position by clamping ring 510. Second end 503b is closed by an apertured, removable peel away cover 507 (FIG. 72). A plunger 512 is telescopically movable within chamber 503 of container subassembly 502 in the manner indicated in the drawings. Slit septum 508 is accessible by lifting a hingeably mounted end panel 505 which forms a part of adapter subassembly 504. Panel 505 is connected by means of a living hinge 505a to an adapter sleeve 504a that forms a part of adapter subassembly 504. When panel 505 is lifted in the manner shown in FIG. 73, slit septum 508 can be penetrated by a blunt end cannula "C" of a conventional syringe assembly "S" or like filling means. As chamber 503 is filled with fluid, plunger 512 will be moved from the first position shown in FIG. 71 to the second position shown in FIG. 73.

As best seen in FIG. 56, adapter subassembly 504 includes an adapter sleeve 504a that has a first open end 506 that telescopically receives the container subassembly in the manner best seen in FIG. 56. Following removal of peel-away cover 507, adapter sleeve 504a is telescopically receivable within receiving chamber 482 of support 476 and is moved by the advancement means of the invention from a first extended position shown in FIG. 56 into a second fluid filling position. Support 476 also includes pusher means shown here as an elongated pusher member 514 (FIG. 56) which functions to move plunger 512 within the fluid chamber 503 of the container subassembly upon operation of the dose dialing means of the invention.

As indicated in FIG. 56, pusher member 514 is radially spaced from the interior wall of receiving chamber 482 so as to define a longitudinally extending annular space 516. With this construction, during the mating of the first fill means with the fluid delivery component, the outer wall of adapter subassembly 504 and a portion of the container 502a are closely received within annular space 516 as the adapter subassembly is moved inwardly or forwardly of the device housing by the dose dialing means of the advancement means of the invention. When the adapter assembly is originally mated with the delivery component in the manner shown in FIG. 56, a pierceable wall 512a of plunger 512 of container assembly 502 will move into piercing engagement with a hollow cannula 518 which is disposed centrally of pusher member 514.

Once the fluid flow path between the hollow cannula 518 and the fluid reservoir 484 of the apparatus is thus created via check valve 475, passageway 486 and a passageway 488, an inward movement of the adapter subassembly can be accomplished using the novel dose dialing means of the invention. As the dose dialing means controllably moves the adapter subassembly inwardly, pusher member 514 will move plunger 512 inwardly of fluid chamber 503 causing fluid contained within vial chamber 503 to flow through hollow cannula 518, past umbrella check valve 475 into passageway 486, into passageway 488 and into fluid reservoir 484 (FIG. 56). As fluid reservoir 484 is filled, air trapped within housing 472 is vented to atmosphere via vent "V" (FIG. 56). As will be discussed hereinafter, in certain instances, reservoir 484 may be prefilled using the second fill means of the invention with a solution with which the fluid contained in vial subassembly 502 will be controllably intermixed as the adapter subassembly is moved inwardly. It is to be understood that cannula 518 can also be a blunt end cannula and wall 512 can be manufactured with a slit portion.

Figure 70:
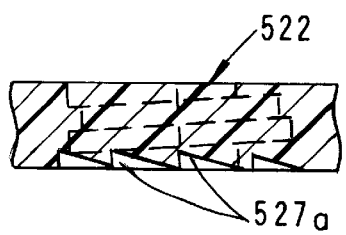
FIG. 70 is a cross-sectional view taken along lines 70—70 of FIG. 66.

Considering now the previously mentioned dose dialing means of the invention, this important means here comprises advancement means connected to closure plate 472b of the fluid delivery component and functions to controllably advance adapter subassembly 504 into annular space 516. In the form of the invention shown in the drawings, this important advancement means can be seen to comprise an advancing subassembly 520 that includes an advancing dial 522 which is rotatably connected to end wall 472b in the manner indicated in FIG. 56. Advancing subassembly 520 also includes a dial support component 524, which is of the configuration best seen in FIGS. 62, 67, and 68. Additionally, advancing subassembly 520 includes a locating ring 526 of the character illustrated in FIGS. 62 and 65. Locating ring 526 is provided with a yieldably deformable, reverse rotation blocking tab 526b (FIG. 65) which engages teeth 522a provided on advancing dial or ring 522 to prevent reverse rotation thereof (FIG. 70). Teeth 522a also provided a tactile response upon rotation of advancing dial 522.

Figure 68:
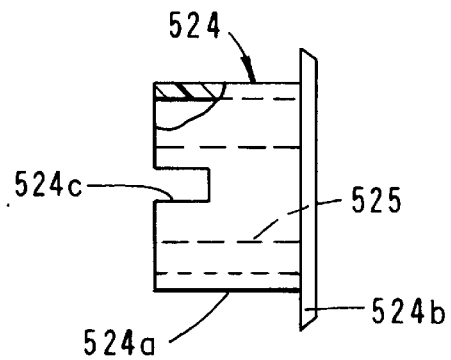
FIG. 68 is a view taken along lines 68—68 of FIG. 62.
Figure 69:
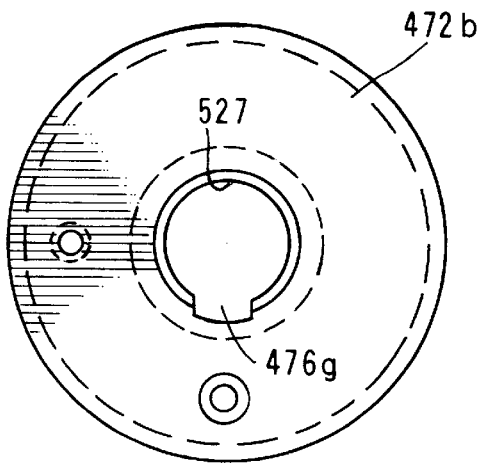
FIG. 69 is a view taken along lines 69—69 of FIG. 62.
Figure 69A:
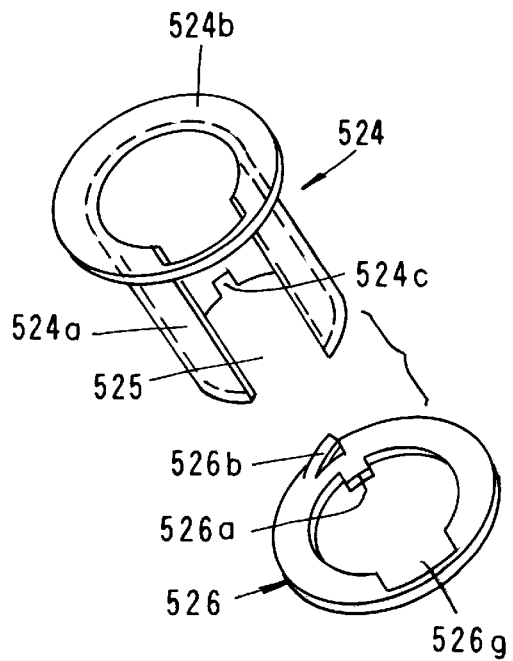
FIG. 69A is a generally perspective, fragmentary view of the support and locator rings of the device.

Dial support component 524 includes a skirt like portion 524a which is receivable within an opening 527 formed in support 476 (FIG. 62) and a flange portion 524b. Locating ring 526 is provided with a locating tab 526a (FIG. 65) which is receivable within a locating slot 524c formed in skirt portion 524a of dial support component 524 (FIG. 68). When the various components of the advancement means are assembled in a manner shown in FIG. 56, advancing dial 522 is held captive between flange 524b and locating ring 526.

Figure 62:
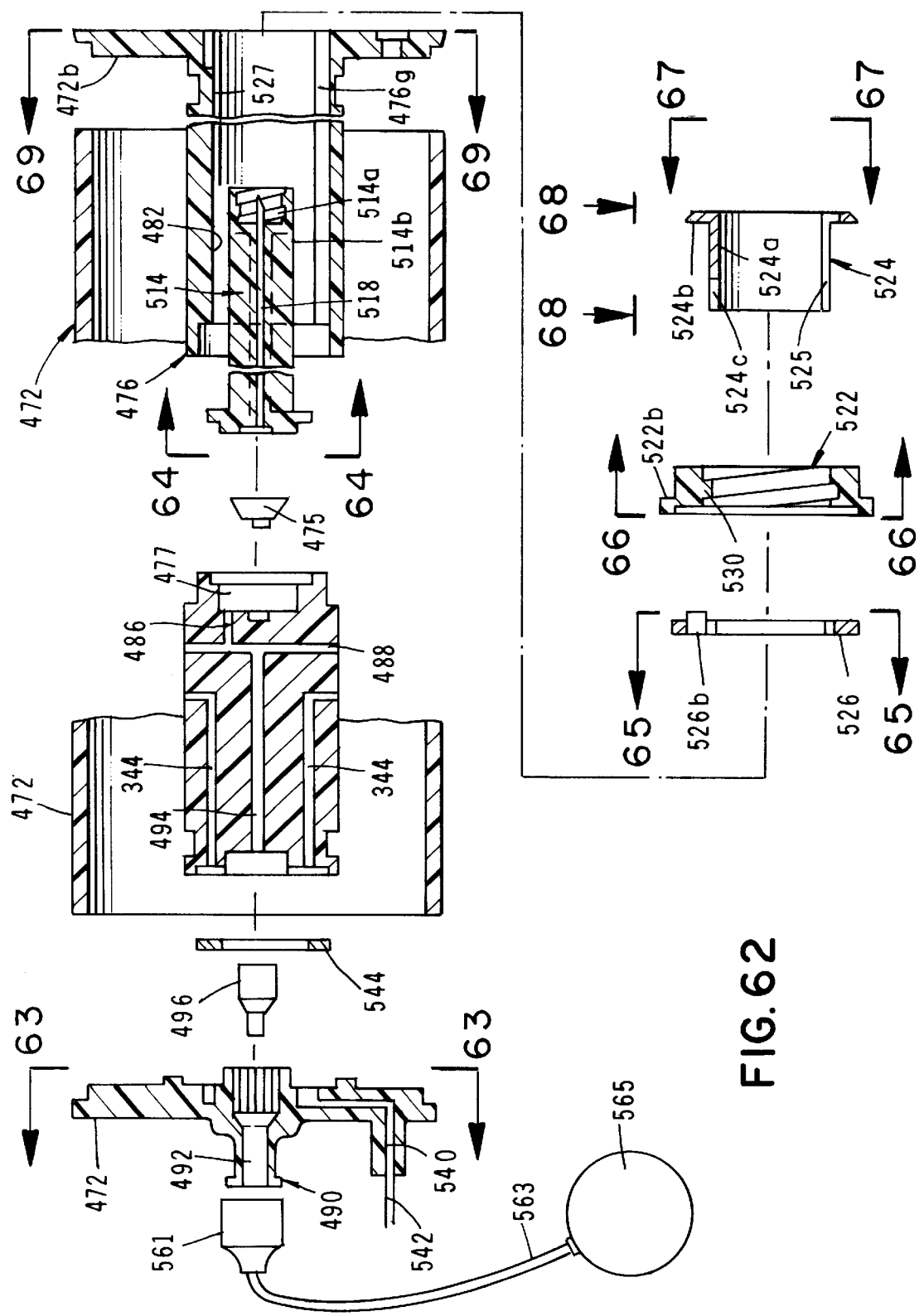
FIG. 62 is an exploded, cross-sectional view of the delivery device portion of the apparatus shown in FIG. 56.
Figure 63:
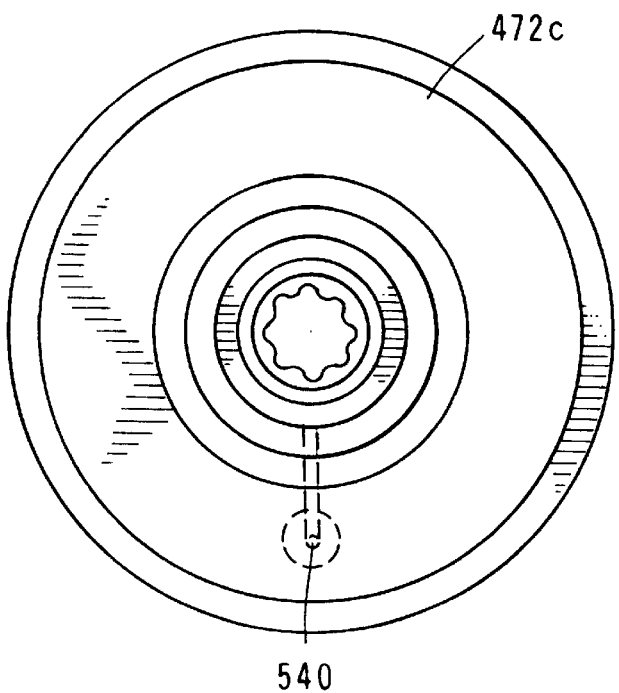
FIG. 63 is a view taken along lines 63—63 of FIG. 62.
Figure 64:
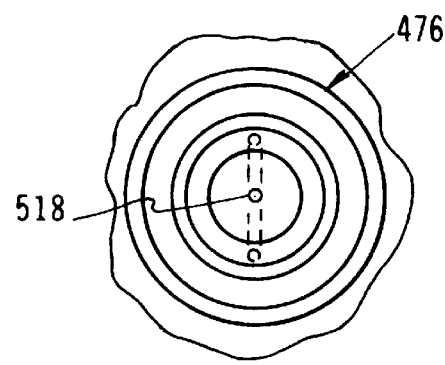
FIG. 64 is a view taken along lines 64—64 of FIG. 62.
Figure 65:
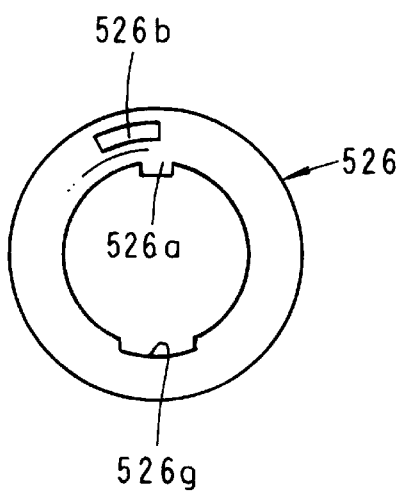
FIG. 65 is a view taken along lines 65—65 of FIG. 62.
Figure 66:
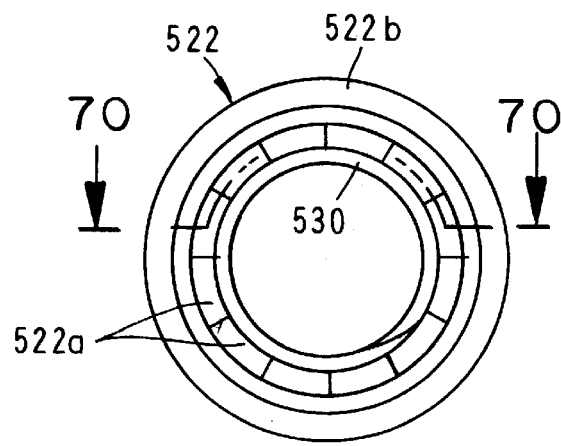
FIG. 66 is a view taken along lines 66—66 of FIG. 62.
Figure 67:
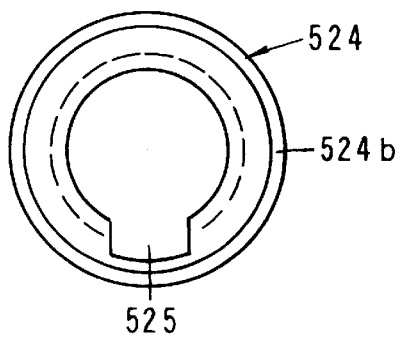
FIG. 67 is a view taken along lines 67—67 of FIG. 62.

As shown in FIGS. 56 and 62, advancing dial 522 includes teeth engaging means here provided as threads 530 formed on the interior wall of advancing dial 522. Upon insertion of adapter sleeve 504 into annular space 482, threads 530 will mate with a plurality of longitudinally spaced advancing teeth 531 formed on the exterior wall of adapter sleeve 504 (FIGS. 56, 71 and 73). With this construction it is apparent that rotation of the advancing dial 522 will cause adapter sleeve 504 to be incrementally advanced into annular space 482. As the adapter sleeve so advances, pusher member 514 will urge plunger 512 inwardly of fluid chamber 503 of container subassembly 502. As shown in FIGS. 57, 67, 68 and 69A, dial support component 524 is provided with a guide slot 525 (FIG. 67). Similarly, locating ring 526 and support 476 are both provided with guide slots 526g and 476g respectively, which index with guide slot 525. These guide slots function to guide the travel of teeth 531 as adapter sleeve 504 advances into annular space 482.

After the container of the container subassembly has been filled using syringe "S", either in the field or at the time of manufacture, and following removal of peel-away cover 507, the container subassembly can be coupled with the fluid delivery component in the manner shown in FIG. 56. As the container subassembly is coupled with the delivery device, threads 512b formed on plunger 512 threadably engage threads 514a formed on a head portion 514b of pusher member 514 (FIG. 62) causing hollow cannula 518 to pierce wall 512a of the plunger 512. An inward movement of the plunger resulting from one rotation of dial 522 will then cause one-tenth of the fluid contained within fluid chamber 503 of the container subassembly 502 to flow into the hollow cannula, past umbrella-like check valve 475, into passageway 486, into passageway 488 and then into reservoir 484 via inlet 484a. It should be noted that once adapter sleeve 504 is advanced into annular space 482, it cannot be retracted, thereby preventing system adulteration.

Figure 57:
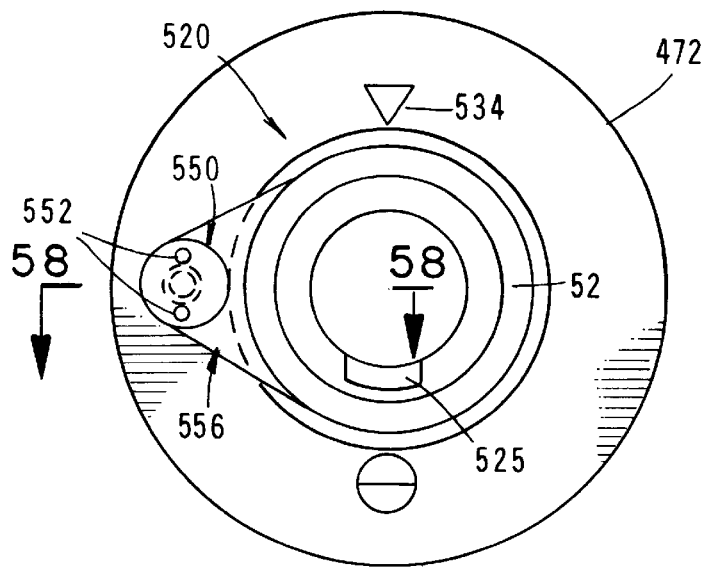
FIG. 57 is a view taken along lines 57—57 of FIG. 56.
Figure 59:
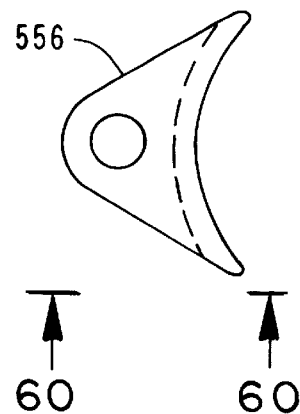
FIG. 59 is a top plan view of the dial clamp component of the apparatus.
Figure 60:
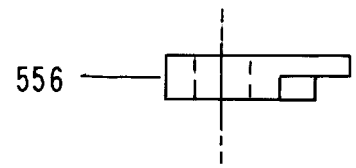
FIG. 60 is a view taken along lines 60—60 of FIG. 59.
Figure 74:
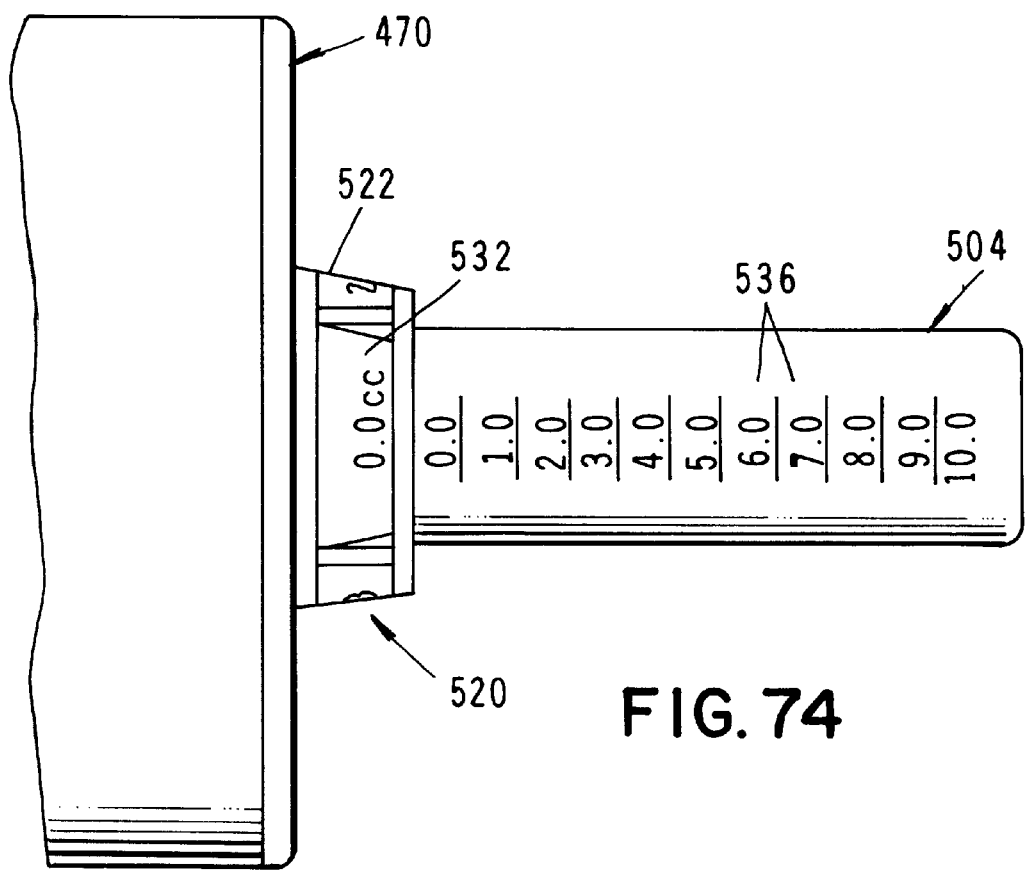
FIG. 74 is a fragmentary, top plan view of the right-hand portion of the fluid delivery component having the dose volume indicia provided on the adapter component.
Figure 75:
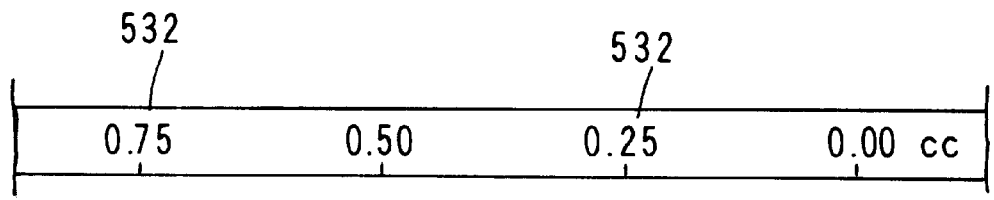
FIG. 75 is a diagrammatic view of the dosing indicia provided on the dose-dialing component of the apparatus.

Referring next to FIGS. 74 and 75 it is to be noted that advancing dial 522 is provided with circumferentially spaced incremental indicating indicia 532. As advancing dial 522 is rotated, the indicia 532 will move sequentially past an indicating arrow 534 imprinted on end plate 472b (FIG. 57). As shown in FIG. 75, the hollow housing of the adapter subassembly 504 is provided with longitudinally spaced dose volume indicating indicia 536. Each of the indicia 536 indicates one-tenth of the volume of the container or vial of the vial subassembly 502. Similarly the indicating indicia 532 imprinted on advancing dial 522 indicate a ¼ division of the indicia 536 imprinted on the hollow housing of the adapter sleeve 504, that is 0.25, 0.50 and 0.75. Accordingly when advancing dial 522 is rotated a full 360 degrees, one-tenth of the fluid contained within the vial will be introduced into reservoir 484. In similar fashion when the advancing dial 522 is rotated ¼ of a turn as indicated by the indicia 532, 0.025 of the fluid contained within the vial will be introduced into reservoir 484 (FIG. 56). With this arrangement, the volume of fluid introduced into reservoir 484 by the rotation of advancing dial 522 can be precisely controlled. It is to be understood that indicia indicating alternate dosing parameters can be used if desired with corresponding alternate thread configurations on the adapter sleeve and advancing dial.

Figure 55:
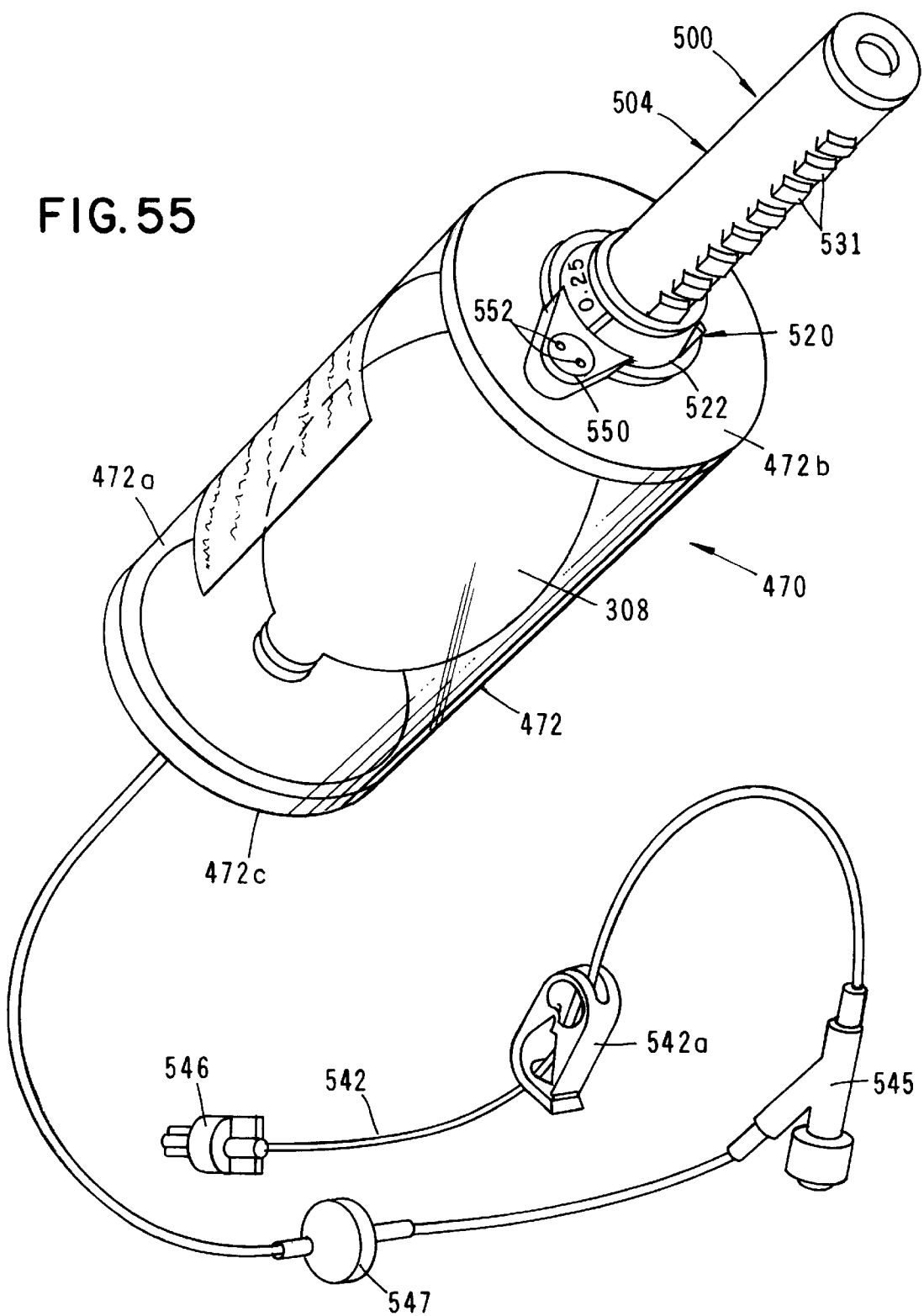
FIG. 55 is a generally perspective view of yet another embodiment of the fluid delivery apparatus of the present invention which includes a novel dose dialing feature.

Once the reservoir has been filled, the apparatus will remain in this readied condition until the line clamp 542a provided on the delivery line 542 of the device is opened (FIG. 55). Once the line clamp is opened, the stored energy means or membrane 308 will tend to return to a less distended condition causing fluid to flow outwardly of the apparatus via passageways 344 formed in support 476, through the novel flow control means of the invention, here shown as porous flow control elements 544 (FIG. 56) which may comprise filter elements of a character well known to those skilled in the art and finally outwardly of the device via the infusion line 542.

Provided at the outboard end of the delivery line 542 is a luer connector 546 which is closed by a removable cap 548. Disposed intermediate line clamp 542 and the outlet 540 of the device is a Y-site 545 that can be used for bolus injections and a conventional filter and gas vent 547 (FIG. 55).

Figure 58:
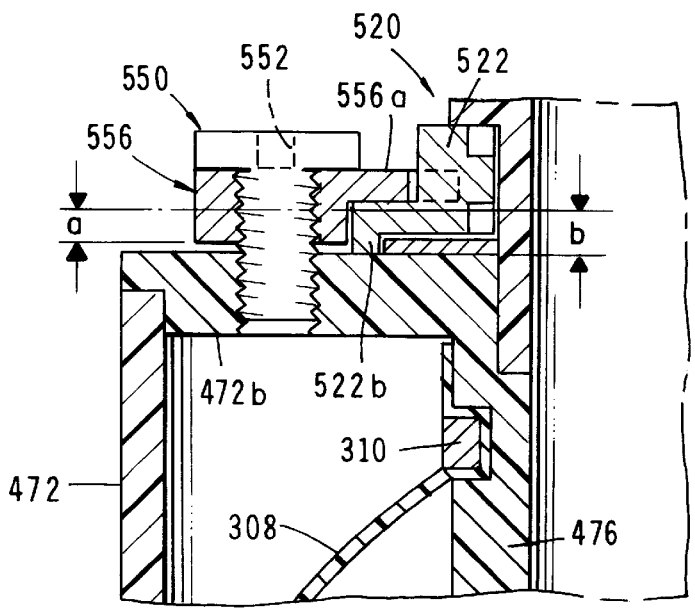
FIG. 58 is a cross-sectional view taken along lines 58—58 of FIG. 57.
Figure 61:
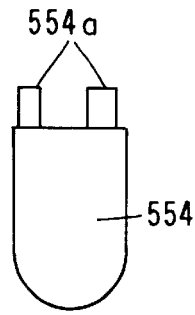
FIG. 61 is a top plan view of the physician's key of the invention for locking the dose dialing mechanism of the device.

Referring particularly to FIGS. 58 through 61, the novel locking means of the invention is shown. This locking means prevents further adjustment of the dose dialing means once the dosing regimen has been set by the physician or care-giver. The locking means here comprises a locking member 550 that threadably connects dial clamp 556 to closure wall 472b in the manner illustrated in FIG. 58. Dial clamp 556 includes a flange portion 556a that frictionally contacts a matching surface of flange portion 522b on advancing dial 522 to prevent further rotation of the dial when locking member 550 is in its fully threaded position. In this regard, it is to be noted that the dimension "a" in FIG. 58 is less than dimension "b" so that when member 550 is tightened, clamp 556 will engage flange portion 522b causing a friction type brake. As indicated in FIG. 57, locking member 550 is provided with spaced apart spanner receiving openings 552 which are adapted to receive spanner elements 554a of a physician's key 554 of the character shown in FIG. 61. Using the physician's key, the physician or caretaker can rotate locking member 550 so that it moves dial clamp 556 into locking engagement with flange portion 522b of dose dial 522 thereby preventing further operation of the advancement means.

As previously mentioned, reservoir 484 can also be filled using the second fill means of the invention which comprises luer-like connector 490 and check valve 496. This is accomplished by interconnecting with connector 490 an appropriate fill line having a luer connector 561 that is matable with connector 490. The fill line, identified by the numeral 563 in FIG. 62, can be interconnected with any desired source of fluid 565 which may be a diluent or an appropriate beneficial agent.

Having now described the invention in detail in accordance with the requirements of the patent statutes, those skilled in this art will have no difficulty in making changes and modification s in the individual parts or their relative assembly in order to meet specific requirements or conditions. Such changes and modifications may be made without departing from the scope and spirit of the invention, as set forth in the following claims.

I claim:
1. A fluid delivery apparatus having a fluid delivery passageway, said apparatus comprising:
  (a) an elongated housing having walls defining an internal chamber;
  (b) a support assembly connected to said housing an including an elongated body disposed within said internal chamber, said body having a receiving chamber, an inlet passageway and an outlet passageway in communication with said fluid delivery passageway;
  (c) an elongated tubular shaped, elastomeric member connected proximate its ends to said elongated body, said elastomeric member having a central portion disposed within said internal chamber of said housing and overlaying said inlet and outlet passageways, said central portion of said elastomeric member being distendable by fluid flowing through said first fluid passageway from a first position in proximity with said support to a second position to form a fluid reservoir;
  (d) fill means interconnected with said housing for filling said reservoir, said fill means comprising:
    (i) a container subassembly including a container having a fluid chamber and displacement means movable relative to said fluid chamber for dispensing fluid from said chamber;
    (ii) an adapter subassembly comprising a hollow housing for telescopically receiving at least a part of said container subassembly and means for moving said displacement means relative to said fluid chamber of said container; and
    (iii) advancement means connected to said housing for controllably advancing said adapter subassembly into said receiving chamber of said housing, said advancement means comprising an advancing dial rotatably connected to said housing for movement between first and second positions.
2. The fluid delivery device as defined in claim 1 in which said hollow housing of said adapter subassembly is provided with longitudinally spaced apart advancing teeth and in which said advancing dial of said advancing means includes teeth engaging means for engagement with said teeth of said hollow housing to incrementally advance said hollow housing into said receiving chamber upon rotation of said advancing dial from said first position to said second position.

3. The fluid delivery device as defined in claim 1 further including locking means for locking said advancing means to prevent advancing of said the adapter subassembly.

4. The fluid delivery device as defined in claim 1 further including infusion means connected to said housing and being in fluid communication with said reservoir for infusing medicinal fluids into a patient.

5. The fluid delivery device as defined in claim 1 further including second fill means connected to said housing for introducing fluids into said reservoir.

6. The fluid delivery device as defined in claim 5 in which said second filling means comprises a luer connector affixed to said housing and a check valve for controlling fluid flow toward said reservoir.

7. A fluid delivery device having a fluid delivery passageway, said apparatus comprising:
 (a) an elongated housing having walls defining an internal chamber;
 (b) a support assembly connected to said housing and including an elongated body disposed within said internal chamber, said body having a receiving chamber, a pusher member disposed within said receiving chamber and an inlet passageway and an outlet passageway, said outlet passageway being in communication with said fluid delivery passageway;
 (c) an elongated tubular shaped elastomeric member connected proximate its ends to said elongated body, said elastomeric member having a central portion disposed within said internal chamber of said housing and overlaying said inlet and outlet passageways, said central portion of said elastomeric member being distendable by fluid flowing through said first fluid passageway from a first position in proximity with said support to a second position to form a fluid reservoir;
 (d) fill means interconnected with said housing for filling said reservoir, said fill means comprising:
   (i) a container subassembly including a container having a fluid chamber and displacement means movable relative to said fluid chamber for dispensing fluid from said chamber;
   (ii) an adapter subassembly comprising a hollow housing for telescopically receiving at least a part of said container subassembly, said hollow housing having longitudinally spaced-apart advancing teeth;
   (iii) advancement means connected to said housing for controllably advancing said adapter subassembly into said receiving chamber of said housing, said advancement means comprising an advancing dial rotatably connected to said housing for movement between first and second positions, said advancing dial having teeth engaging means for engaging said advancing teeth of said hollow housing of said adapter subassembly.

8. The fluid delivery device as defined in claim 7 in which said advancing dial of said advancement means includes circumferentially spaced, incremental indicating indicia and in which said hollow housing of said adapter subassembly includes longitudinally spaced dose volume indicating indicia.

9. The fluid delivery device as defined in claim 7 further including locking means for locking said advancement means to prevent advancing of said adapter subassembly.

10. The fluid delivery device as defined in claim 7 further including infusion means connected to said housing and in fluid communication with said reservoir for infusing medicinal fluids into a patient.

11. The fluid delivery device as defined in claim 7 in which said displacement means of said container subassembly includes a plunger having a pierceable wall and in which said support assembly includes a piercing cannula for piercing said pierceable wall of said plunger, said piercing cannula being in communication with said inlet to said reservoir.

12. The fluid delivery device as defined in claim 7 in which said container subassembly further includes a pierceable septum.

13. The fluid delivery device as defined in claim 7 in which said hollow housing of said adapter subassembly has first and second open ends and a closure panel hingeably connected to said hollow housing for closing said first open end.

14. The fluid delivery device as defined in claim 7 further including second fill means connected to said housing for introducing fluid into said reservoir.

15. A fluid delivery device having a fluid delivery passageway, said apparatus comprising:
 (a) an elongated housing having walls defining an internal chamber;
 (b) a support assembly connected to said housing and including an elongated body disposed within said internal chamber, said body having a receiving chamber, a pusher member disposed within said internal chamber and an inlet passageway and an outlet passageway, said outlet passageway being in communication with said fluid delivery passageway;
 (c) an elongated tubular shaped elastomeric member connected proximate its ends to said elongated body, said elastomeric member being distendable by fluid flowing through said inlet passageway from a first position in proximity with said support to a second position to form a fluid reservoir;
 (d) fill means interconnected with said housing for filling said reservoir, said fill means comprising:
   (i) a container subassembly including a container having:
     a. a fluid chamber;
     b. displacement means movable relative to said fluid chamber having first and second ends for dispensing fluid from said chamber; and
     c. a pierceable septum closing one of said first and second ends of said fluid chamber;
   (ii) an adapter subassembly comprising a hollow housing for telescopically receiving at least a part of said container subassembly, said hollow housing having:
     a. first and second ends and longitudinally spaced-apart advancing teeth; and
   (iii) advancement means connected to said housing for controllably advancing said adapter subassembly into said receiving chamber of said housing, said advancement means comprising an advancing dial rotatably connected to said housing for movement between first and second positions, said advancing dial having:
     a. teeth engaging means for engaging said advancing teeth of said hollow housing of said adapter subassembly; and
     b. circumferentially spaced, incremental indicating indicia.

16. The fluid delivery device as defined in claim 15 further including locking means for locking said advancing means to prevent advancing of said adapter subassembly.

17. The fluid delivery device as defined in claim 15 further including infusion means connected to said housing and in fluid communication with said reservoir for infusing medicinal fluids into a patient.

18. The fluid delivery device as defined in claim 15 further including second fill means for introducing fluid into said reservoir.

19. The fluid delivery device as defined in claim 15 further including flow control means for controlling fluid flow between said reservoir and said fluid delivery passageway.

20. The fluid delivery device as defined in claim 15 in which one of said first and second ends of said adapter subassembly is sealably closed by a peel-away cover.

21. The fluid delivery device as defined in claim 15 in which said displacement means of said container subassembly includes a plunger having a pierceable wall and in which said support assembly includes cannula means for piercing said pierceable wall of said plunger, said piercing cannula being in communication with said inlet to said reservoir.

22. The fluid delivery device as defined in claim 20 in which said cannula means comprises a bunt end cannula.

23. The fluid delivery device as defined in claim 22 in which said pierceable wall of said plunger comprises a slitted portion to accept said blunt end cannula.

* * * * *